United States Patent
Isakson et al.

(10) Patent No.: US 10,314,883 B2
(45) Date of Patent: Jun. 11, 2019

(54) COMPOSITIONS AND METHODS FOR REGULATING BLOOD PRESSURE

(71) Applicant: University of Virginia Patent Foundation, Charlottesville, VA (US)

(72) Inventors: Brant E. Isakson, Charlottesville, VA (US); Marie Billaud, Mount Washington, PA (US); Leon J. DeLalio, Wading River, NY (US); Thu Le, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 15/549,232

(22) PCT Filed: Feb. 12, 2016

(86) PCT No.: PCT/US2016/017830
§ 371 (c)(1),
(2) Date: Aug. 7, 2017

(87) PCT Pub. No.: WO2016/130966
PCT Pub. Date: Aug. 18, 2016

(65) Prior Publication Data
US 2018/0028595 A1 Feb. 1, 2018

Related U.S. Application Data

(60) Provisional application No. 62/115,685, filed on Feb. 13, 2015, provisional application No. 62/198,480, filed on Jul. 29, 2015.

(51) Int. Cl.
| | | |
|---|---|---|
| A61K 38/08 | (2019.01) | |
| A61K 38/16 | (2006.01) | |
| A61P 9/08 | (2006.01) | |
| A61P 9/00 | (2006.01) | |
| A61K 38/10 | (2006.01) | |
| C07K 14/705 | (2006.01) | |
| C07K 7/06 | (2006.01) | |
| C07K 14/16 | (2006.01) | |
| A61K 38/20 | (2006.01) | |
| A61K 38/00 | (2006.01) | |

(52) U.S. Cl.
CPC .............. *A61K 38/08* (2013.01); *A61K 38/10* (2013.01); *A61K 38/2013* (2013.01); *C07K 7/06* (2013.01); *C07K 14/163* (2013.01); *C07K 14/705* (2013.01); *A61K 38/00* (2013.01); *C07K 2319/00* (2013.01); *C07K 2319/10* (2013.01)

(58) Field of Classification Search
None
See application file for complete search history.

(56) References Cited

U.S. PATENT DOCUMENTS

2010/0311647 A1 12/2010 Halem et al.
2013/0156791 A1 6/2013 Perfettini et al.

FOREIGN PATENT DOCUMENTS

WO    WO 05007090    1/2005

OTHER PUBLICATIONS

Li et al., "Characterization of Novel Pannexin 1 Isoforms from Rat Pituitary Cells and their Association with ATP-gated P2X Channels," Gen Comp Endocrinol. 174: 202-210 (2011).*
Akers et al., "Peptides and proteins as parenteral solutions", Pharmaceutical Formulation Development of Peptides and Proteins, Frokjaer and Hovgaard, eds; 2nd Ed., Chptr 8, pp. 145-177 (2012).*
Billaud, et. al., "Pannexin1 Regulates α1-Adrenergic Receptor-Mediated Vasoconstriction", Circ. Res. Jun. 24, 2011, vol. 109, No. 1, pp, Especially Abstract, p. 81, col. 2, para 2 to p. 82, col. 1, para 1; p. 83, Figure 4E, p. 84, col. 1, para 2; p. 84, col. 2, para 2.
E0X643, UniProtKB Accession No. E0X643, Oct. 1, 2014 (online). (Retrieved on Apr. 22, 2016). Retrieved from the internet <URL: http://www.uniprot.org/uniprot/E0X643.txt?version=13> Entire document.

(Continued)

*Primary Examiner* — Julie Ha
*Assistant Examiner* — Kristina M Hellman
(74) *Attorney, Agent, or Firm* — Rodney L. Sparks

(57) ABSTRACT

Both purinergic signaling through nucleotides such as ATP and noradrenergic signaling through molecules such as norepinephrine regulate vascular tone and blood pressure. Pannexin1 (Panx1), which forms large-pore, ATP-releasing channels, is present in vascular smooth muscle cells in peripheral blood vessels and participates in noradrenergic responses. Using pharmacological approaches and mice conditionally lacking Panx1 in smooth muscle cells, we found that Panx1 contributed to vasoconstriction mediated by the α1 adrenoreceptor (α1AR), whereas vasoconstriction in response to serotonin or endothelin-1 was independent of Panx1. Analysis of the Panx1-deficient mice showed that Panx1 contributed to blood pressure regulation especially during the night cycle when sympathetic nervous activity is highest. Using mimetic peptides and site-directed mutagenesis, we identified a specific amino acid sequence in the Panx1 intracellular loop that is essential for activation by α1AR signaling. Collectively, these data describe a specific link between noradrenergic and purinergic signaling in blood pressure homeostasis.

19 Claims, 45 Drawing Sheets
(38 of 45 Drawing Sheet(s) Filed in Color)
Specification includes a Sequence Listing.

(56) References Cited

OTHER PUBLICATIONS

Billaud, et al., "Pannexin 1 in the regulation of vascular tone", Trends Cardiovasc Med. Apr. 2012, vol. 22, No. 3, pp. 68-72. Especially abstract; p. 70, col. 1, para. 3.
Wang, et al., "Modulation of membrane channel currents by gap junction protein mimetic peptides: size matters", Am. J. Physiol. Cell Physiol. Sep. 2007, vol. 293, No. 3, pp. C1112-C1119. Especially abstract; p. C1113, col. 1, para. 7.
Q5VGQ7, UniProtKB Accession No. Q5VGQ7, Oct. 29, 2014 (online). (Retrieved on Apr. 22, 2016). Retrieved from the internet <URL: http://www.uniprot.org/uniprot/Q5VGQ7.txt?version=44<Entire document.
Billaud, et al., "A molecular signature in the pannexin1 intracellular loop confers channel activation by the alpha 1 adrenoreceptor in smooth muscle cells", Sci. Signal. (published online Feb. 17, 2015), vol. 8 No. 364, pp. ra17. Especially p. 5, Table 3; p. 5, col. 2, para 2: p. 8, col. 1, para 3.
A. W. Lohman, M. Billaud, B. E. Isakson, "Mechanisms of ATP release and signalling in the blood vessel wall" Cardiovasc Res 95, 269-280 (2012).
G. E. Sosinsky, D. Boassa, R. Dermietzel, H. S. Duffy, D. W. Laird, B. MacVicar, C. C. Naus, S. Penuela, E. Scemes, D. C. Spray, R. J. Thompson, H. B. Zhao, G. Dahl, "Pannexin channels are not gap junction hemichannels", Channels (Austin) 5, 193-197 (2011).
G. Spagnol, P. L. Sorgen, D. C. Spray, "Structural order in Pannexin 1 cytoplasmic domains", Channels 8, (2014).
S. Penuela, R. Bhalla, X. Q. Gong, K. N. Cowan, S. J. Celetti, B. J. Cowan, D. Bai, Q. Shao, D. W. Laird, "Pannexin 1 and pannexin 3 are glycoproteins that exhibit many distinct characteristics from the connexin family of gap junction proteins", Journal of cell science 120, 3772-3783 (2007).
A. W. Lohman, M. Billaud, A. C. Straub, S. R. Johnstone, A. K. Best, M. Lee, K. Barr, S. Penuela, D. W. Laird, B. E. Isakson, "Expression of pannexin isoforms in the systemic murine arterial network", Journal of vascular research 49, 405-416 (2012).
F. B. Chekeni, M. R. Elliott, J. K. Sandilos, S. F. Walk, J. M. Kinchen, E. R. Lazarowski, A. J. Armstrong, S. Penuela, D. W. Laird, G. S. Salvesen, B. E. Isakson, D. A. Bayliss, K. S. Ravichandran, "Pannexin 1 channels mediate 'find-me' signal release and membrane permeability during apoptosis", Nature 467, 863-867 (2010).
M. Sridharan, S. P. Adderley, E. A. Bowles, T. M. Egan, A. H. Stephenson, M. L. Ellsworth, R. S. Sprague, "Pannexin 1 is the conduit for low oxygen tension-induced ATP release from human erythrocytes", Am J Physiol Heart Circ Physiol 299, H1146-1152 (2010).
A. W. Lohman, B. E. Isakson, "Differentiating connexin hemichannels and pannexin channels in cellular ATP release", FEBS Lett 588, 1379-1388 (2014).
A. Tanoue, Y. Nasa, T. Koshimizu, H. Shinoura, S. Oshikawa, T. Kawai, S. Sunada, S. Takeo, G. Tsujimoto, "The alpha(1D)-adrenergic receptor directly regulates arterial blood pressure via vasoconstriction", J Clin Invest 109, 765-775 (2002).
W. F. Jackson, E. M. Boerman, E. J. Lange, S. S. Lundback, K. D. Cohen, "Smooth muscle alpha1D-adrenoceptors mediate phenylephrine-induced vasoconstriction and increases in endothelial cell Ca2+ in hamster cremaster arterioles", Br J Pharmacol 155, 514-524 (2008).
T. Kitazawa, K. Kitazawa, Size-dependent heterogeneity of contractile Ca2+ sensitization in rat arterial smooth muscle, The Journal of physiology 590, 5401-5423 (2012).
A. W. Moore, W. F. Jackson, S. S. Segal, "Regional heterogeneity of alpha-adrenoreceptor subtypes in arteriolar networks of mouse skeletal muscle", The Journal of physiology 588, 4261-4274 (2010).

\* cited by examiner

COMPOSITIONS AND METHODS FOR REGULATING BLOOD PRESSURE

CROSS REFERENCE TO RELATED APPLICATIONS

This application is a national stage filing of International Application No. PCT/US2016/017830, filed Feb. 12, 2016, which claims priority under 35 U.S.C. § 119(e) to U.S. Provisional Application Ser. No. 62/115,685 filed Feb. 13, 2015 and 62/198,480, filed Jul. 29, 2015, the disclosures of which are incorporated by reference in their entirety herein.

STATEMENT REGARDING FEDERALLY SPONSORED RESEARCH OR DEVELOPMENT

This invention was made with government support under Grant Nos. HL088554 and HL120840, awarded by The National Institutes of Health. The government has certain rights in the invention.

BACKGROUND

Purinergic signaling is central in the regulation of vascular tone, which can be mediated by adenosine 5' triphosphate (ATP) and its metabolic breakdown products. Interestingly, ATP can act as either a vasoconstrictor or vasodilator. In the vascular wall, there are multiple sources for ATP; for example, ATP can be released from perivascular nerves and endothelial cells, as well as from circulating erythrocytes. Previously, we showed that cultured smooth muscle cells (SMC) release ATP in response to phenylephrine, an α1-adrenoreceptor (α1AR) agonist, and that ATP, purinergic receptors, and the ATP-release channel formed by pannexin1 (Panx1) are synergistically involved in phenylephrine-mediated vasoconstriction.

The pannexins comprise a family of membrane channels similar to innexins, the gap junction-forming proteins in invertebrates. Pannexins share topological similarities but no sequence homology with the gap junction-forming connexin proteins in vertebrates, thus pannexins represent a distinct class of channel-forming proteins. Besides Panx1, two other isoforms have been described, Panx2 and Panx3. Panx1 is the most widely distributed in vertebrates, whereas the presence of Panx2 and Panx3 is restricted to specific tissues. In the systemic vasculature, Panx1 is found in all endothelial cells, but only some SMC; the protein is absent in SMC of conduit arteries and becomes more abundant as the resistance of the arteries increases. Functionally, in apoptotic cells Panx1 channels are activated for cell clearance to support the innate immune response, and in neurons, Panx1 channels are activated in response to cerebral ischemia or to decreases in circulating oxygen. Because Panx1 forms large-pore channels allowing the release of ATP and other intracellular ions and metabolites, channel activity is regulated by various receptors to avoid loss of cellular electrochemical and metabolic homeostasis, which would result in rapid cell death. For example, Panx1-dependent ATP release occurs in response to activation of thrombin receptors, N-methyl-D-aspartate (NMDA) receptors, histamine receptors, and purinergic receptors.

There is a long felt need in the art for compositions and methods useful for regulating blood pressure and for maintaining blood pressure homeostasis. The present invention satisfies these needs.

SUMMARY OF THE INVENTION

It is disclosed herein that pharmacological or molecular inhibition of pannexin 1 (Panx1) reduces α1-adrenoreceptor (α1AR)-dependent responses in isolated arteries and is also effective in vivo. It is also disclosed herein that: smooth muscle cell (SMC)-specific Panx1-knockout impairs circadian regulation of blood pressure; α1AR-stimulated vasoconstriction involves the intracellular loop of Panx1; α1AR-stimulated activation of the Panx1 channel involves an intracellular loop of Panx1; and a novel inhibitor of Panx1 is provided.

In one embodiment, the present invention provides compositions and methods useful for inhibiting vasoconstriction. In one aspect, the method inhibits vasoconstriction of resistance vasculature. In one aspect, the compositions and methods regulate blood pressure homeostasis. In one aspect, blood pressure is reduced. In one aspect, blood pressure is inhibited from increasing.

In one embodiment, the compositions and methods of the invention reduce blood pressure. In one aspect, the compositions and methods of the invention inhibit ATP release upon stimulation of α1AR.

In one embodiment, the present invention provides compositions and methods useful for inhibiting or reducing α1AR agonist-mediated vasoconstriction comprising contacting a blood vessel, wherein the blood vessel is susceptible to constriction by an α1AR agonist, with an effective amount of an inhibitor of the invention. In one aspect, the inhibitor is a peptide comprising SEQ ID NO:1. In one aspect, it further comprises SEQ ID NO:2. In another aspect, the peptide comprises SEQ ID NO:3.

In one embodiment, the present invention provides compositions and methods useful for inhibiting the activation of α1AR signaling. In one aspect, the present invention provides compositions and methods for inhibiting α1AR-mediated constriction of a blood vessel, the method comprising contacting the vessel with an effective amount of an inhibitor of pannexin 1 (Panx1), wherein the constriction requires α1AR-stimulated activation of Panx1. In one aspect, the inhibitor is a peptide against an intracellular loop of Panx1.

In one embodiment, the present invention provides compositions and methods for regulating the noradrenergic response.

In one embodiment, the present invention provides useful peptides for regulating α1AR signaling. In one aspect, the peptides are mimetics of sequences in Panx1. In one aspect, a peptide of the invention inhibits a functional interaction between Panx1 and α1AR. In one aspect, a peptide of the invention is an inhibitor of Panx1. In one aspect, the peptides have an additional TAT sequence. In one aspect, they do not.

In one embodiment, the present invention provides the novel peptide Intracellular Loop 2 (IL2), also referred to as UVAPx-1, a synthetic small-interfering peptide, which mimics an important regulatory region (KYPIVEQYLK) (SEQ ID NO:1) on the intracellular loop of both human (K192-K201) and murine (K191-K200) pannexin1 proteins. It is composed of a sequence of 19 amino acids (molecular weight=2510.1 g·mol-1), nine of which are a TAT consensus sequence. That is, it harbors a TAT (transactivator of transcription) consensus sequence on the peptide C-terminus (YGRKKQRRR) (SEQ ID NO:2), a derivative of the human immunodeficiency virus (HIV), which strongly potentiates peptide delivery across cellular membranes. The novel full-length IL2 peptide (KYPIVEQYLKYGRKKQRRR) (SEQ ID NO:3) is disclosed herein as a potent and specific inhibitor of pannexin1 channel activation and channel opening. This peptide is also referred to as PanX peptide and peptide against pannexin 1.

In one embodiment, the present invention provides for treating a subject in need thereof by administering an effective amount of a peptide of the invention. In one aspect, the peptide is IL2, or a biologically active fragment or homolog thereof. In one aspect, a pharmaceutical composition is administered to the subject, wherein the composition comprises an effective amount of the peptide and a pharmaceutically-acceptable carrier. In one aspect, administration of IL2 to a subject lowers blood pressure.

In one embodiment, the present invention provides compositions and methods to inhibit or reduce vasoconstriction comprising administering to a subject in need thereof an effective amount of a peptide having an amino acid sequence comprising KYPIVEQYLK (SEQ ID NO:1) and conservative amino acid substitutions thereof, said peptide further comprising a plasma membrane permeability sequence. In one aspect, the plasma membrane permeability sequence comprises a Human Immunodeficiency Virus (HIV)-tat tag sequence of YGRKKQRRR (SEQ ID NO:2). In one aspect, the method decreases blood pressure.

In one embodiment, the compositions and methods of the invention reduce vasoconstriction of resistance vasculature. In one aspect, the compositions and methods of the invention relax resistance arterioles.

As demonstrated herein, Panx1 can be inhibited by pharmacologic inhibitors as well as inhibitors to achieve the desired results as disclosed herein.

Sequences used herein include:
SEQ ID NO:1—KYPIVEQYLK- intracellular loop 2 (not to be confused with IL2 peptide)
SEQ ID NO:2—YGRKKQRRR- TAT sequence
SEQ ID NO:3—KYPIVEQYLKYGRKKQRRR- full-length IL2 (SEQ ID NOs: 1 and 2 combined)
SEQ ID NO:4—VGQSLWEISE- intracellular loop 1
SEQ ID NO:5—RRLKVYEILPTFDVLH- CT1
SEQ ID NO:6—IPTSLQTKGE- CT2—
SEQ ID NO:7—IYLYVEQKPY- scrambled intracellular loop 2

In one embodiment, the compositions and methods of the invention are useful for preventing or treating diseases, disorders, or conditions associated with aberrant α1AR signaling or pannexin1 activation. In one aspect, the compositions and methods are useful of inhibiting or reducing these events in smooth muscle cells.

In one embodiment, the compositions and methods of the invention are useful for treating diseases, disorders, and conditions. In one aspect, the compositions and methods are useful for regulating vasoconstriction and blood pressure. In one aspect, the disease, disorder, or condition is associated with increased vasoconstriction. In one aspect, the compositions and methods are useful for regulating vasoconstriction and blood pressure in a disease, disorder, and condition selected from the group consisting of hypertension, primary hypertension, treatment resistant hypertension, obesity-related hypertension, stroke, myocardial infarction, coronary artery disease, pulmonary arterial hypertension. In one aspect, the compositions and methods of the invention are useful for treating sickle cell disease, rheumatoid arthritis, bladder disorders, and intestinal peristalsis disorders. One of ordinary skill in the art will appreciate that, based on the disclosure provided herein using a peptide or other agent to regulate pannexin1, that other diseases, disorders, and conditions can be treated where pannexin1 is part of the signaling process.

The dosage of peptide used can vary depending on factors such as the disease, disorder or condition being treated, the age, sex, and health of the subject, etc. In one embodiment, a peptide of the invention is administered at a dosage ranging from about 1.0 milligrams (mg)/kilogram (kg) body weight to about 20.0 mg/kg body weight. This includes, for example, 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, and 20.0, as well as decimals and fragments thereof. In one aspect, a dosage of 5.0 mg/kg body weight is used. A dose can be administered more than once and can also be administered as a unit dose. The schedule and regimen can be determined by one of skill in the art.

Various aspects and embodiments of the invention are described in further detail below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1A:
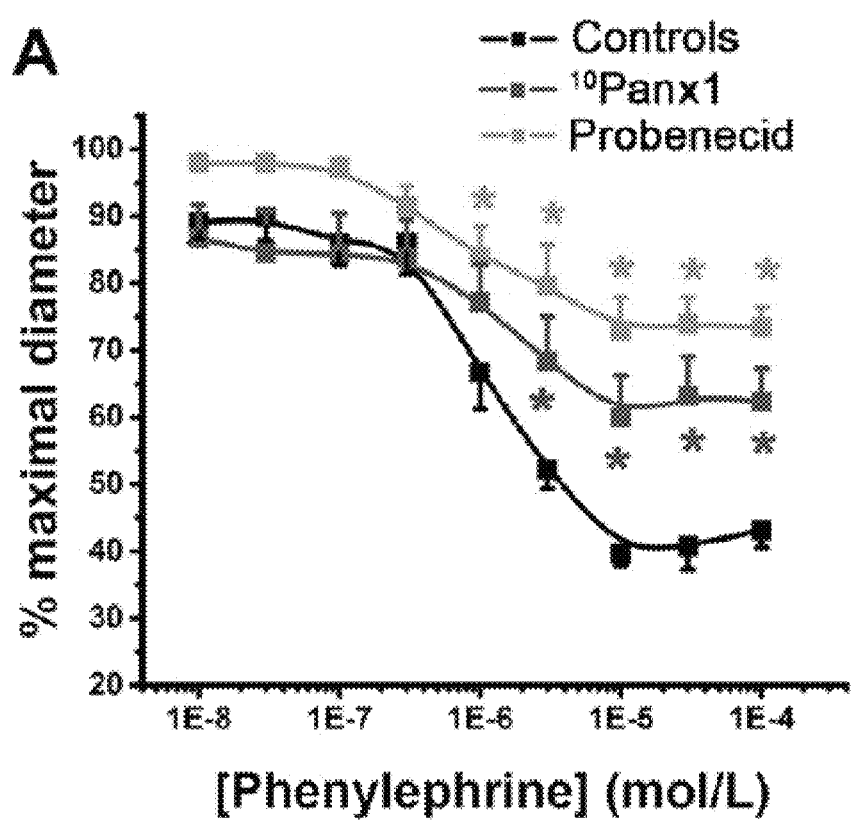
FIGS. 1 (A-E): Pharmacological inhibition of Pannexin 1 reduces vasoconstriction and ATP release selectively upon activation of α1AR. (1A-D) Effect of [10]Panx1 (300 μmol/L), and probenecid (2 mmol/L) on contractile response of pressurized TDAs stimulated with the indicated concentrations of agonists. n=5-7, * indicates p<0.05 compared to untreated response (black curves) using 2-way ANOVA. (1E) Relative ATP released from intact TDA in response to phenylephrine (PE) in the presence or absence of [10]Panx1 (300 μmol/L), serotonin (5-HT), and endothelin-1 (ET-1). Data are presented as a percent increase in ATP concentration from unstimulated conditions. The insert shows an image of a TDA in a well of a 96-well dish. n=5-11, * indicates p<0.05 compared to phenylephrine using a Kruskal-Wallis test.

Abbreviations and Acronyms
5HT—serotonin
α1AR—alpha 1-adrenoreceptor
α1DAR—α1D subtype of adrenoreceptor
AR—adrenoreceptor
CBX—carbenoxolone
CLP—Cecal ligation puncture
CT—C terminal tail
$EC_{50}$—concentration needed to produce 50% of the maximum effect
$E_{MAX}$—maximum effect
ET-1—endothelin 1
GPCR—G protein-coupled receptors
HEK—human embryonic kidney
IEL—internal elastic lamina
IL—intracellular loop
IL2 peptide—a peptide comprising a mimetic of intracellular loop 2 of pannexin 1 and a TAT sequence combined, forming SEQ ID NO:3. Also referred to as PanX peptide and UVAPX-1 peptide
KO—knockout
KOMP—knockout mouse project
MAP—mean arterial pressure
NMDA—N-methyl-D-aspartate
Panx1—pannexin 1
PAR—protease activated receptor
PE—phenylephrine
PKA—cyclic AMP-dependent protein kinase
PKC—protein kinase C
SMC—smooth muscle cell
TDA—thoracodorsal artery
WT—wild type
Definitions In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element or "a protein" means more than one protein.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. Therefore, about 50% means in the range of 45%-55%. Numerical ranges recited herein by endpoints include all numbers and fractions (where applicable) subsumed within that range (e.g. 1 to 5 includes 1, 1.5, 2, 2.75, 3, 3.90, 4, and 5). It is also to be understood that all numbers and fractions thereof are presumed to be modified by the term "about."

As used herein the term, "accurate mass" refers to an experimentally or theoretically determined mass of an ion that is used to determine an elemental formula. For ions containing combinations of the elements C, H, N, O, P, S, and the halogens, with mass less than 200 Unified Atomic Mass Units, a measurement about 5 ppm uncertainty is sufficient to uniquely determine the elemental composition.

The term "activation of Panx1" as used herein means stimulated opening of the pannexin1 channel wherein ATP is released.

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As used herein, the term "adjuvant" refers to a substance that elicits an enhanced immune response when used in combination with a specific antigen.

As use herein, the terms "administration of" and or "administering" a compound should be understood to mean providing a compound of the invention or a prodrug of a compound of the invention to a subject in need of treatment.

As used herein, the term "adrenergic" means relating to or denoting nerve cells in which epinephrine (adrenaline), norepinephrine (noradrenaline), or a similar substance acts as a neurotransmitter or to the effect of such. The adrenergic nervous system of part of the autonomic nervous system. An adrenergic agonist is a drug that stimulates a response from the adrenergic receptors. Antagonists are referred to as "alpha blockers".

As used herein, the term "aerosol" refers to suspension in the air. In particular, aerosol refers to the particlization or atomization of a formulation of the invention and its suspension in the air.

As used herein, an "agonist" is a composition of matter which, when administered to a mammal such as a human, enhances or extends a biological activity attributable to the level or presence of a target compound or molecule of interest in the mammal.

As used herein, "alleviating a disease or disorder symptom," means reducing the severity of the symptom or the frequency with which such a symptom is experienced by a patient, or both.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The term "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

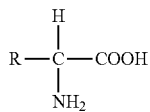

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

An "antagonist" is a composition of matter which when administered to a mammal such as a human, inhibits a biological activity attributable to the level or presence of a compound or molecule of interest in the mammal.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies.

An "antibody heavy chain," as used herein, refers to the larger of the two types of polypeptide chains present in all antibody molecules.

An "antibody light chain," as used herein, refers to the smaller of the two types of polypeptide chains present in all antibody molecules.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates.

The term "antigenic determinant" as used herein refers to that portion of an antigen that makes contact with a particular antibody (i.e., an epitope). When a protein or fragment of a protein, or chemical moiety is used to immunize a host animal, numerous regions of the antigen may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the invention include, but are not limited to, phosphorothioate oligonucleotides and other modifications of oligonucleotides.

An "aptamer" is a compound that is selected in vitro to bind preferentially to another compound (for example, the identified proteins herein). Often, aptamers are nucleic acids or peptides because random sequences can be readily generated from nucleotides or amino acids (both naturally occurring or synthetically made) in large numbers but of course they need not be limited to these.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

"Binding partner," as used herein, refers to a molecule capable of binding to another molecule.

The term "biocompatible", as used herein, refers to a material that does not elicit a substantial detrimental response in the host.

The term "biological sample," as used herein, refers to samples obtained from a subject, including, but not limited to, skin, hair, tissue, blood, plasma, cells, sweat and urine.

As used herein, the term "biologically active fragments" or "bioactive fragment" of the polypeptides encompasses natural or synthetic portions of the full-length protein that are capable of specific binding to their natural ligand or of performing the function of the protein.

As used herein, the term "carrier molecule" refers to any molecule that is chemically conjugated to the antigen of interest that enables an immune response resulting in antibodies specific to the native antigen.

The term "cell surface protein" means a protein found where at least part of the protein is exposed at the outer aspect of the cell membrane. Examples include growth factor receptors.

A "chaotropic agent" is a substance which disrupts the structure of, and denatures, macromolecules such as proteins and nucleic acids (e.g. DNA and RNA).

Chaotropic solutes increase the entropy of the system by interfering with intramolecular interactions mediated by non-covalent forces such as hydrogen bonds, van der Waals forces, and hydrophobic effects. Macromolecular structure and function is dependent on the net effect of these forces (see protein folding), therefore it follows that an increase in chaotropic solutes in a biological system will denature macromolecules, reduce enzymatic activity and induce stress on a cell (i.e., a cell will have to synthesize stress protectants). Tertiary protein folding is dependent on hydrophobic forces from amino acids throughout the sequence of the protein. Chaotropic solutes decrease the net hydrophobic effect of hydrophobic regions because of a disordering of water molecules adjacent to the protein. This solubilizes the hydrophobic region in the solution, thereby denaturing the protein. This is also directly applicable to the hydrophobic region in lipid bilayers; if a critical concentration of a chaotropic solute is reached (in the hydrophobic region of the bilayer) then membrane integrity will be compromised, and the cell will lyse. Chaotropic salts that dissociate in solution exert chaotropic effects via different mechanisms. Whereas chaotropic compounds such as ethanol interfere with non-covalent intramolecular forces as outlined above, salts can have chaotropic properties by shielding charges and preventing the stabilization of salt bridges. Hydrogen bonding is stronger in non-polar media, so salts, which increase the chemical polarity of the solvent, can also destabilize hydrogen bonding. Mechanistically this is because there are insufficient water molecules to effectively solvate the ions. This can result in ion-dipole interactions between the salts and hydrogen bonding species which are more favorable than normal hydrogen bonds. Chaotropic agents include butanol, ethanol, guanidinium chloride, lithium perchlorate, lithium acetate, magnesium chloride, phenol, propanol, sodium dodecyl sulfate, thiourea, and urea.

As used herein, the term "chemically conjugated," or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates or carboxylic acids, on the antigen and the carrier molecule. Chemical conjugation also includes non-covalent linkage between the antigen and the carrier molecule.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

The term "competitive sequence" refers to a peptide or a modification, fragment, derivative, or homolog thereof that competes with another peptide for its cognate binding site.

A "compound," as used herein, refers to any type of substance or agent that is commonly considered a drug, or a candidate for use as a drug, as well as combinations and mixtures of the above.

As used herein, the term "conservative amino acid substitution" is defined herein as an amino acid exchange within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;

III. Polar, positively charged residues:
His, Arg, Lys;
IV. Large, aliphatic, nonpolar residues:
Met Leu, Ile, Val, Cys
V. Large, aromatic residues:
Phe, Tyr, Trp A "control" cell is a cell having the same cell type as a test cell. The control cell may, for example, be examined at precisely or nearly the same time the test cell is examined. The control cell may also, for example, be examined at a time distant from the time at which the test cell is examined, and the results of the examination of the control cell may be recorded so that the recorded results may be compared with results obtained by examination of a test cell.

A "test" cell is a cell being examined.

"Cytokine," as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets and effector activities of these cytokines have been described.

As used herein, a "derivative" of a compound, when referring to a chemical compound, is one that may be produced from another compound of similar structure in one or more steps, as in replacement of H by an alkyl, acyl, or amino group.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

As used herein, the term "diagnosis" refers to detecting a disease, disorder or condition using a marker disclosed herein. In any method of diagnosis exist false positives and false negatives. Any one method of diagnosis does not provide 100% accuracy.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains.

As used herein, the term "effector domain" refers to a domain capable of directly interacting with an effector molecule, chemical, or structure in the cytoplasm which is capable of regulating a biochemical pathway.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

The term "elixir," as used herein, refers in general to a clear, sweetened, alcohol-containing, usually hydroalcoholic liquid containing flavoring substances and sometimes active medicinal agents.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "enhancer" is a DNA regulatory element that can increase the efficiency of transcription, regardless of the distance or orientation of the enhancer relative to the start site of transcription.

The term "epitope" as used herein is defined as small chemical groups on the antigen molecule that can elicit and react with an antibody. An antigen can have one or more epitopes. Most antigens have many epitopes; i.e., they are multivalent. In general, an epitope is roughly five amino acids or sugars in size. One skilled in the art understands that generally the overall three-dimensional structure, rather than the specific linear sequence of the molecule, is the main criterion of antigenic specificity.

By "equivalent fragment" as used herein when referring to two homologous proteins from different species is meant a fragment comprising the domain or amino acid being described or compared relative to the first protein.

As used herein, an "essentially pure" preparation of a particular protein or peptide is a preparation wherein at least about 95%, and preferably at least about 99%, by weight, of the protein or peptide in the preparation is the particular protein or peptide.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, the term "fragment," as applied to a protein or peptide, can ordinarily be at least about 2-15 amino acids in length, at least about 15-25 amino acids, at least about 25-50 amino acids in length, at least about 50-75 amino acids in length, at least about 75-100 amino acids in length, and greater than 100 amino acids in length, depending on the particular protein or peptide being referred to.

As used herein, a "functional" molecule is a molecule in a form in which it exhibits a property or activity by which it is characterized. A functional enzyme, for example, is one that exhibits the characteristic catalytic activity by which the enzyme is characterized.

"Highly chaotropic environment" refers the concentration of a chaotropic agent in a solution. In certain embodiments, the concentration is exactly, about or at least, 1, 2, 3, 4, 5, 6, 7, 8, 9, 10, or more molar. In a particular embodiment it refers to about or at least 6, 7, 8 or 9 molar urea.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity." The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used. The percent identity between two sequences can be determined using techniques similar to those described above, with or without allowing gaps. In calculating percent identity, typically exact matches are counted.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

As used herein, the term "hydrolyzing agent" refers to any one or combination of a large number of different enzymes, including but not limited to trypsin, Lysine-C endopeptidase (LysC), arginine-C endopeptidase (ArgC), Asp-N, glutamic acid endopeptidase (GluC) and chymotrypsin, V8 protease and the like, as well as chemicals, such as cyanogen bromide. In the subject invention one or a combination of hydrolyzing agents cleave peptide bonds in a protein or polypeptide, in a sequence-specific manner, generating a predictable collection of shorter peptides (a "digest"). A portion of the biological samples are contacted with hydrolyzing agent(s) to form a digest of the biological sample. Given that the amino acid sequences of certain polypeptides and proteins in biological samples are often known and that the hydrolyzing agent(s) cuts in a sequence-specific manner, the shorter peptides in the digest are generally of a predicable amino acid sequence. The term "inhibit," as used herein, refers to the ability of a compound, agent, or method to reduce or impede a described function, level, activity, rate, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block."

The term "inhibit a complex," as used herein, refers to inhibiting the formation of a complex or interaction of two or more proteins, as well as inhibiting the function or activity of the complex. The term also encompasses disrupting a formed complex. However, the term does not imply that each and every one of these functions must be inhibited at the same time.

The term "inhibit a protein," as used herein, refers to any method or technique which inhibits protein synthesis, levels, activity, or function, as well as methods of inhibiting the induction or stimulation of synthesis, levels, activity, or function of the protein of interest. The term also refers to any metabolic or regulatory pathway which can regulate the synthesis, levels, activity, or function of the protein of interest. The term includes binding with other molecules and complex formation. Therefore, the term "protein inhibitor" refers to any agent or compound, the application of which results in the inhibition of protein function or protein pathway function. However, the term does not imply that each and every one of these functions must be inhibited at the same time.

The term "inhibition of pannexin 1" means inhibition of activation/activity of the pannexin1 channel, including inhibiting stimulated opening of the channel. "Inhibition of pannexin1 activity" includes inhibiting opening of the channel and downstream signaling of pannexin1.

The term "inhibitor of pannexin 1" refers to inhibiting activity of pannexin 1, including activation/opening of the pannexin 1 channel.

As used herein "injecting or applying" includes administration of a compound of the invention by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

As used herein, an "instructional material" includes a publication, a recording, a diagram, or any other medium of expression which can be used to communicate the usefulness of the compositions and apparatuses of the invention in the kit. The instructional material of the kit of the invention may, for example, be affixed to a container which contains the identified compound(s) invention or be shipped together with a container which contains the identified compound. Alternatively, the instructional material may be shipped separately from the container with the intention that the instructional material and the compound be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

A "ligand" is a compound that specifically binds to a target receptor.

A "receptor" is a compound that specifically binds to a ligand.

A ligand or a receptor (e.g., an antibody) "specifically binds to" or "is specifically immunoreactive with" a compound when the ligand or receptor functions in a binding reaction which is determinative of the presence of the compound in a sample of heterogeneous compounds. Thus, under designated assay (e.g., immunoassay) conditions, the ligand or receptor binds preferentially to a particular compound and does not bind in a significant amount to other compounds present in the sample. For example, a polynucleotide specifically binds under hybridization conditions to a compound polynucleotide comprising a complementary sequence; an antibody specifically binds under immunoassay conditions to an antigen bearing an epitope against which the antibody was raised. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988, Antibodies, A Laboratory Manual, Cold Spring Harbor Publications, New York) for a description of immunoassay formats and conditions that can be used to determine specific immunoreactivity.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions.

"Liquid chromatography-mass spectrometry (LC-MS, or alternatively HPLC-MS)" is an analytical chemistry technique that combines the physical separation capabilities of liquid chromatography (or HPLC) with the mass analysis capabilities of mass spectrometry (MS). Liquid chromatography generally utilizes very small particles packed and operating at relatively high pressure, and is referred to as high performance liquid chromatography (HPLC). LC-MS methods use HPLC instrumentation for sample introduction. In HPLC, the sample is forced by a liquid at high pressure (the mobile phase) through a column that is packed with a stationary phase generally composed of irregularly or spherically shaped particles chosen or derivatized to accomplish particular types of separations. HPLC methods are historically divided into two different sub-classes based on stationary phases and the corresponding required polarity of the mobile phase. Use of octadecylsilyl (C18) and related organic-modified particles as stationary phase with pure or pH-adjusted water-organic mixtures such as water-acetonitrile and water-methanol are used in techniques termed reversed phase liquid chromatography (RP-LC). Use of materials such as silica gel as stationary phase with neat or mixed organic mixtures are used in techniques termed normal phase liquid chromatography (NP-LC).

"Malexpression" of a gene means expression of a gene in a cell of a patient afflicted with a disease or disorder, wherein the level of expression (including non-expression), the portion of the gene expressed, or the timing of the expression of the gene with regard to the cell cycle, differs from expression of the same gene in a cell of a patient not afflicted with the disease or disorder. It is understood that malexpression may cause or contribute to the disease or disorder, be a symptom of the disease or disorder, or both.

The term "mass spectrometer" means a device capable of detecting specific molecular species and measuring their accurate masses. The term is meant to include any molecular detector into which a polypeptide or peptide may be eluted for detection and/or characterization. In the preferred MS procedure, a sample, e.g., the elution solution, is loaded onto the MS instrument, and undergoes vaporization. The components of the sample are ionized by one of a variety of methods (e.g., by electrospray ionization or "ESI"), which results in the formation of positively charged particles (ions). The positive ions are then accelerated by a magnetic field. The computation of the mass-to-charge ratio of the particles is based on the details of motion of the ions as they transit through electromagnetic fields, and detection of the ions. In one aspect, the mass measurement error of a mass spectrometer of the invention is about 10 ppm or less, in another it is about 7 ppm or less, and in yet another it is about 5 ppm or less. Fragment ions in the MS/MS and MS3 spectra are generally highly specific for peptides of interest.

The term "measuring the level of expression" or "determining the level of expression" as used herein refers to any measure or assay which can be used to correlate the results of the assay with the level of expression of a gene or protein of interest. Such assays include measuring the level of mRNA, protein levels, etc. and can be performed by assays such as northern and western blot analyses, binding assays, immunoblots, etc. The level of expression can include rates of expression and can be measured in terms of the actual amount of an mRNA or protein present. Such assays are coupled with processes or systems to store and process information and to help quantify levels, signals, etc. and to digitize the information for use in comparing levels.

The term "nasal administration" in all its grammatical forms refers to administration of at least one compound of the invention through the nasal mucous membrane to the bloodstream for systemic delivery of at least one compound of the invention. The advantages of nasal administration for delivery are that it does not require injection using a syringe and needle, it avoids necrosis that can accompany intramuscular administration of drugs, and trans-mucosal administration of a drug is highly amenable to self administration.

The term "nucleic acid" typically refers to large polynucleotides. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "nucleic acid construct," as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "peptide" typically refers to short polypeptides.

The term "per application" as used herein refers to administration of a compositions, drug, or compound to a subject.

As used herein, the term "pharmaceutically-acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Pharmaceutically acceptable" means physiologically tolerable, for either human or veterinary application.

As used herein, "pharmaceutical compositions" include formulations for human and veterinary use.

"Plurality" means at least two.

A "polynucleotide" means a single strand or parallel and anti-parallel strands of a nucleic acid. Thus, a polynucleotide may be either a single-stranded or a double-stranded nucleic acid.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" means a non-naturally occurring peptide or polypeptide. Synthetic peptides or polypeptides can be synthesized, for example, using an automated polypeptide synthesizer. Various solid phase peptide synthesis methods are known to those of skill in the art.

By "presensitization" is meant pre-administration of at least one innate immune system stimulator prior to challenge with an agent. This is sometimes referred to as induction of tolerance.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

A "prophylactic" treatment is a treatment administered to a subject who does not exhibit signs of a disease or exhibits only early signs of the disease for the purpose of decreasing the risk of developing pathology associated with the disease.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides, vol.* 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

As used herein, "purinergic signaling" is a form of extracellular signalling mediated by purine nucleotides and nucleosides such as adenosine and ATP.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

A "recombinant cell" is a cell that comprises a transgene. Such a cell may be a eukaryotic or a prokaryotic cell. Also, the transgenic cell encompasses, but is not limited to, an embryonic stem cell comprising the transgene, a cell obtained from a chimeric mammal derived from a transgenic embryonic stem cell where the cell comprises the transgene, a cell obtained from a transgenic mammal, or fetal or placental tissue thereof, and a prokaryotic cell comprising the transgene.

The term "regulate" refers to either stimulating or inhibiting a function or activity of interest.

As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding the chromogenic substrate o-nitrophenyl-β-galactoside to the medium (Gerhardt et al., eds., 1994, *Methods for General and Molecular Bacteriology*, American Society for Microbiology, Washington, D.C., p. 574).

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture. By the term "signal sequence" is meant a polynucleotide sequence which encodes a peptide that directs the path a polypeptide takes within a cell, i.e., it directs the cellular processing of a polypeptide in a cell, including, but not limited to, eventual secretion of a polypeptide from a cell. A signal sequence is a sequence of amino acids which are typically, but not exclusively, found at the amino terminus of a polypeptide which targets the synthesis of the polypeptide to the endoplasmic reticulum. In some instances, the signal peptide is proteolytically removed from the polypeptide and is thus absent from the mature protein.

By "small interfering RNAs (siRNAs)" is meant, inter alia, an isolated dsRNA molecule comprised of both a sense and an anti-sense strand. In one aspect, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

As used herein, the term "solid support" relates to a solvent insoluble substrate that is capable of forming linkages (preferably covalent bonds) with various compounds. The support can be either biological in nature, such as, without limitation, a cell or bacteriophage particle, or synthetic, such as, without limitation, an acrylamide derivative, agarose, cellulose, nylon, silica, or magnetized particles.

By the term "specifically binds to", as used herein, is meant when a compound or ligand functions in a binding reaction or assay conditions which is determinative of the presence of the compound in a sample of heterogeneous compounds.

The term "standard," as used herein, refers to something used for comparison. For example, a standard can be a known standard agent or compound which is administered or added to a control sample and used for comparing results when measuring said compound in a test sample. In one aspect, the standard compound is added or prepared at an amount or concentration that is equivalent to a normal value for that compound in a normal subject. Standard can also refer to an "internal standard," such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "subject" of analysis, diagnosis, or treatment is an animal. Such animals include mammals, preferably a human.

As used herein, a "subject in need thereof" is a patient, animal, mammal, or human, who will benefit from the method of this invention.

As used herein, a "substantially homologous amino acid sequence" includes those amino acid sequences which have at least about 95% homology, preferably at least about 96% homology, more preferably at least about 97% homology, even more preferably at least about 98% homology, and most preferably at least about 99% homology to an amino acid sequence of a reference sequence. Amino acid sequences similarity or identity can be computed using, for example, the BLASTP and TBLASTN programs which employ the BLAST (basic local alignment search tool) algorithm. The default setting used for these programs are suitable for identifying substantially similar amino acid sequences for purposes of the present invention.

"Substantially identical" when referring to a subject protein or polypeptide relative to a reference protein or polypeptide (e.g., an enzyme such as aspergillopepsin I or a enzymatically active fragment thereof) means that the subject is either exactly, at least or about 99.9, 99.5, 99, 98, 97, 96, 95, 94, 93, 92, 91, 90, 89, 88, 87, 86, 85, 84, 83, 82, 81, 80, 75, 70, 65 or 60 percent identical in terms of amino acid sequence relative to the reference.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the term "transgene" means an exogenous nucleic acid sequence comprising a nucleic acid which encodes a promoter/regulatory sequence operably linked to nucleic acid which encodes an amino acid sequence, which exogenous nucleic acid is encoded by a transgenic mammal.

As used herein, the term "transgenic mammal" means a mammal, the germ cells of which comprise an exogenous nucleic acid.

As used herein, a "transgenic cell" is any cell that comprises a nucleic acid sequence that has been introduced into the cell in a manner that allows expression of a gene encoded by the introduced nucleic acid sequence.

The term to "treat," as used herein, means reducing the frequency with which symptoms are experienced by a patient or subject or administering an agent or compound to reduce the frequency with which symptoms are experienced.

A "prophylactic" treatment is a treatment administered to a subject who does not exhibit signs of a disease or exhibits only early signs of the disease for the purpose of decreasing the risk of developing pathology associated with the disease.

By the term "vaccine," as used herein, is meant a composition which when inoculated into a subject has the effect of stimulating an immune response in the subject, which serves to fully or partially protect the subject against a condition, disease or its symptoms. In one aspect, the condition is conception. The term vaccine encompasses prophylactic as well as therapeutic vaccines. A combination vaccine is one which combines two or more vaccines, or two or more compounds or agents.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

Embodiments

Multiple techniques for measuring proteins and peptides are known in the art or described herein and can use in the practice of the invention. These include, but are not limited to, for example:

Electrochemiluminescent immunoassay;

Bioluminsescent Immunoassay (for example, with use of apoaequorin and oelenterazine);

Luminescent oxygen channeling immunoassay (LOCI);

The Erenna Immunoassay System (a modified microparticle-based sandwich immunoassay with single-molecule counting);

Nanoparticle Immunoassay: nano-particles, spheres, or tubes as solid phases
  upconverting phosphor nanoparticle using antiStokes shift
  quantum dot immunoassay (Heterogeneous immunoassay in which a nanometer-sized (less than 10 nm) semiconductor quantum dot is used as a label. A quantum dot is a highly fluorescent nanocrystal composed of CdSe, CdS, ZnSe, InP, or InAs or a layer of ZnS or CdS on, for example, a CdSe core);

Fluorescence Excitation Transfer Immunoassay;

ImmunoPCR Immunoassay;

Solid Phase, Light-Scattering Immunoassay: Indium spheres are coated on glass to measure an antibody binding to an antigen. Binding of antibodies to antigens increases dielectric layer thickness, which produces a greater degree of scatter than in areas where only an antigen is bound. Quantitation is achieved by densitometry; and Surface Effect Immunoassay: with antibody immobilized on the surface of a waveguide (a quartz, glass, or plastic slide, or a gold- or silver-coated prism), and binding of antigen measured directly by total internal reflection fluorescence, surface plasmon resonance, or attenuated total reflection.

In one aspect, an antibody or a fragment or homolog thereof of the invention can be conjugated to an imaging agent. In one embodiment, antibody complex comprises an imaging agent selected from the group consisting of a radionuclide, a radiological contrast agent, a paramagnetic ion, a metal, a biological tag, a fluorescent label, a chemiluminescent label, an ultrasound contrast agent and a photoactive agent. In one aspect, the imaging agent is a radionuclide. In one aspect, the radionuclide is selected from the group consisting of $^{110}$In, $^{111}$In, $^{177}$Lu, $^{18}$F, $^{52}$Fe, $^{62}$Cu, $^{64}$C, $^{67}$C, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82}$mRb, $^{83}$Sr, and other gamma-, beta-, or positron-emitters. In one aspect, the radionuclide is $^{111}$In.

The invention further provides for use of the monoclonal antibodies described herein for drug delivery and for diagnostics. For example, various agents as described herein can be conjugated to the antibodies. Drugs such as calicheamicin, peptides such as D(KLAKLAK)$^2$, and radionuclides such as beta $^{90}$Y, gamma $^{131}$I, and positron $^{124}$I emitters can be conjugated to monoclonal antibodies to human protein and used to image cells and tissues.

It will be appreciated, of course, that the proteins or peptides of the invention may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—NH$_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double-stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, OLIGONUCLEOTIDE SYNTHESIS: A PRACTICAL APPROACH (IRL Press, Oxford, England)). RNAs may be produce in high yield via in vitro transcription using plasmids such as SP65 (Promega Corporation, Madison, Wis.).

The peptides of the present invention may be readily prepared by standard, well-established techniques, such as solid-phase peptide synthesis (SPPS) as described by Stewart et al. in *Solid Phase Peptide Synthesis*, 2nd Edition, 1984, Pierce Chemical Company, Rockford, Ill.; and as described by Bodanszky and Bodanszky in *The Practice of Peptide Synthesis*, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the $\alpha$-amino group of the amino acid, and on any side chain functional groups. Side chain protecting groups are generally stable to the solvents, reagents and reaction conditions used throughout the synthesis, and are removable under conditions that will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method that utilized tert-butyloxcarbonyl as the $\alpha$-amino protecting group, and the FMOC method which utilizes 9-fluorenylmethyloxcarbonyl to protect the $\alpha$-amino of the amino acid residues, both methods of which are well-known by those of skill in the art.

To ensure that the proteins or peptides obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer.

Protein sequenators, which sequentially degrade the peptide and identify the amino acids in order, may also be used to determine definitely the sequence of the peptide.

Prior to its use, the peptide can be purified to remove contaminants. In this regard, it will be appreciated that the peptide will be purified to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Substantially pure peptide obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

Pharmaceutical Compositions and Administration

The present invention is also directed to pharmaceutical compositions comprising the compounds of the present invention. More particularly, such compounds can be formulated as pharmaceutical compositions using standard pharmaceutically acceptable carriers, fillers, solubilizing agents and stabilizers known to those skilled in the art.

The invention is also directed to methods of administering the compounds of the invention to a subject. In one embodiment, the invention provides a method of treating a subject by administering compounds identified using the methods of the invention description. Pharmaceutical compositions comprising the present compounds are administered to a subject in need thereof by any number of routes including, but not limited to, topical, oral, intravenous, intramuscular, intra-arterial, intramedullary, intrathecal, intraventricular, transdermal, subcutaneous, intraperitoneal, intranasal, enteral, topical, sublingual, or rectal means.

In accordance with one embodiment, a method of treating a subject in need of such treatment is provided. The method comprises administering a pharmaceutical composition comprising at least one compound of the present invention to a subject in need thereof. Compounds identified by the methods of the invention can be administered with known compounds or other medications as well.

The invention also encompasses the use of pharmaceutical compositions of an appropriate compound, and homologs, fragments, analogs, or derivatives thereof to practice the methods of the invention, the composition comprising at least one appropriate compound, and homolog, fragment, analog, or derivative thereof and a pharmaceutically-acceptable carrier.

The pharmaceutical compositions useful for practicing the invention may be administered to deliver a dose of between 1 ng/kg/day and 100 mg/kg/day.

The invention encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

It will be understood by the skilled artisan that such pharmaceutical compositions are generally suitable for administration to animals of all sorts. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys. The invention is also contemplated for use in contraception for nuisance animals such as rodents.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

Typically, dosages of the compound of the invention which may be administered to an animal, preferably a human, range in amount from 1 μg to about 100 g per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the condition or disease being treated, the type and age of the animal, etc.

Suitable preparations of vaccines include injectables, either as liquid solutions or suspensions, however, solid forms suitable for solution in, suspension in, liquid prior to injection, may also be prepared. The preparation may also be emulsified, or the polypeptides encapsulated in liposomes. The active immunogenic ingredients are often mixed with excipients which are pharmaceutically acceptable and compatible with the active ingredient. Suitable excipients are, for example, water saline, dextrose, glycerol, ethanol, or the like and combinations thereof. In addition, if desired, the vaccine preparation may also include minor amounts of auxiliary substances such as wetting or emulsifying agents, pH buffering agents, and/or adjuvants which enhance the effectiveness of the vaccine.

The invention is also directed to methods of administering the compounds of the invention to a subject. In one embodiment, the invention provides a method of treating a subject by administering compounds identified using the methods of the invention. Pharmaceutical compositions comprising the present compounds are administered to an individual in need thereof by any number of routes including, but not limited to, topical, oral, intravenous, intramuscular, intra arterial, intramedullary, intrathecal, intraventricular, transdermal, subcutaneous, intraperitoneal, intranasal, enteral, topical, sublingual, or rectal means.

Peptide Modification and Preparation

Peptide preparation is described in the Examples. It will be appreciated, of course, that the proteins or peptides of the invention may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring or non-standard synthetic amino acids. The peptides of the invention are not limited to products of any of the specific exemplary processes listed herein.

The invention includes the use of beta-alanine (also referred to as β-alanine, β-Ala, bA, and βA, having the structure:

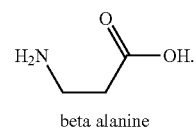

beta alanine

Sequences are provided herein which use the symbol "βA", but in the Sequence Listing submitted herewith "βA" is provided as "Xaa" and reference in the text of the Sequence Listing indicates that Xaa is beta alanine.

Peptides useful in the present invention, such as standards, or modifications for analysis, may be readily prepared by standard, well-established techniques, such as solid-phase peptide synthesis (SPPS) as described by Stewart et al. in *Solid Phase Peptide Synthesis,* 2nd Edition, 1984, Pierce Chemical Company, Rockford, Ill.; and as described by Bodanszky and Bodanszky in *The Practice of Peptide Synthesis,* 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method which utilized tert-butyloxcarbonyl as the α-amino protecting group, and the FMOC method which utilizes 9-fluorenylmethyloxcarbonyl to protect the α-amino of the amino acid residues, both methods of which are well-known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide may be purified to remove contaminants. In this regard, it will be appreciated that the peptide will be purified so as to meet the standards set out by the appropriate regulatory agencies. Any one of a number of conventional purification procedures may be used to attain the required level of purity including, for example, reversed-phase high performance liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

As discussed, modifications or optimizations of peptide ligands of the invention are within the scope of the application. Modified or optimized peptides are included within the definition of peptide binding ligand. Specifically, a peptide sequence identified can be modified to optimize its potency, pharmacokinetic behavior, stability and/or other biological, physical and chemical properties.

Amino Acid Substitutions

In certain embodiments, the disclosed methods and compositions may involve preparing peptides with one or more substituted amino acid residues.

In various embodiments, the structural, physical and/or therapeutic characteristics of peptide sequences may be optimized by replacing one or more amino acid residues.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

The skilled artisan will be aware that, in general, amino acid substitutions in a peptide typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, one can make the following isosteric and/or conservative amino acid changes in the parent polypeptide sequence with the expectation that the resulting polypeptides would have a similar or improved profile of the properties described above:

Substitution of alkyl-substituted hydrophobic amino acids: including alanine, leucine, isoleucine, valine, norleucine, S-2-aminobutyric acid, S-cyclohexylalanine or other simple alpha-amino acids substituted by an aliphatic side chain from C1-10 carbons including branched, cyclic and straight chain alkyl, alkenyl or alkynyl substitutions.

Substitution of aromatic-substituted hydrophobic amino acids: including phenylalanine, tryptophan, tyrosine, biphenylalanine, 1-naphthylalanine, 2-naphthylalanine, 2-benzothienylalanine, 3-benzothienylalanine, histidine, amino, alkylamino, dialkylamino, aza, halogenated (fluoro, chloro, bromo, or iodo) or alkoxy-substituted forms of the previous listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2,3, or 4-biphenylalanine, 2',-3',- or 4'-methyl-2, 3 or 4-biphenylalanine, and 2- or 3-pyridylalanine.

Substitution of amino acids containing basic functions: including arginine, lysine, histidine, ornithine, 2,3-diaminopropionic acid, homoarginine, alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha methyl arginine, alpha methyl 2,3-diaminopropionic acid, alpha methyl histidine, alpha methyl ornithine where alkyl group occupies the pro-R position of the alpha carbon. Also included are the amides formed from alkyl, aromatic, heteroaromatic (where the heteroaromatic group has one or more nitrogens, oxygens, or sulfur atoms singly or in combination) carboxylic acids or any of the many well-known activated derivatives such as acid chlorides, active esters, active azolides and related derivatives) and lysine, ornithine, or 2,3-diaminopropionic acid.

Substitution of acidic amino acids: including aspartic acid, glutamic acid, homoglutamic acid, tyrosine, alkyl, aryl, arylalkyl, and heteroaryl sulfonamides of 2,4-diaminopropionic acid, ornithine or lysine and tetrazole-substituted alkyl amino acids.

Substitution of side chain amide residues: including asparagine, glutamine, and alkyl or aromatic substituted derivatives of asparagine or glutamine.

Substitution of hydroxyl containing amino acids: including serine, threonine, homoserine, 2,3-diaminopropionic acid, and alkyl or aromatic substituted derivatives of serine or threonine. It is also understood that the amino acids within each of the categories listed above can be substituted for another of the same group.

For example, the hydropathic index of amino acids may be considered (Kyte & Doolittle, 1982, J. Mol. Biol., 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within +/−2 is preferred, within +/−1 are more preferred, and within +/−0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL Rockefeller University website). For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded peptide sequence are well known and a matter of routine experimentation for the skilled artisan, for example by the technique of site-directed mutagenesis or by synthesis and assembly of oligonucleotides encoding an amino acid substitution and splicing into an expression vector construct.

The invention also includes a kit comprising the composition of the invention and an instructional material which describes adventitially administering the composition to a cell or a tissue of a mammal. In another embodiment, this kit comprises a (preferably sterile) solvent suitable for dissolving or suspending the composition of the invention prior to administering the compound to the mammal.

EXAMPLES

Here, we examined Panx1 opening in response to α1AR activation in intact arteries using pharmacological blockers and an inducible SMC-specific Panx1-knockout mouse. We investigated the mechanisms downstream of α1AR stimulation leading to activation of Panx1 channels using a heterologous system expressing both Panx1 channels and the α1D subtype of AR (α1D-AR). Using peptides analogous to different intracellular regions of Panx1 amino acid sequence, as well as specific Panx1 mutants, we identified a region required for Panx1 activation by α1AR stimulation. These findings suggest that Panx1 channels are opened downstream of α1AR, potentiating vasoconstriction by a mechanism dependent on a discrete intracellular loop region of the channel. Our data provide new insights into the molecular mechanisms that control vascular tone and blood pressure and physiological Panx1 opening.

Materials and Methods

Animals

Figure 6A:
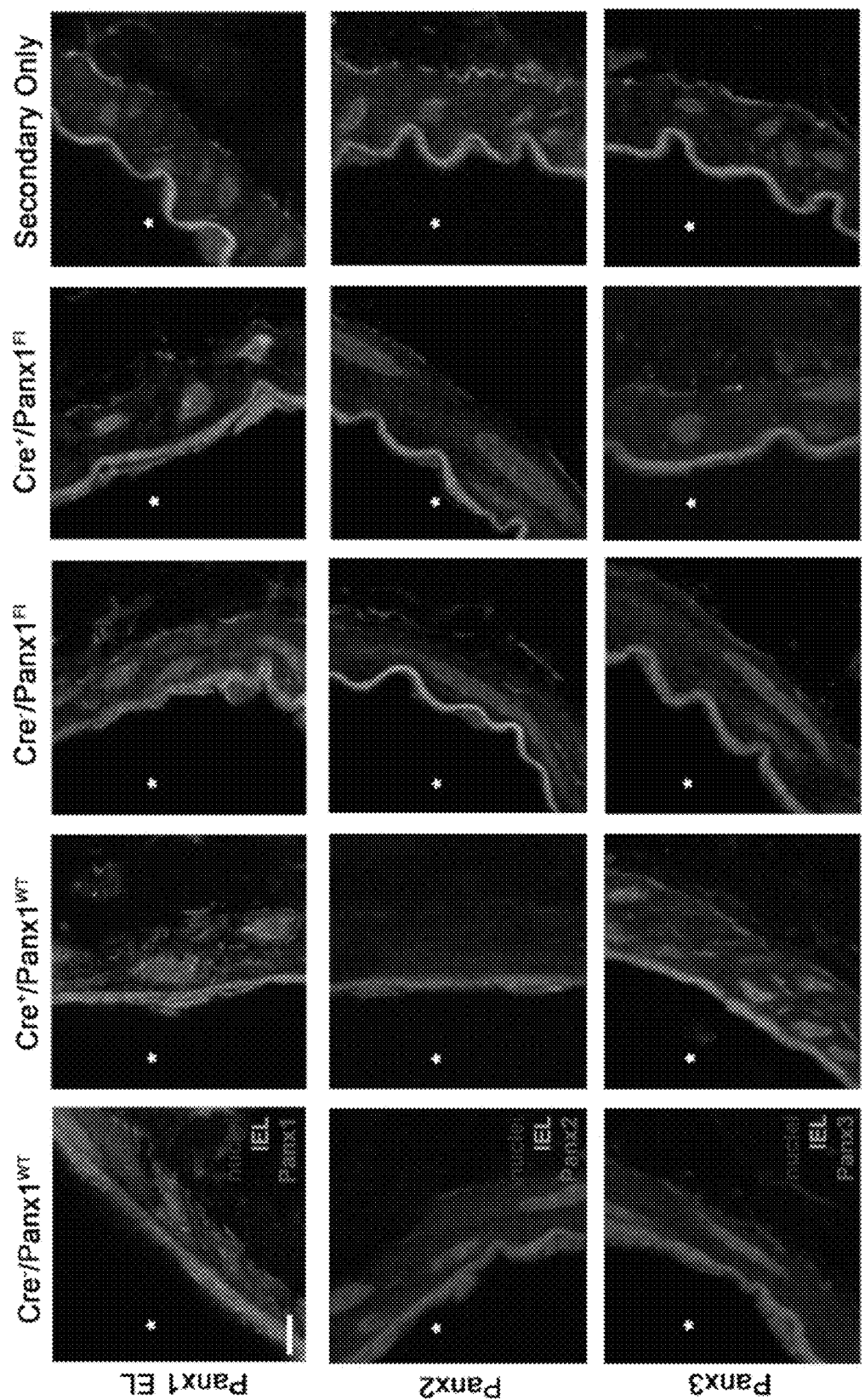
FIG. 6 (comprising A-E) Effect of SMC deletion of Panx1 on Panx2 and Panx3 abundance, ATP content, α1D adrenoreceptor abundance, and phenylephrine-induced contraction of aortic rings. (6A-15 micrographs) Representative immunofluorescent labeling using an antibody directed against the extracellular loop of Panx1 (top row, red), against Panx2 (red, middle row), and against Panx3 (red, lower row) on cross sections of thoracodorsal arteries (TDAs) isolated from Cre$^-$/Panx1$^{WT}$ mice, Cre$^-$/Panx1$^{F1}$ mice, Cre$^+$/Panx1$^{WT}$ mice, and Cre$^+$/Panx1$^{F1}$ all injected with tamoxifen for ten days. The right panel shows a negative control with the secondary antibody only on a cross section of a thoracodorsal artery isolated from Cre$^-$/Panx1$^{WT}$ mice. The autofluorescence of the internal elastic lamina appears in green, and the nuclei were labelled with DAPI (blue). * indicates the lumen. Scale bar=10 μm. (6B) Representative Western blot of isolated TDAs showing the abundance of Panx1 in Cre$^+$/Panx1$^{F1}$ (top panel), or the abundance of α1DAR in Cre/Panx1$^{WT}$ mice, Cre$^-$/Panx1$^{F1}$ mice, Cre$^+$/Panx1$^{WT}$ mice, and Cre$^+$/Panx1$^{F1}$ all injected with tamoxifen for ten days (middle panel). Lower panel shows tubulin as a loading control. (6C) Histogram of total ATP content measured in TDAs from C57Bl/6 (black) and Cre$^+$/Panx1$^{F1}$ (green). (6D) The contractile response of aortic rings isolated from control Cre$^+$/Panx1$^{F1}$ (injected with peanut oil, black curve), or isolated from Cre$^+$/Panx1$^{F1}$ injected with tamoxifen for ten days (green curve) in response to cumulative concentrations of phenylephrine. n=12-13 rings (6 mice in each group). (6E, three images) Representative images of TDAs isolated from a Cre$^+$/tdTomato$^+$ mouse showing the presence of dsRed only in the SMCs. Endothelial cells were labeled with isolectine and the nuclei are shown in blue. Scale bar=20 um.
Figure 6B:
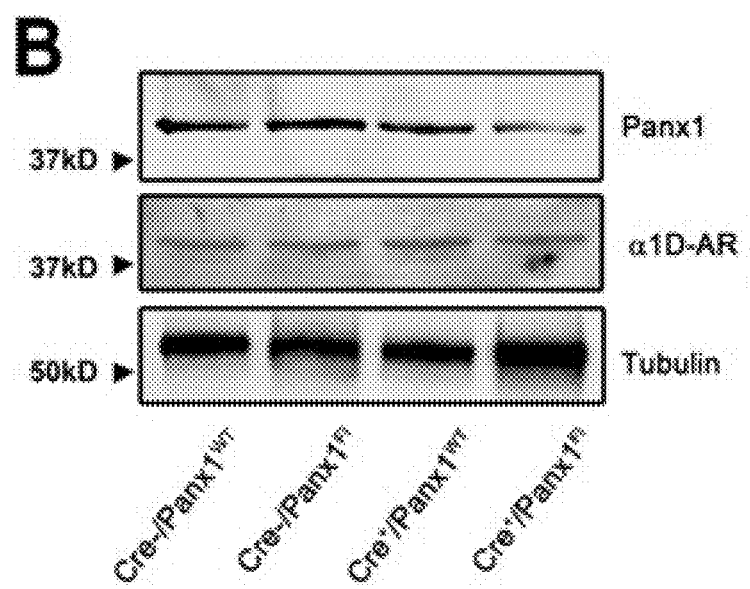
Figure 6C:
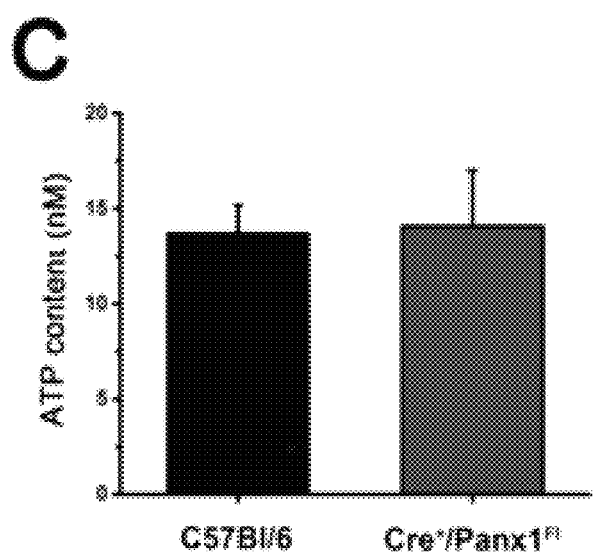
Figure 6D:
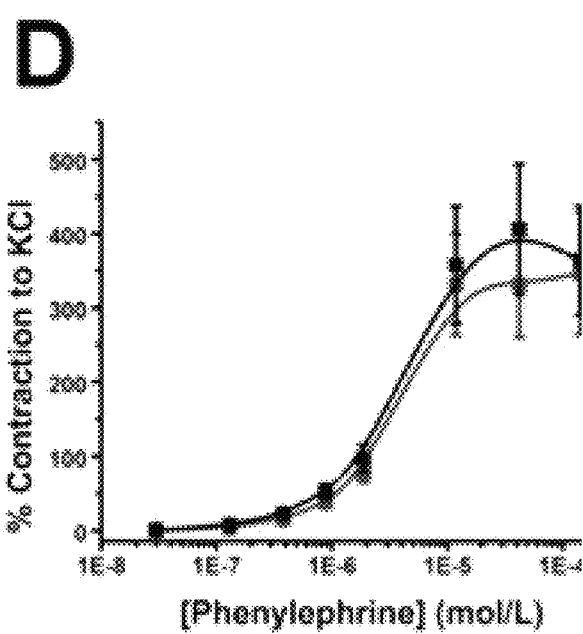
Figure 6E:
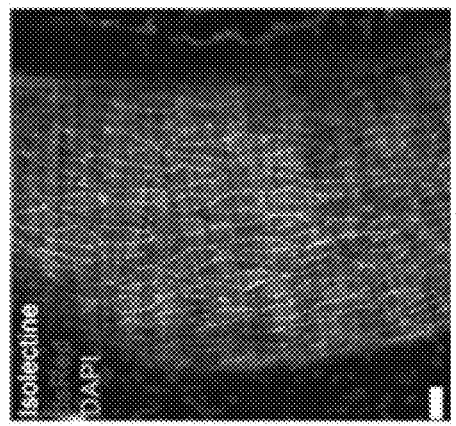
Figure 6E:
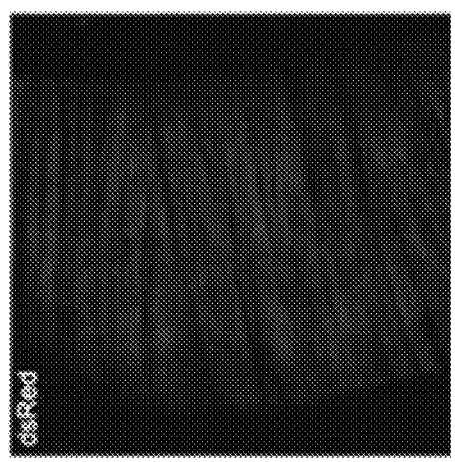
Figure 6E:
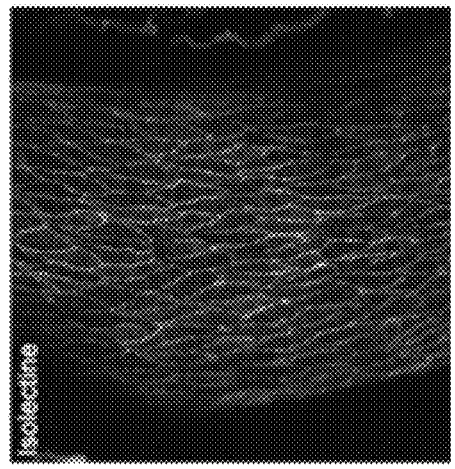

Wild type C57Bl/6 and tdTomato male mice were purchased from Taconic and Jackson respectively, and were used at 8-12 weeks of age. Panx1$^{F1/F1}$ mice were generated as previously described. Briefly, Panx1-targeted embryonic stem cells were obtained from the Knockout Mouse Project (KOMP) Repository and injected into blastocysts of C57BL/6J mice. Smooth muscle myosin heavy chain-Cre modified estrogen receptor binding domain (SMMHC-CreER$^{T2}$) mice were a kind gift from Dr. Offermanns. In these mice, the Cre is only expressed in smooth muscle cells, on the Y chromosome, and is inducible by tamoxifen. This was verified by breeding SMMHC-CreER$^{T2}$ mice with tdTomato mice, which express the tdTomato gene with a loxP-flanked STOP cassette. The expression of tdTomato specifically in the smooth muscle is allowed by injection of tamoxifen, as shown in FIG. 6E. Panx1$^{F1/F1}$ mice were bred with C57Bl/6 to obtain Panx1$^{F1/WT}$ mice, which were further bred together to produce Panx1$^{F1/F1}$ mice (Cre$^-$/Panx1$^{F1}$) and Panx1$^{WT/WT}$ mice (Cre$^-$/Panx1$^{WT}$). Male SMMHC-CreER$^{T2+}$ were bred with female Panx1$^{F1/F1}$ mice, producing SMMHCCreER$^{T2+}$/Panx1$^{F1/WT}$ male and SMMHCCreER$^{T2-}$/Panx1$^{F1/WT}$ females. This progeny was later crossed together and resulted in SMMHCCreER$^{T2+}$/Panx1$^{F1/F1}$ mice (Cre$^+$/Panx1$^{F1}$) and SMMHCCreER$^{T2+}$/Panx1$^{WT/WT}$ mice (Cre$^+$/Panx1$^{WT}$). The four different genotypes (Cre$^-$/Panx1$^{F1}$, Cre$^-$/Panx1$^{WT}$, Cre$^+$/Panx1$^{WT}$, and Cre$^+$/Panx1$^{F1}$) were injected intraperitoneally with 1 mg/kg of tamoxifen per day, for ten days. All mice were housed and used in accordance with University of Virginia Animal Care and Use Committee guidelines.

Chemicals and Reagents

Serotonin (5-HT), bovine serum albumin (BSA), and carbenoxolone (CBX) were purchased from Fisher. ARL 67156 was purchased from Tocris, and $^{10}$Panx1 was produced by Genscript. All other reagents were obtained from Sigma. Probenecid was prepared by dissolving in 1 mol/L NaOH and pH was adjusted to pH 7.4.

Peptides

Amino acid sequences of the four peptides used in the study are indicated in Table 3. We have produced two peptides analog to the mouse Panx1 intracellular loop, designated IL1 and IL2, and one peptide corresponding to the C-tail of Panx1 protein (CT2, FIG. 1A). The IL1, IL2, and CT2 peptides were produced by Anaspec and attached to a TAT sequence (YGRKKQRRR) from the HIV tat transactivation protein. The CT1 peptide has been shown to prevent NMDA-induced Panx1 activation in neurons. All peptides were diluted in water.

Plasmids

The α1DAR plasmid was purchased from Origene (NM_013460), contained a C-terminal Myc-DDK tag (=FLAG), and was expressed in a pCMV6-Entry vector. Mouse Panx1-HA in pEBB was obtained from Dr. Kodi Ravichandran at the University of Virginia. Mutations of Panx1 at the region of amino acids 191-200 (KYPIVEQYLK) were performed using the QuikChangeII Site-directed mutagenesis kit (Stratagene) using the primers identified in Table S3 of Billaud et al. (Sci. Signaling, 2015, February 17, Vol. 8, Issue 364, ra17) All mutations were confirmed by plasmid sequencing.

Cell Culture and Transfection

Human Embryonic Kidney (HEK) 293T cells were cultured as previously described, and were used until passage 20. For ATP measurements, 50,000 cells/well were seeded in 24 well plates pre-coated with 0.01% poly-L-lysine, and transfected using Lipofectamine 2000 (Invitrogen) according to the manufacturer protocol. Briefly, 0.4 μg of α1DAR and 0.4 μg of Panx1$^{WT}$, Panx1$^{KYP>AAA}$, Panx1$^{IVEQ>AAA}$ or Panx1$^{YLK>AAA}$ plasmids were added to each well along with 2 μl of Lipofectamine 2000. For electrophysiology measurements, 4 μg of α1DAR plasmid, 2 μg of Panx1$^{WT}$, Panx1$^{KYP>AAA}$, Panx1$^{IVEQ>AAA}$ or Panx1$^{YLK>AAA}$ plasmids, and 0.5 μg of GFP plasmid were mixed with 10 μl Lipofectamine 2000 and added to a well of 6-well plate seeded with ~70% confluent HEK cells. Cells were split the next morning and plated onto a glass coverslip for recording. ATP measurements and whole-cell recordings were performed 24 hours after transfection.

Pressure Myography

The contractile responses of pressurized thoracodorsal arteries (TDA) were measured as previously described. Briefly, TDA were isolated and placed in cold Krebs-HEPES until cannulation in a pressure arteriograph (Danish Myo-Technology). After a 30 minute equilibration period, cumulative concentrations of contractile agonists were applied to the TDA pressurized at 80 mmHg, and the vessel was visualized with an Olympus IX-71 microscope attached to a Hamamatsu EM-CCD camera coupled to Slidebook imaging software. At the end of the dose response, the viability of the endothelium was verified by applying 1 μmol/L acetylcholine and only TDA exhibiting relaxation reaching 80% of the maximal diameter were analyzed. Lastly, maximal diameter was measured at the end of each experiment in calcium-free Krebs-HEPES supplemented with EGTA (1 mmol/L) and sodium nitroprusside (10 μmol/L). In cases where the vessels were not constricting to the contractile agonist, their viability was assessed by applying 40 mM KCl and only TDA reaching 30% of the maximal diameter were considered for analysis. The contractile responses, as well as the basal tone, are expressed as a percentage of the maximal diameter.

Vessel transfection was performed as previously described by us. Briefly, after isolation, TDA were placed in cold, sterile RPMI supplemented with penicillin (2 mmol/L)/streptomycin (50 U/mL) (Gibco), CaCl$_2$ (2 mmol/L) and 1% BSA. Vessels were transferred to a cuvette containing 100 μL of Nucleofector solution (Lonza) containing 5 μg of plasmid, and subjected to electroporation. Arteries were then placed in supplemented RPMI media in an incubator for 14 to 18 hours until cannulation in the pressure arteriograph as described above.

Wire Myography

Abdominal aorta were isolated from Cre$^+$/Panx1$^{F1}$ injected with peanut oil (vehicle control) or with tamoxifen, cut into 2 mm rings and mounted on a myograph (DMT) as previously described. Each ring was bathed in Krebs solution containing (in mmol/L) 115.2 NaCl, 22.14 NaHCO$_3$, 7.88 D-glucose, 4.7 KCl, 1.18 KH$_2$PO$_4$, 1.16 MgSO$_4$, 1.80 CaCl$_2$, 0.114 ascorbic acid, and 0.027 Na$_2$EDTA and continuously bubbled with 95% O$_2$, 5% CO$_2$. Rings were stretched at 1.2× resting length and allowed to equilibrate for 30 min at 37° C. before application of 154 mm K$^+$. Next, rings were washed in Krebs solution and subjected to cumulative concentrations of phenylephrine. The tension induced by the different doses of phenylephrine was expressed as the percent of the tension induced by 154 mm K$^+$.

Electrophysiology

Whole-cell recordings were obtained at room temperature from transiently transfected HEK293T cells using Axopatch 200B amplifier (Molecular Devices) in a bath solution composed of 140 mmol/L NaCl, 3 mmol/L KCl, 2 mmol/L MgCl$_2$, 2 mmol/L CaCl$_2$, 10 mmol/L HEPES and 10 mmol/L glucose (pH 7.3). Patch pipettes (3-5 MΩ) were filled with a Cs-/TEA-based internal solution, as previously described. Ramp voltage commands with 7-s intervals were applied using pCLAMP software and Digidata1322A digitizer (Molecular Devices). Peak whole-cell currents were determined at +80 mV and normalized to cell capacitance. Current mediated by Panx1 was defined by its sensitivity to carbenoxolone (CBX). In this system, no CBX-sensitive current is observed in HEK293T cells without Panx1. Basal current was recorded for approximately two minutes and PE (20 µmol/L) was applied to the bath solution, which was followed by addition of CBX (50 µmol/L). When indicated, cells were pre-incubated with bath solution containing IL2 peptide or its scrambled version at room temperature for 40-60 minutes prior to the experiment. The effect of PE on Panx1 current was quantified relative to CBX-sensitive basal current, and data was expressed as percent increase in CBX-sensitive current. All experiments were performed on 8 to 22 cells for each conditions tested. Data were analyzed using a Kruskall Wallis test (non-parametric one-way ANOVA) followed by Dunn's post-hoc test.

ATP Assay

Mouse TDAs of equal length were isolated and washed thoroughly to eliminate red blood cells. Vessels were placed in a well of a 96-well plate containing Krebs-HEPES solution supplemented with 1% BSA at 37° C. for 30 minutes to allow for degradation of any ATP released as a result of mechanical stimulation during manipulation of the vessel. For measurements performed on HEK cells: 24 hours after transfection, cells cultured in 24-well plates were cautiously washed twice with warm Krebs-HEPES-BSA and 300 µl of Krebs-HEPES-BSA was added to each well after the last wash as previously described. The plate was then kept in the incubator at 37° C. with 5% CO$_2$ for 30 minutes to allow for degradation of ATP eventually released during the washes.

The ectonucleotidase inhibitor ARL67156 (300 µmol/L) was applied to each well. When indicated, $^{10}$Panx1 (300 µmol/L) or the peptides analog to intracellular regions of Panx1 (3 µmol/L) were added along with the ARL67156. After a 30 minute incubation at 37° C. with the inhibitor(s), phenylephrine (100 µmol/L) or equivalent volume of Krebs-HEPES-BSA was added and the plate was kept at 37° C. After five minutes of phenylephrine stimulation, the media surrounding the TDA or the cells was transferred to an Eppendorf tube and centrifuged for five minutes at 5,000×g to eliminate eventual cell debris. Fifty microliters of the supernatant was transferred to a white-wall 96 well plate and placed in a FluoStar Omega luminometer. The ATP concentration was measured by adding 50 µL of luciferin:luciferase reagent (ATP bioluminescence assay kit HSII; Roche), which was injected into each well and the luminescence was immediately recorded. Data are expressed as a percent increase in ATP concentration compared to unstimulated condition. Each stimulated condition was compared to unstimulated condition performed on the same day, and all experiments were performed on at least 15 wells of HEK cells or three TDAs. Data were analyzed using a Kruskall Wallis test (non-parametric one-way ANOVA) followed by Dunn's post-hoc test.

Total ATP, or ATP content, was measured using the ATP bioluminescence assay kit HSII (Roche) according to the manufacturer's instructions. Briefly, each TDA was homogenized in 500 µl of cell lysis reagent using a douncer on ice. The homogenates were further centrifuged five minutes at 5,000×g and 50 µl of the supernatant was transferred to a white-wall 96 well plate and the ATP concentration was measured as described above.

Immunofluorescence

Experiments on isolated arteries were performed as previously described. Briefly, mice were deeply anesthetized and transcardially perfused with 5 ml of heparinized phosphate-buffered saline (PBS) followed by 5 ml of 4% paraformaldehyde in PBS. TDA were isolated and placed in 4% paraformaldehyde for one hour before paraffin embedding. Cross sections of TDA were subjected to paraffin removal, washed, and blocked for 30 minutes. Next, sections were incubated overnight with primary antibodies directed against Panx1, Panx1, Panx2, and Panx3 described in. All antibodies were produced in rabbit and were detected using an anti-rabbit secondary antibody coupled to AlexaFluor594. Sections were observed using an Olympus Fluoview 1000 as previously described.

To verify the intracellular localization of the different TAT-coupled peptides, TDA were isolated from C57Bl/6 and placed in Krebs-HEPES in presence of the different peptides for 30 minutes. The vessels were next placed in 4% paraformaldehyde for further paraffin embedding. After paraffin removal, cross sections were incubated with a primary antibody directed against the TAT sequence.

Western Blot

Mice TDA were isolated and blood was thoroughly washed to avoid contamination of Panx1 expressed by erythrocytes. Two arteries from one mouse were homogenized on ice using a douncer containing 150 µl of lysis buffer (RIPA buffer supplemented with protease cocktail inhibitor, Sigma). After sonication, protein concentration was measured using a BCA assay (Pierce), samples were mixed with Laemmli buffer and boiled. Protein lysates were subjected to electrophoresis on 4-12% Bis-Tris Gel (Invitrogen), transferred to a nitrocellulose membrane and blocked for 30 minutes using PBS-Tween 0.05% (PBS-T) containing 3% BSA. Membranes were incubated overnight at 4° C. with the primary antibody, and washed twice in PBS-T before adding the corresponding Licor secondary antibody for an hour at room temperature. Membranes were washed, visualized and quantitated using Licor Odissey software as previously described.

Blood Pressure Measurements

Blood pressure was measured using radiotelemetry units (Data Sciences International, DSI) implanted in C57Bl/6, Cre$^-$/Panx1$^{F1}$, Cre$^-$/Panx1$^{WT}$, Cre$^+$/Panx1$^{WT}$, and Cre$^+$/

Panx1$^{F1}$ mice. The catheter of a radiotelemetry unit (TA11PA-C10, DSI) was implanted in the mouse left carotid artery under isoflurane anesthesia, and the catheter was tunneled trough the radiotransmitter placed in a subcutaneous pouch along the right flank of the mouse, as previously described. After implantation, mice were allowed to recover for seven days.

For experiments on the conditional KO mouse model: blood pressure was measured using Dataquest A.R.T. 20 software (DSI) for five days before proceeding to tamoxifen injections at 1 mg/kg for ten days. Blood pressure was recorded for another five days 24 hours after the last tamoxifen injection. The change in mean arterial pressure (ΔMAP) was calculated by subtracting the average MAP measured for five days before tamoxifen injections to the mean arterial pressure measured for five days after the tamoxifen injections. Day mean arterial pressure was measured during inactivity of the mice, i.e. during the light cycle (6 am to 6 pm), while night mean arterial pressure was measured when the mice were most active, during the nocturnal cycle (6 pm to 6 am). Mean arterial pressure before and after tamoxifen injections were compared with a Wilcoxon test (non-parametric paired t test).

For experiments on C57Bl/6: basal blood pressure was measured continuously for 30 minutes before intraperitoneal injection of saline solution or peptide (20 mg/kg in a volume not exceeding 100 µl). Blood pressure was recorded for another 1.5 hours, and the mean arterial pressure data from 1 to 1.5 hours post injection was averaged and compared to the basal blood pressure. The ΔMAP was calculated by subtracting the average mean arterial pressure measured for 30 minutes prior to injection to the mean arterial pressure measured for 30 minutes one hour post injection. Mean arterial pressure before and after peptide or saline injections were compared with a Wilcoxon test (non-parametric paired t test).

Data Analysis

All data were analyzed using GraphPad Prism and Origin software and are presented as mean±sem. All vasoreactivity experiments were analyzed using a two-way ANOVA.

Results

Figure 1B:
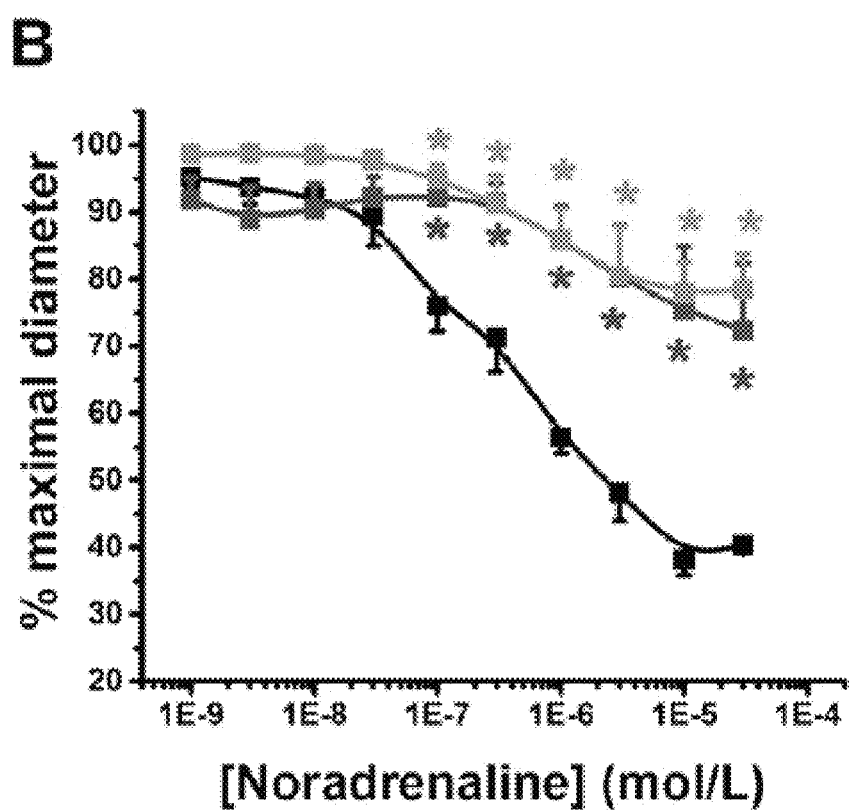
Figure 1C:
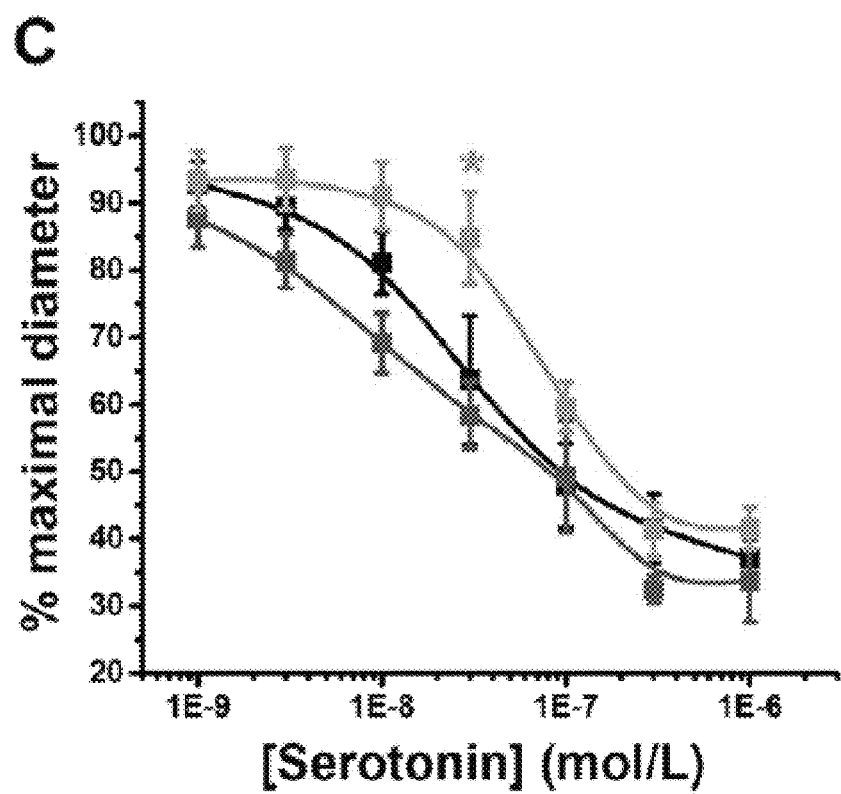
Figure 1D:
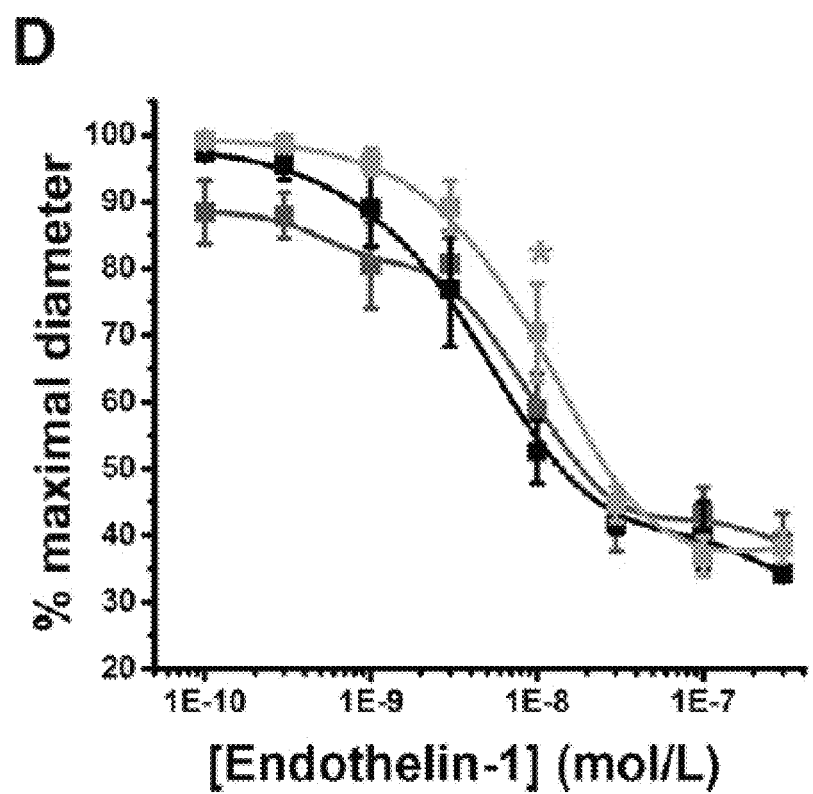

Pharmacological or Molecular Inhibition of Panx1 Reduces α1AR-Dependent Responses in Isolated Arteries Using pressure arteriography on TDA dissected from C57Bl/6 mice (as described; and aortic ring contraction, as described), we measured the effect of pannexin inhibitors, probenecid and 10Panx1, on the contractile response upon stimulation with different vasoconstrictors: phenylephrine (FIG. 1A), noradrenaline (also called norepinephrine) (FIG. 1B), serotonin (also known as 5-HT) (FIG. 1C) and endothelin-1 (FIG. 1D). Both pannexin inhibitors significantly inhibited phenylephrine- and noradrenaline-mediated contraction of TDA (FIGS. 1A-B), that was associated with a decrease in the maximum effect of both agonists ($E_{MAX}$), without affecting the $EC_{50}$ values (Table 1). In contrast, $^{10}$Panx1 and probenecid had no effect on contraction of TDA measured in response to cumulative concentrations of serotonin or endothelin-1 (FIGS. 1C-D; Table 1).

Figure 1E:
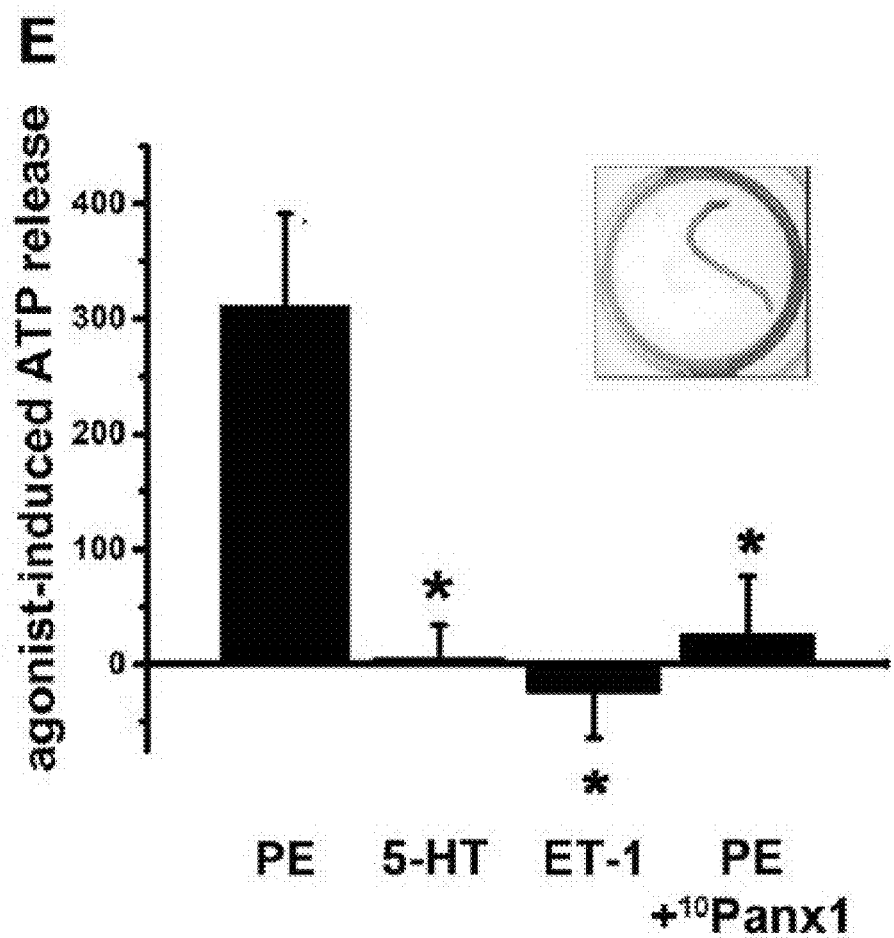

To determine if the TDA response involved release of ATP, we dissected TDAs from C57Bl/6 mice and measured the accumulation of extracellular ATP in response to various agonists in the medium (FIG. 1E, inset). The TDAs were placed in a well of a 96 well plate in Krebs-HEPES solution and treated with the ectonucleotidase inhibitor ARL67156 for 30 minutes. Next, arteries were treated with a contractile agonist for five minutes and the amount of ATP in the media surrounding the vessel was determined using the ATP bioluminescence assay kit HSII (Roche). Phenylephrine stimulated ATP release from TDAs and this effect was significantly reduced when Panx1 channels were blocked with $^{10}$Panx1 prior to stimulation (FIG. 1E). In contrast to phenylephrine, neither serotonin nor endothelin-1 promoted ATP release from intact TDAs (FIG. 1E). Taken together, these pharmacological studies suggested a link between α1AR stimulation and Panx1 activation, which indicated the involvement of a purinergic component through the release of cellular ATP in adrenergic-stimulated vasoconstriction.

To further test the role for Panx1 in α1AR-mediated vasoconstriction, we generated an inducible, SMC-specific Panx1-knockout mouse model The Panx1$^{F1/F1}$ mice were generated using Panx1-targeted embryonic stem cells obtained from the Knockout Mouse Project (KOMP) Repository and injected into blastocysts of C57BL/6J mice. Panx1$^{F1/F1}$ mice were bred with smooth muscle myosin heavy chain-Cre modified estrogen receptor binding domain (SMMHC-CreER$^{T2+}$) mice to produce Cre$^-$/Panx1$^{F1}$, Cre$^-$/Panx1$^{WT}$, Cre$^+$/Panx1$^{F1}$, and Cre$^+$/Panx1$^{WT}$ mice. Panx1 deletion was induced by intraperitoneal injection of 1 mg/kg of tamoxifen per day, for ten days. Wild type C57Bl/6 male mice were purchased from Taconic. All mice were used at 8-12 weeks of age, and were housed and used in accordance with University of Virginia Animal Care and Use Committee guidelines.

Figure 2A:
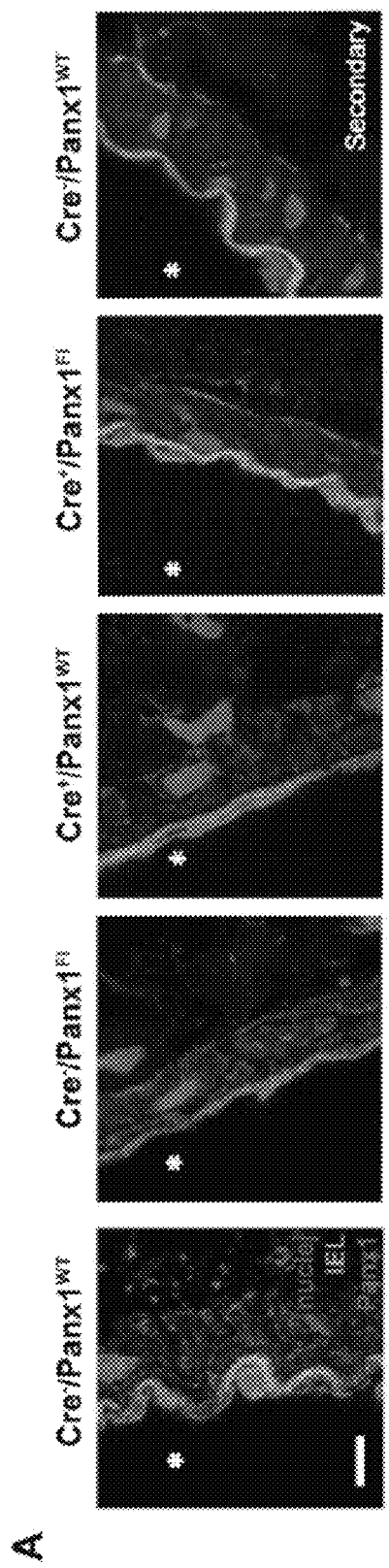
FIGS. 2 (A-G): Inducible SMC deletion of Panx1 selectively inhibits vasoconstriction and ATP release upon α1AR stimulation. (2A) Representative immunofluorescence micrographs showing Panx1 labeling (red) on cross sections of TDAs isolated from mice of the indicated genotypes. All mice had been injected with tamoxifen for ten days. The far right panel shows a negative control (secondary antibody only) on a cross section of a TDA isolated from Cre$^-$/Panx1$^{WT}$ mice. The autofluorescence of the internal elastic lamina (IEL) appears in green, and the nuclei were labelled with DAPI (blue). * indicates the lumen. Scale bar=10 μm. (2B) Basal tone exhibited by TDA from each genotype. (2C-F) Contraction of pressurized TDA isolated from Cre$^-$/Panx1$^{WT}$ mice (black curves), Cre$^-$/Panx1$^{F1}$ mice (dark grey curves), Cre$^+$/Panx1$^{WT}$ mice (light grey curves), and Cre$^+$/Panx1$^{F1}$ (green curves) all injected with tamoxifen for ten days and stimulated with cumulative concentrations of phenylephrine (n=6-16), noradrenaline (n=4-8), serotonin (n=5-10), or endothelin-1 (n=4-8). * indicates p<0.05 compared to Cre$^-$/Panx1$^{WT}$ using a 2-way ANOVA. (2G) Histogram showing the phenylephrine (PE)-induced ATP release from intact TDA isolated from mice of the indicated genotypes, all injected with tamoxifen for ten days. Data are presented as a percent increase in ATP concentration from unstimulated conditions. * indicates p<0.05 compared to Cre$^-$/Panx1$^{WT}$ using a Kruskal Wallis test, n=4-8.

We confirmed cell type-specific deletion of Panx1 by immunofluorescence analysis of TDA cross sections. Whereas we detected Panx1 in both endothelial cells and SMCs of arteries from Cre$^-$/Panx1$^{WT}$ mice, Cre$^-$/Panx1$^{F1}$ mice, and Cre$^+$/Panx1$^{WT}$ mice (littermate controls; all injected with tamoxifen); Panx1 immunoreactivity was absent in the SMCs of Cre$^+$/Panx1$^{F1}$ mice injected with tamoxifen (FIG. 2A and FIG. 6A). Western blotting of TDA lysates showed reduced amounts of Panx1 and we assume that the residual Panx1 was from endothelial cells (FIG. 6B). Although knockdown of a pannexin isoform may result in compensation by other pannexin isoforms; we did not detect an increase in the abundance of Panx2 and Panx3 in the tamoxifen-treated Cre$^+$/Panx1$^{F1}$ mouse TDAs (FIG. 6A). We also confirmed that the knockdown of Panx1 in SMC did not alter total intracellular ATP content (FIG. 6C) or α1DAR abundance (FIG. 6B) in intact arteries.

Figure 2B:
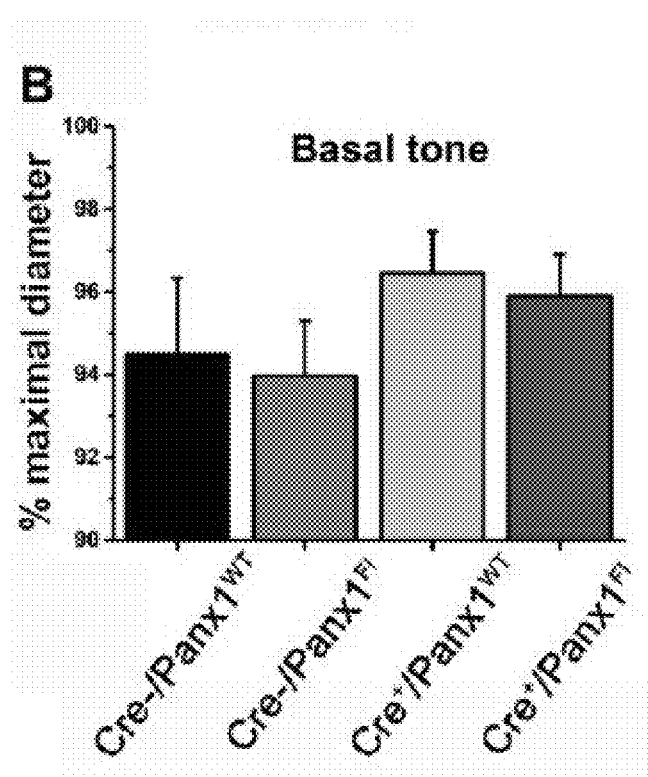
Figure 2C:
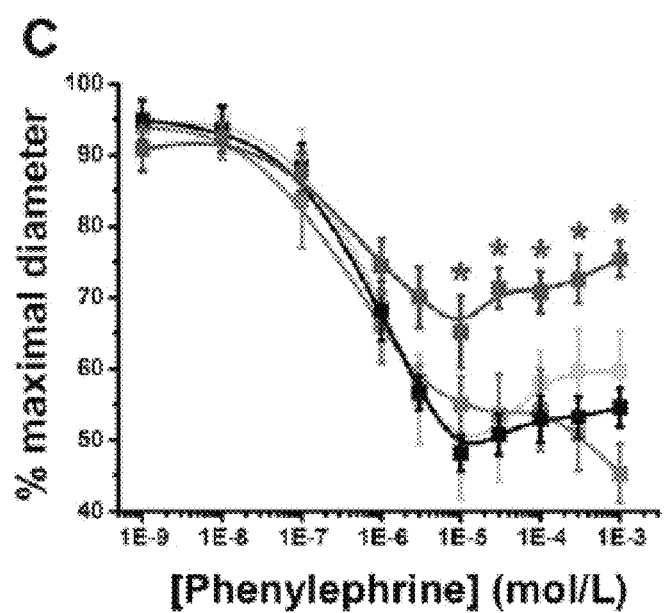
Figure 2D:
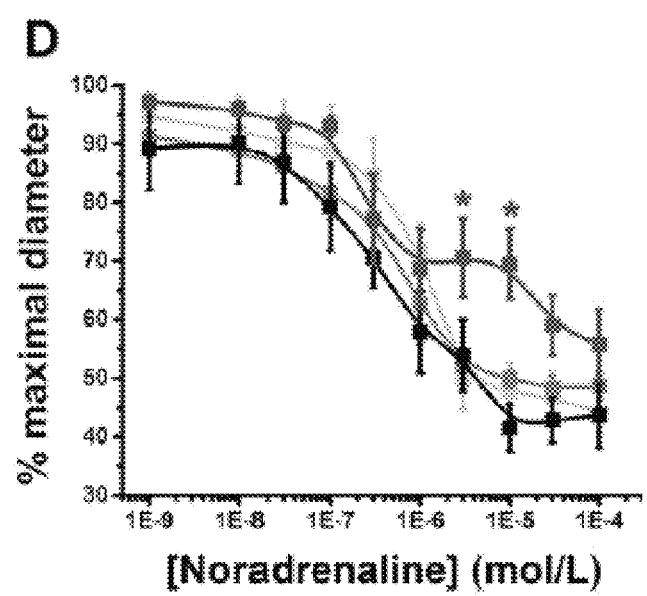
Figure 2E:
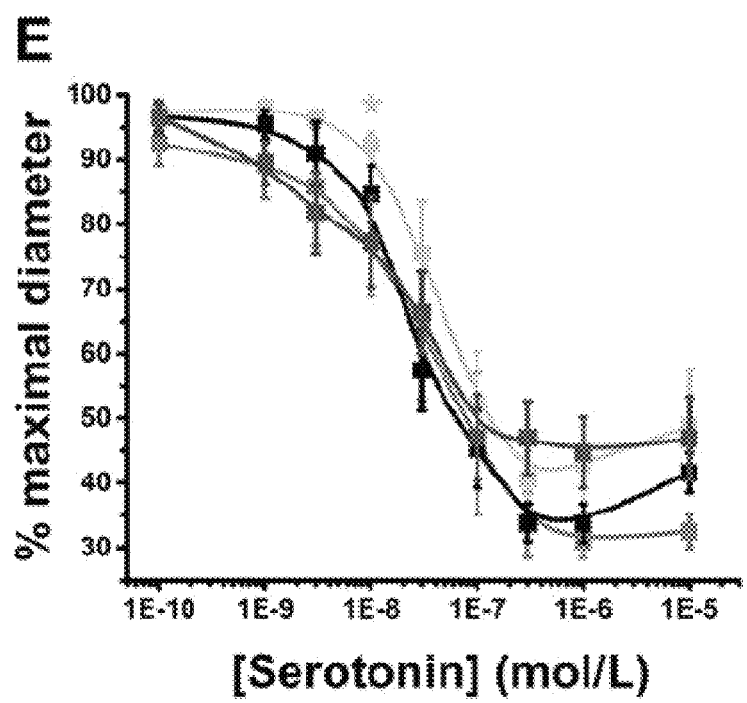
Figure 2F:
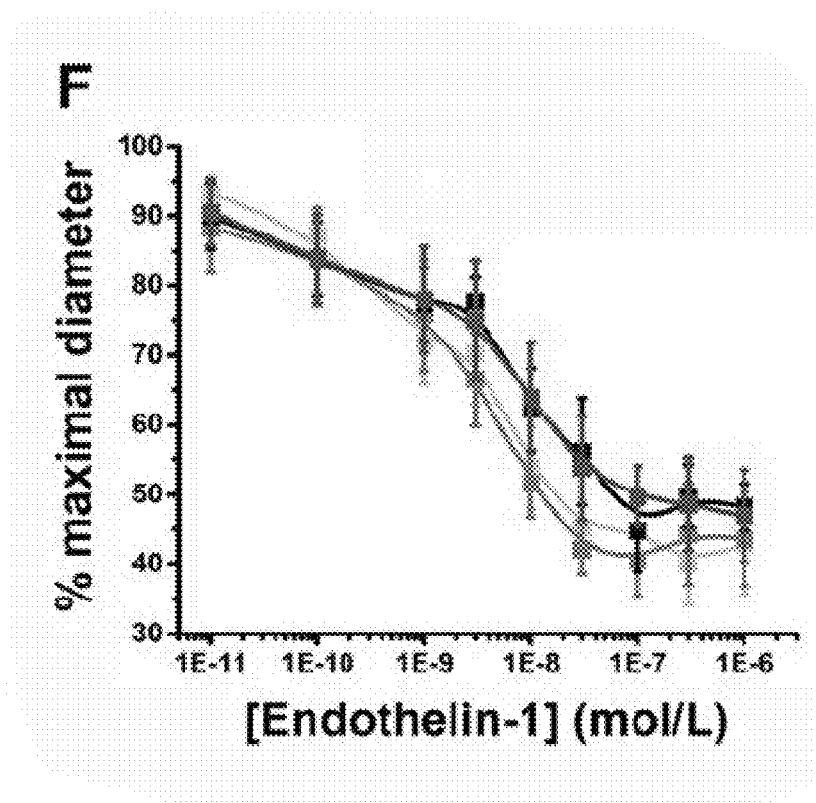
Figure 2G:
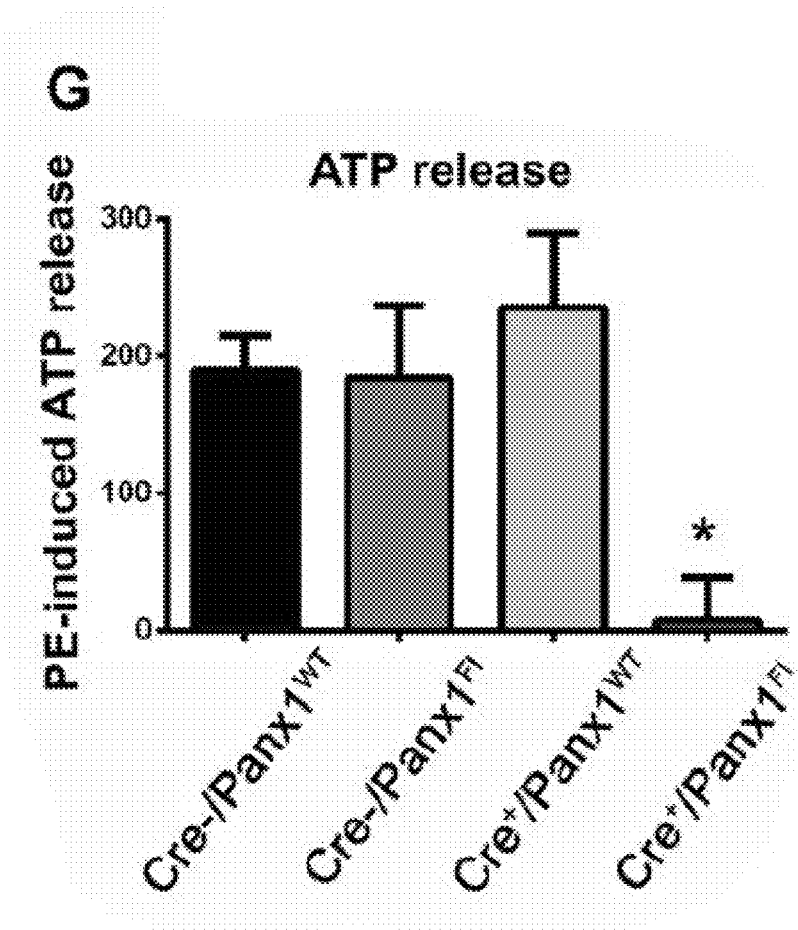

Initial functional tests performed on TDAs from the SMC-specific Panx1-knockout mice and littermate controls revealed no difference in basal vascular tone (FIG. 2B). However, in TDAs from the SMC-specific Panx1-knockout mice, the contractile responses to phenylephrine or noradrenaline were significantly reduced (FIG. 2C-D). The $E_{MAX}$ for phenylephrine was reduced to 69.1±3.06% of maximal diameter compared to an $E_{MAX}$ of approximately 50% of maximal diameter for TDAs isolated from the three control genotypes; the $EC_{50}$ values were not different among the different genotypes (Table 2). To confirm that this effect was specific to Panx1 deletion and not to a deficient α1AR response in these mice, we measured phenylephrine-induced vasoconstriction in abdominal aortic rings, which are devoid of Panx1 in the SMC layer, isolated from tamoxifen-treated or control Cre$^+$/Panx1$^{F1}$ mice. Abdominal aortic rings from tamoxifen-treated and control mice showed the same $E_{MAX}$ and $EC_{50}$ for phenylephrine-induced vasoconstriction (FIG. 6D and Table 6). The contractile responses of TDAs isolated from the SMC-specific Panx1-knockout mice to serotonin or endothelin-1 were not significantly different from TDAs isolated from Cre$^-$/Panx1$^{WT}$ mice, Cre$^-$/Panx1$^{F1}$ mice, or the Cre$^+$/Panx1$^{WT}$ mice (FIG. 2E-F, Table 2). Consistent with α1AR activating Panx1 to promote ATP release, SMC-specific Panx1 knockout attenuated phenylephrine-induced ATP release from TDAs (FIG. 2G). Immunohistochemistry demonstrated specificity of Cre to SMC. (FIG. 6E).

SMC-Specific Panx1-Knockout Impairs Circadian Regulation of Blood Pressure

Based on the central role of α1AR signaling in blood pressure homeostasis, we evaluated the effect of Panx1 deletion on systemic blood pressure. Blood pressure was measured using radiotelemetry units as previously described by us. Blood pressure was measured on the conditional KO mouse model for five days before proceeding to tamoxifen injections, and for another five days 24 hours after the last tamoxifen injection. The change in mean arterial pressure (ΔMAP) was calculated by subtracting the average MAP measured for five days before tamoxifen injections to the MAP measured for five days after the tamoxifen injections. Day MAP was measured during the light cycle (06:00-18:00), while night MAP was measured during the nocturnal cycle (18:00 to 06:00). For experiments on C57Bl/6, basal blood pressure was measured continuously for 30 minutes before intraperitoneal injection of saline solution or peptide, and for 1.5 hours after the injection. The MAP data from 1 to 1.5 hours post injection was averaged and compared to the basal blood pressure. The change in ΔMAP was obtained by subtracting the average MAP measured for 30 minutes prior to injection to the MAP measured for 30 minutes one hour post injection.

Figure 3A:
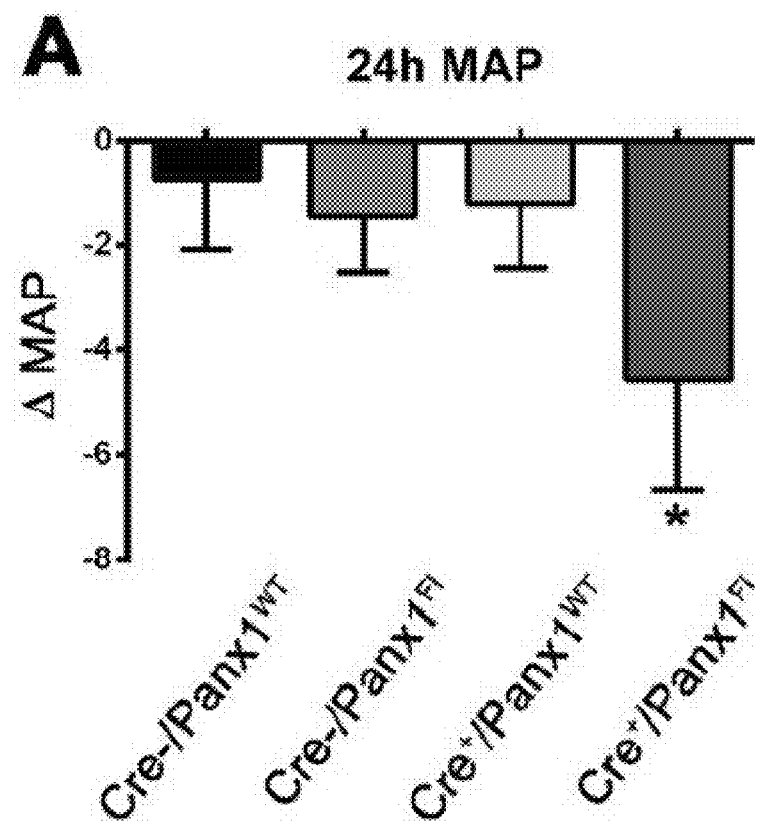
FIGS. 3 (A-C): Inducible SMC deletion of Panx1 reduces blood pressure in freely moving mice. (3A) Difference in the 24-hour mean arterial pressure (MAP) of mice of the indicated genotypes before and after tamoxifen injections. (3B) Difference in the mean arterial pressure (MAP) during the day cycle (12 hour light: 06:00-18:00) of mice of the indicated genotypes before and after tamoxifen injections. (3C) Difference in the mean arterial pressure (MAP) during the night cycle (12 hour no light: 18:00-06:00) of mice of the indicated genotypes before and after tamoxifen injections. * indicates p<0.05 comparing the MAP before and after tamoxifen injection using a non-parametric paired t-test (Wilcoxon), n=4-7.
Figure 3B:
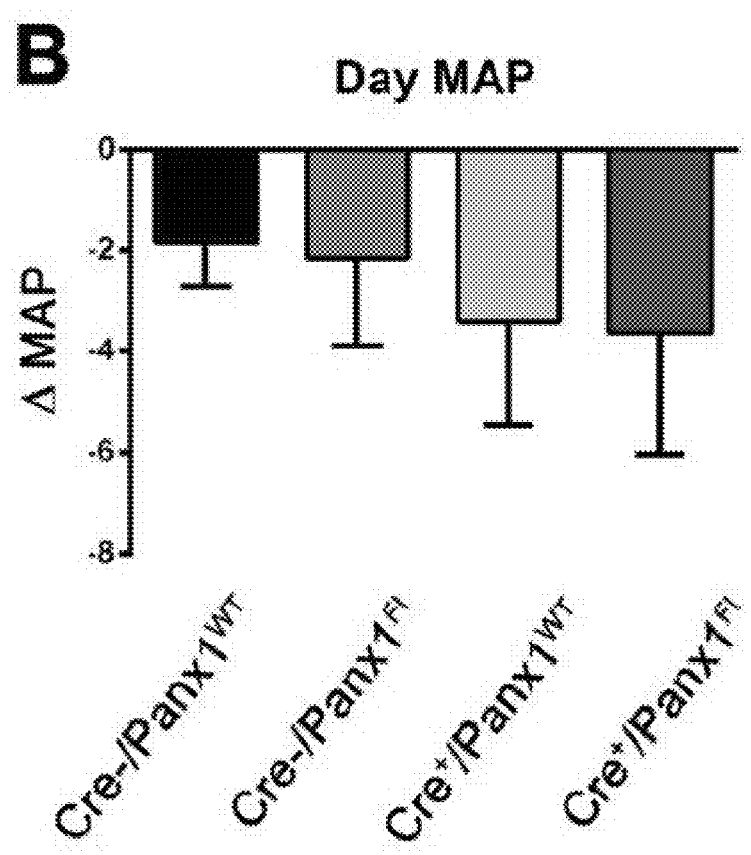
Figure 3C:
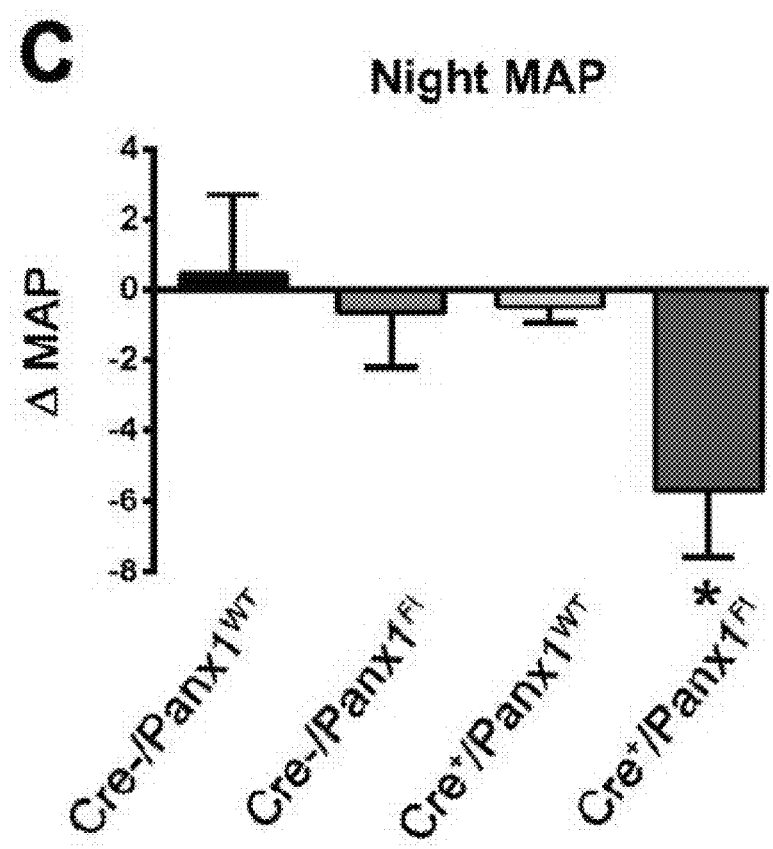

Administration of tamoxifen significantly decreased the mean arterial blood pressure in Cre$^+$/Panx1$^{F1}$ mice by 4.6±2.1 mmHg, with no evident changes observed in the mice that retained endogenous amount of Panx1 (Cre$^-$/Panx1$^{WT}$, Cre$^-$/Panx1$^{F1}$, Cre$^+$/Panx1$^{WT}$) (FIG. 3A). This effect appeared independent of heart rate, which was unchanged following tamoxifen injection in Cre$^+$/Panx1$^{F1}$ mice (569±4 beats per min before tamoxifen vs 549±7 after tamoxifen). Interestingly, the mean arterial blood pressure measured during the day was unchanged (FIG. 3B), whereas during the night cycle (the active period for rodents during which sympathetic nerve activity is greatest) the blood pressure was significantly decreased in the SMC-specific Panx1-knockout mice (FIG. 3C). Thus, both pharmacological and molecular evidence from intact arteries and live animals suggested a functional link in SMCs between the sympathetic signaling through α1AR and Panx1-mediated ATP release in controlling vascular tone and systemic blood pressure.

α1AR-Stimulated Vasoconstriction Involves the Intracellular Loop of Panx1

Figure 4A:
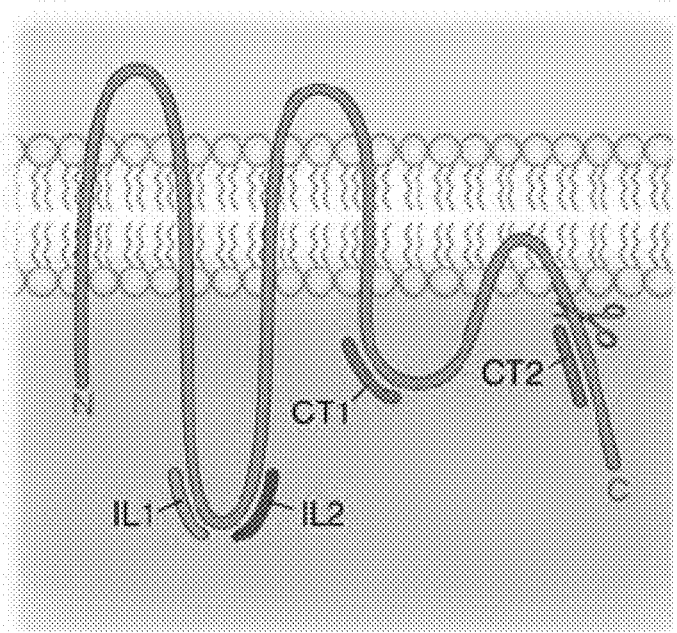
FIGS. 4 (A-J): A peptide analog to a Panx1 intracellular loop sequence inhibits vasoconstriction and ATP release upon α1AR stimulation and reduces blood pressure. (4A) A diagram showing the position of each of the four peptides on mouse Panx1. (4B-E) The effects of the indicated peptide inhibitor on phenylephrine-induced constriction of pressurized TDAs. (4E-H) The effect of IL2 peptide on constriction of pressurized TDAs induced by the indicated concentrations of agonists. In 4B through 4H, the black curves represent constriction in absence of peptide, n=4-7, * indicates p<0.05 compared to constriction in absence of peptide using a 2-way ANOVA. (4I) The effect of the indicated peptide on phenylephrine (PE)-induced ATP release. Data are presented as a percent increase in ATP concentration from unstimulated conditions. n=3-8, * indicates p<0.05 compared to no peptide using a Kruskal-Wallis test. (4J) The difference between the mean arterial pressures (ΔMAP) measured before and after injection of saline, IL2 peptide, or its scrambled IL2 peptide in C57Bl/6 mice. * indicates p<0.05 comparing before and after vehicle and peptide injections using a nonparametric paired t-test (Wilcoxon), n=7-9. Animals were injected with 5 mg/kg of peptide.
Figure 4B:
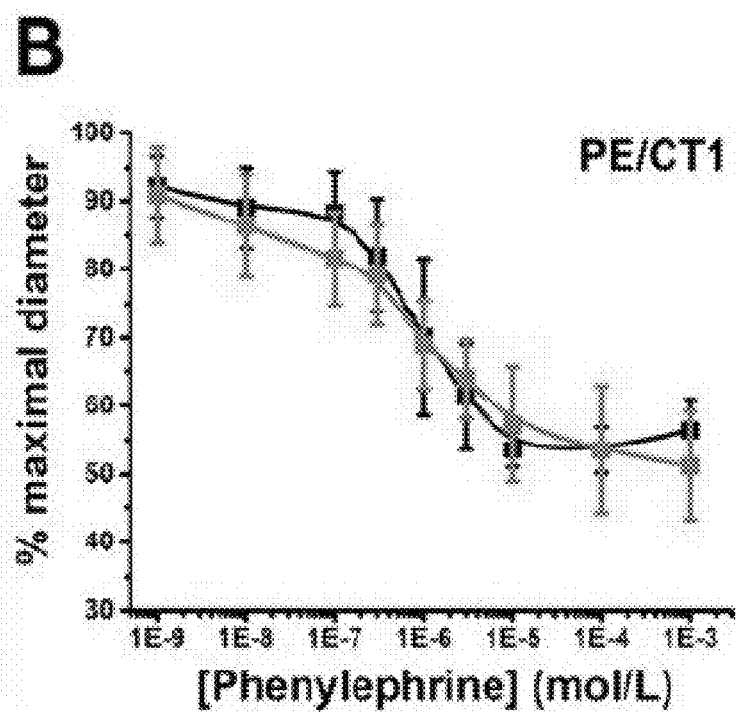
Figure 4C:
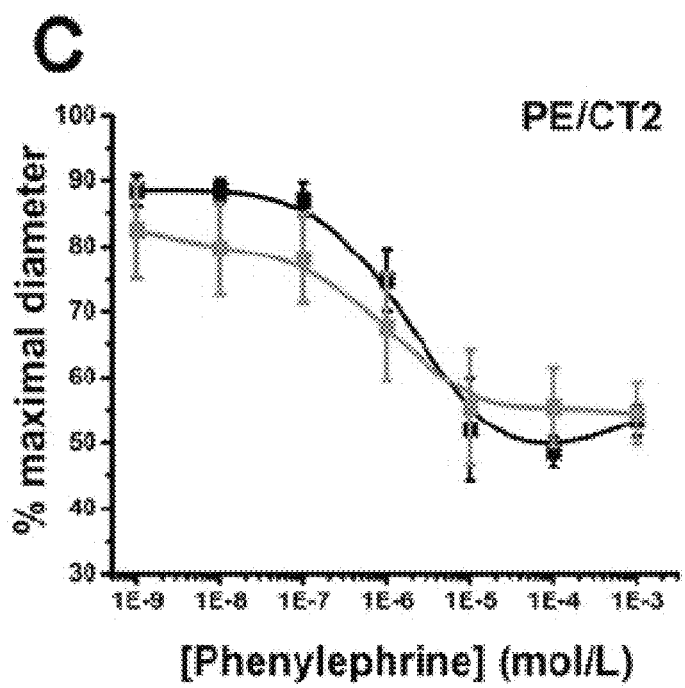
Figure 4D:
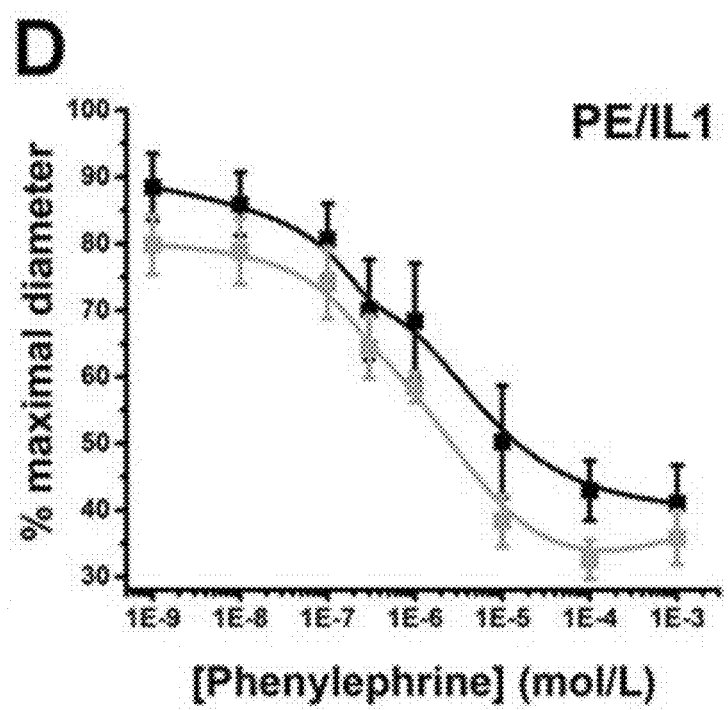
Figure 4E:
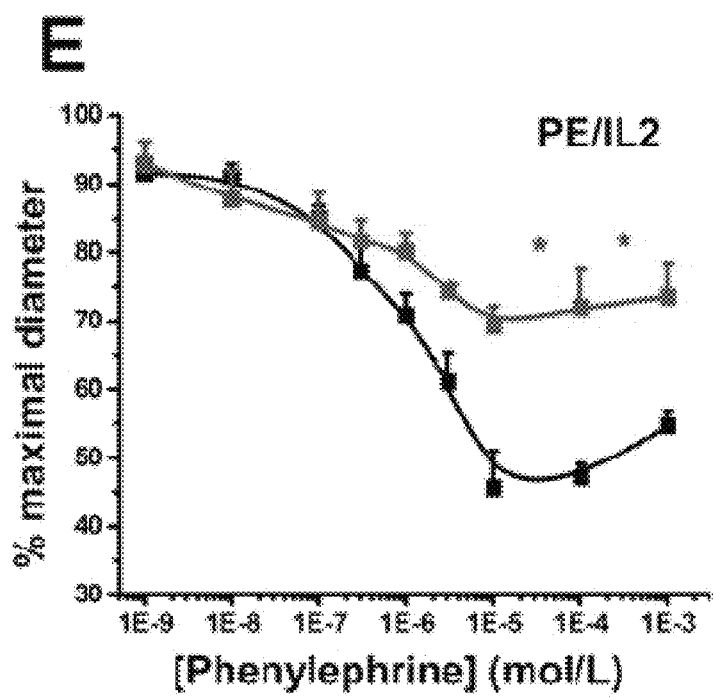
Figure 7A:
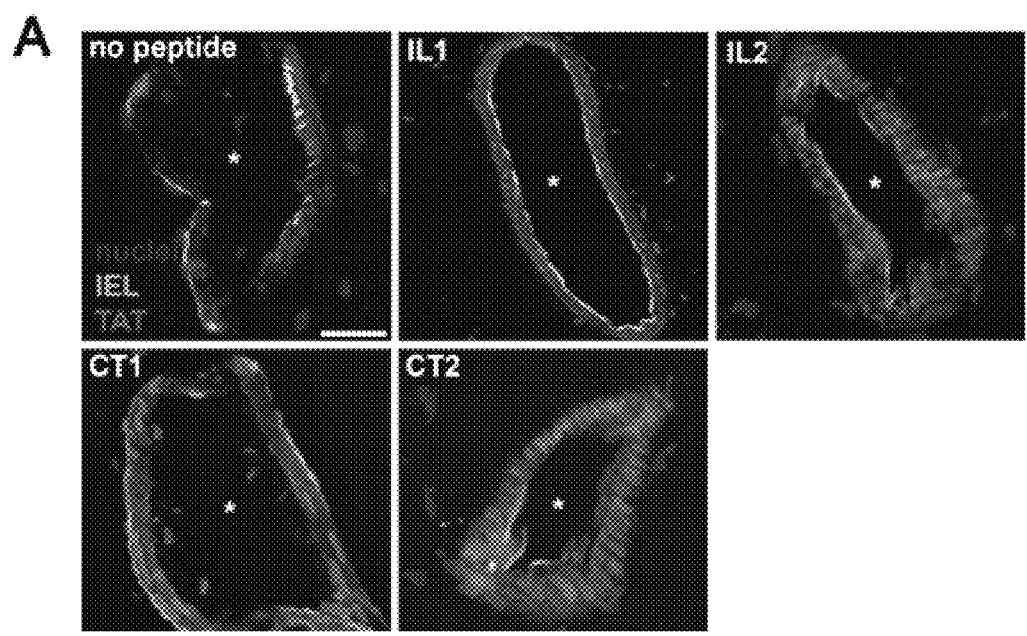
FIGS. 7A-C: Effect of IL2 scrambled peptide and TAT peptide on phenylephrine-mediated constriction and ATP release. (7A-five images) Representative immunofluorescent labeling using an antibody directed against the TAT sequence (red) on cross sections of TDAs incubated with the IL1, IL2, CT1, or CT2 peptides. * indicates the lumen, green is the autofluorescence of the internal elastic lamina, and blue indicates the nuclei labeled with DAPI. Scale bar is 50 μm. (7B) Effect of scrambled IL2 peptide (grey curve) and TAT peptide (black curve with open boxes) on contraction of pressurized TDAs in response to cumulative concentrations of phenylephrine. n=5 for each condition. (7C) The effect of no peptide (black) scrambled IL2 peptide (white) and TAT peptide (grey) was tested on phenylephrine-induced ATP release. Data are expressed as a percent increase in ATP concentration from unstimulated conditions. n=3-4.

To determine the region of Panx1 necessary for channel activation in response to α1AR stimulation, we produced short peptides derived from the intracellular regions of the Panx1 channel. We generated two peptides mimicking unique mouse Panx1 (mPanx1) sequences in the first intracellular loop (IL1 and IL2) and two peptides mimicking unique mPanx1 sequences in the C-terminal region, one in second intracellular loop (CT1) and one in the C-terminal tail (CT2) (FIG. 4A scissors indicate caspase 3 cleavage site; Table 3). All peptides also contained a TAT sequence to facilitate entry into cells and we verified the intracellular localization of each peptide by immunofluorescence detection of the TAT sequence in TDAs pre-incubated with each peptide (FIG. 7A). We tested the effect of each peptide on phenylephrine-induced contractile responses in pressurized TDAs from C57Bl/6 mice (FIGS. 4B-E). The CT1, CT2, and IL1 peptides did not affect phenylephrine-induced constriction (FIG. 4B, C, D; Table 4). In contrast, the IL2 peptide significantly decreased phenylephrine-induced constriction (FIG. 4E, Table 4). Note that these differences in effects of phenylephrine were similar in magnitude to those observed in arteries from SMC-specific Panx1-knockout mice and littermate controls (FIG. 2C, Table 2). A scrambled version of the IL2 peptide, as well as the TAT sequence alone, had no significant effect on the phenylephrine response (FIG. 7B; Table 7).

Figure 4F:
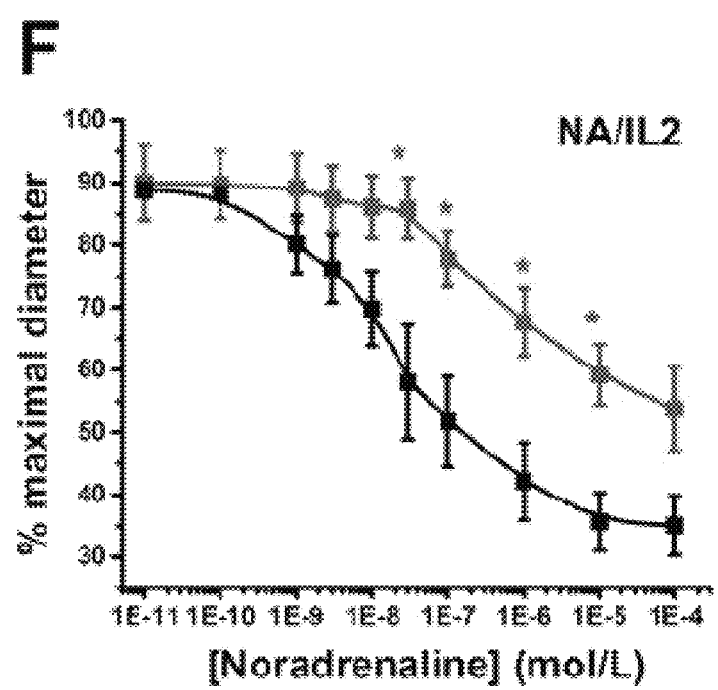
Figure 4G:
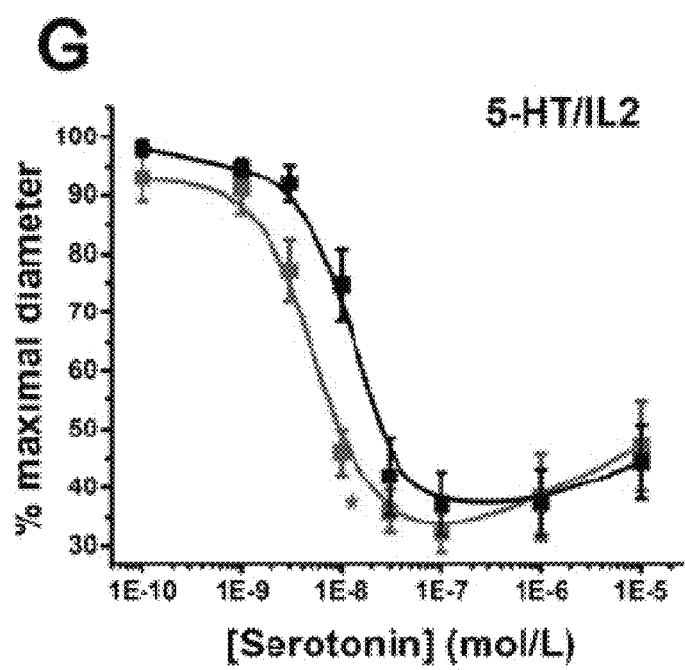
Figure 4H:
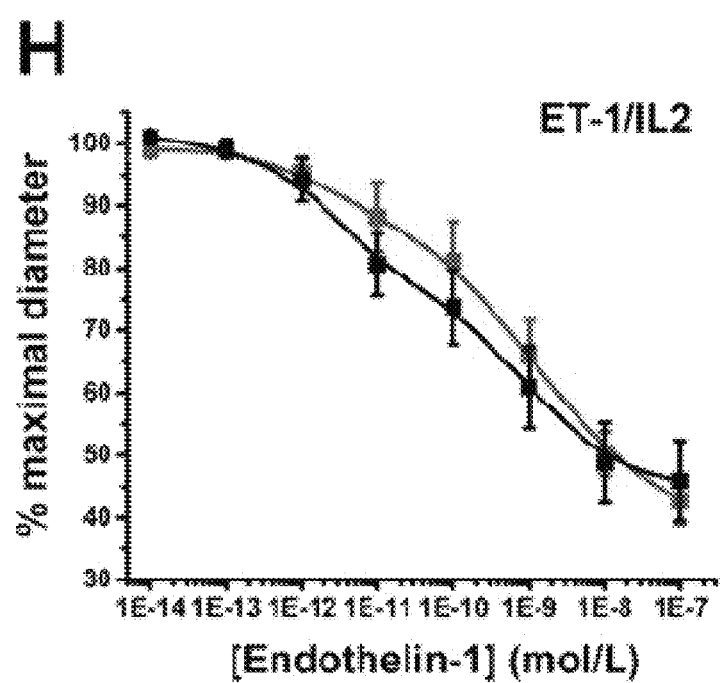

Because Panx1 activity appeared selectively involved in α1AR-mediated responses, we tested the effect of the IL2 peptide on the response to noradrenaline (FIG. 4F), serotonin (FIG. 4G), and endothelin-1 (FIG. 4H). As expected, whereas the IL2 peptide inhibited noradrenaline-induced constriction, vasoconstriction mediated by serotonin or endothelin-1 was similar in the presence or absence of the IL2 peptide (Table 4).

Figure 4I:
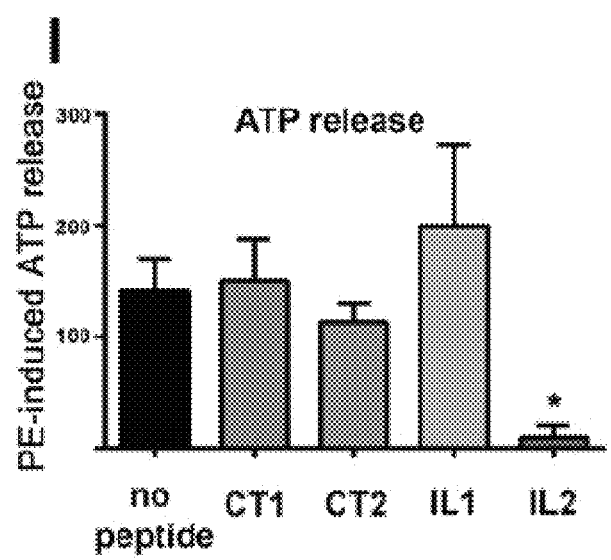
Figure 4J:
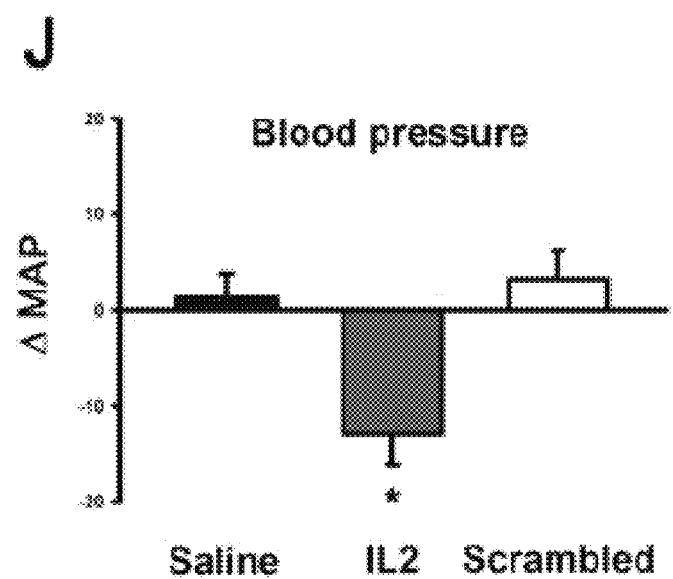
Figure 7B:
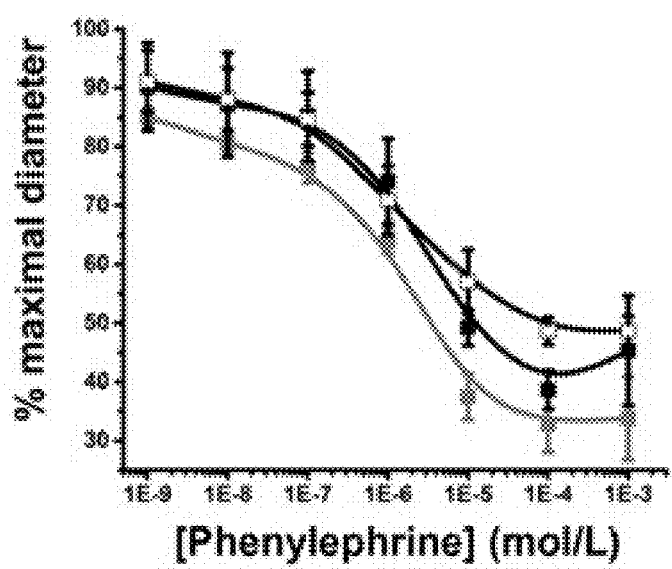
Figure 7C:
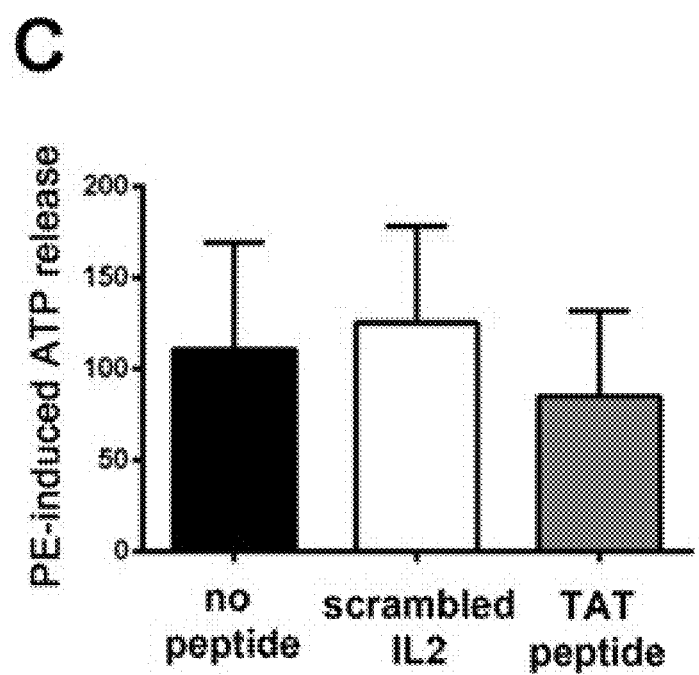

Additionally, phenylephrine-induced ATP release was significantly decreased only by the IL2 peptide (FIG. 4I) with the scrambled version of IL2 and the TAT sequence alone having no effect (FIG. 7C). Continuous recording of blood pressure in conscious C57Bl/6 mice revealed that acute injection of the IL2 peptide significantly reduced the mean arterial blood pressure by 13.0±3.3 mmHg within 1.5 hours, while its scrambled version had no significant effect (FIG. 4J).

α1AR-Stimulated Activation of the Panx1 Channel Involves the Intracellular Loop of Panx1

Figure 5A:
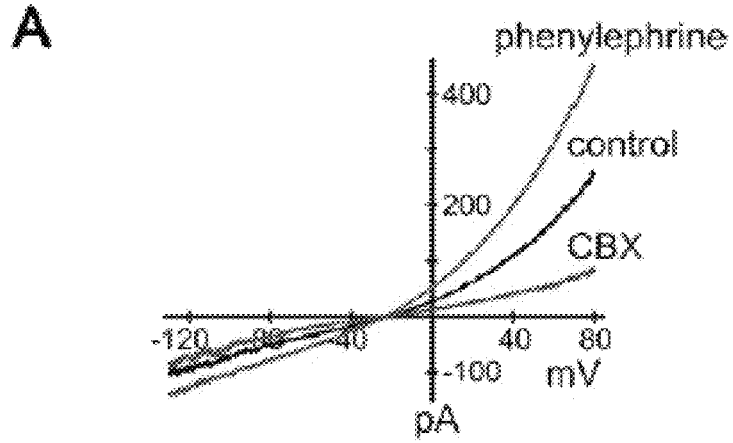
FIGS. 5 (A-F): Characterization of α1DAR-mediated ATP release by Panx1 using a heterologous system. (5A) Left panel: Representative current-voltage (I-V) curve obtained from whole-cell patch clamp recording of HEK293 cells cotransfected with Panx1 and α1DAR before (control, black curve) and after stimulation with phenylephrine (green curve), and upon application of carbenoxolone (CBX, red curve). Right panel: Representative time course of whole-cell current recorded from cotransfected HEK293 cell showing the effect of phenylephrine and CBX. (5B) Phenylephrine-induced Panx1 current (top panel) and Phenylephrine-induced ATP release (bottom panel) in untransfected HEK293 cells or HEK293 cells transfected with the indicated constructs. (5C) The effect of the IL2 peptide and scrambled IL2 peptide on Phenylephrine-induced Panx1 current (top panel) and phenylephrine-induced ATP release (bottom panel). (5D) Phenylephrine-induced Panx1 current (top panel) and phenylephrine-induced ATP release (bottom panel) in HEK293 cells cotransfected with α1DAR and the indicated Panx1 construct. Panx1 current data (5B through D top panels) are presented as a percent increase of CBX-sensitive current at +80 mV, or as a percent increase of ATP concentration from unstimulated conditions (5B through D bottom panels). 5B through D, * indicates p<0.05 compared to co-transfected conditions (5B), no peptide (5C) or Panx1$^{WT}$ (5D) using a Kruskal-Wallis test. (5E) Phenylephrine-induced contraction of pressurized TDAs isolated from Cre$^+$/Panx1$^{F1}$ mice not injected with tamoxifen and electroporated without plasmid (black curve), Cre$^+$/Panx1$^{F1}$ mice after injection with tamoxifen for 10 days and then electroporated without plasmid (grey curve), or Cre$^+$/Panx1$^{F1}$ mice after injection with tamoxifen for 10 days and then electroporated with wild-type Panx1 (Panx1$^{WT}$) (pink curve). (5F) Phenylephrine-induced contraction of pressurized TDAs from control mice as indicated in E (black and gray curves) and Cre$^+$/Panx1$^{F1}$ mice after injection with tamoxifen for 10 days and then electroporated with Panx1$^{YLK>AAA}$ (blue curve). In 5E and 5F, * indicates p<0.05 compared to control Cre$^+$/Panx1$^{F1}$ (black curve) using a 2-way ANOVA, n=6 mice.
Figure 5A:
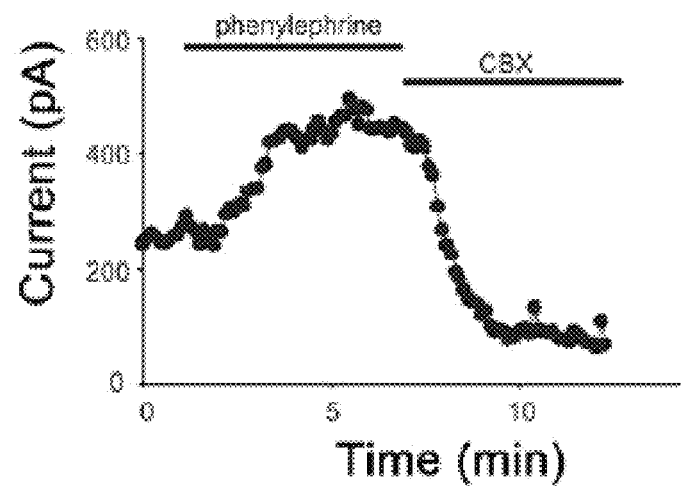
Figure 5B:
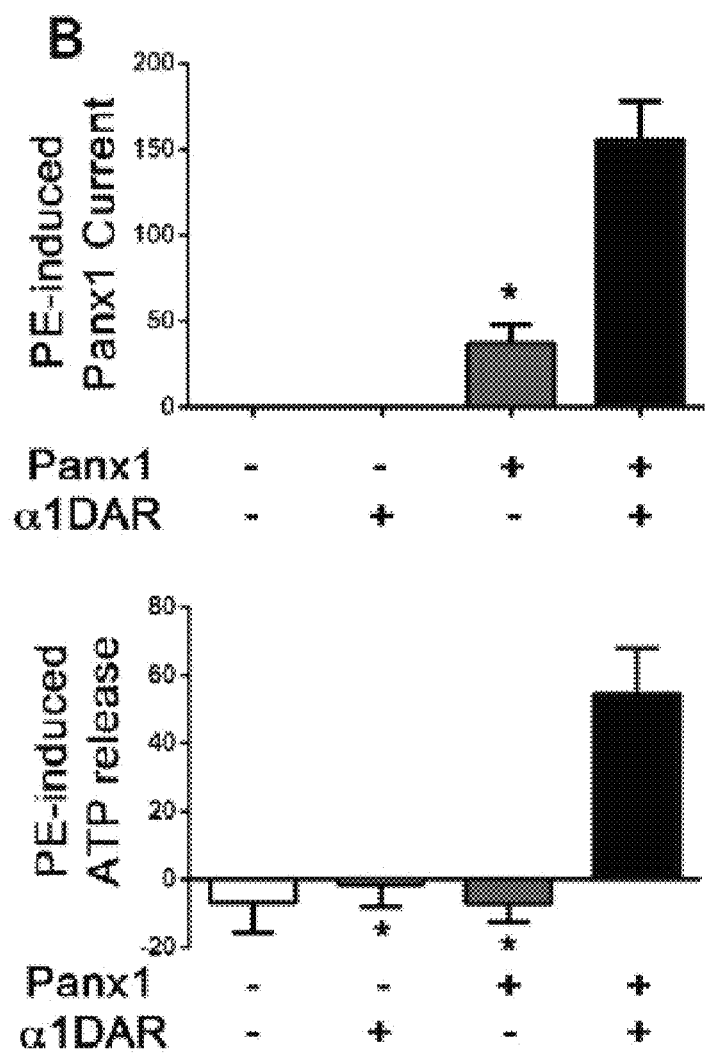

To test if α1AR stimulation triggered opening of the Panx1 channel and the importance of the region represented by the IL2 peptide, we cotransfected mPanx1 and α1DAR into HEK293 cells and monitored whole-cell currents by patch clamp electrophysiology. Whole-cell currents recorded from c-transfected HEK293 cells displayed characteristics typical of Panx1 currents: The cells showed an outwardly rectifying current-voltage relationship and inhibition of this current by carbenoxolone (CBX) (FIG. 5A). In cells expressing both mPanx1 and α1DAR, phenylephrine increased this current and CBX abolished the current (FIG. 5A, right). This phenylephrine-induced current activation required cotransfection of Panx1 and was significantly smaller without cotransfection of α1DAR (FIG. 5B, top). Similarly, only observed in only cells cotransfected with Panx1 and α1DAR exhibited phenylephrine-induced ATP release (FIG. 5B, bottom; ATP release measured as described).

Figure 5C:
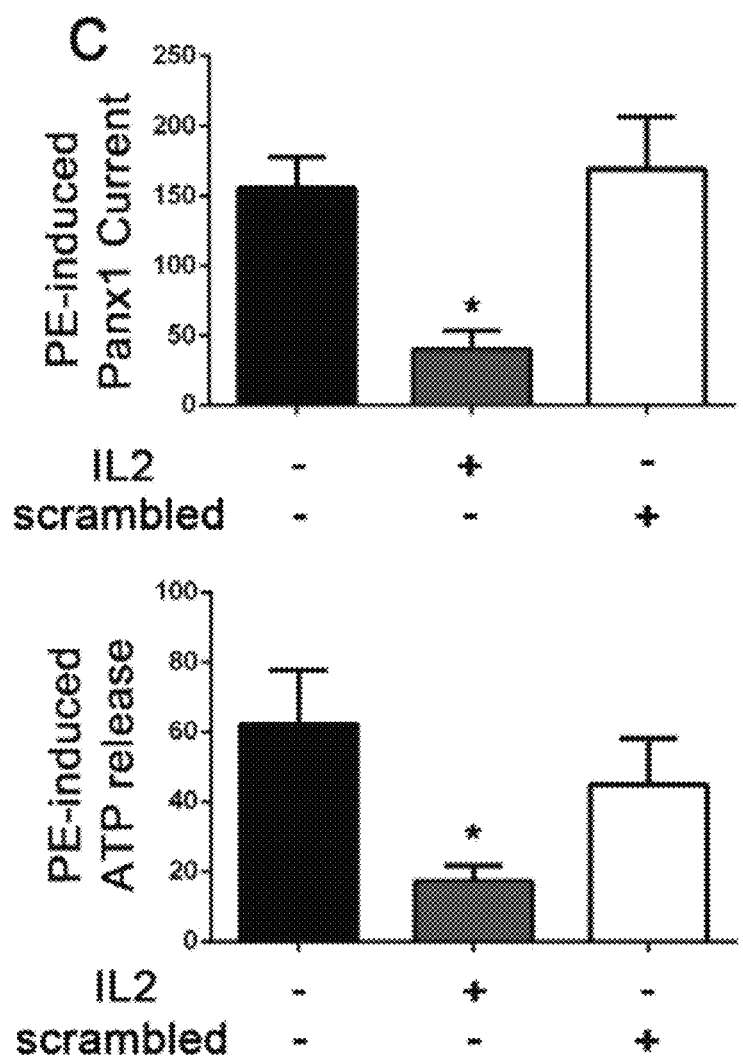
Figure 5D:
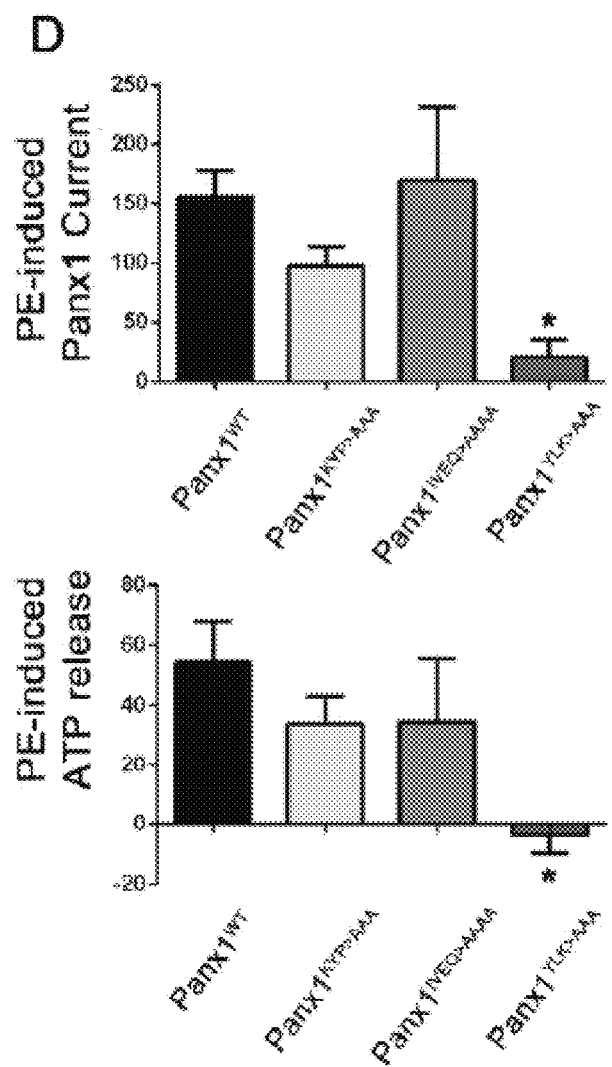
Figure 8:
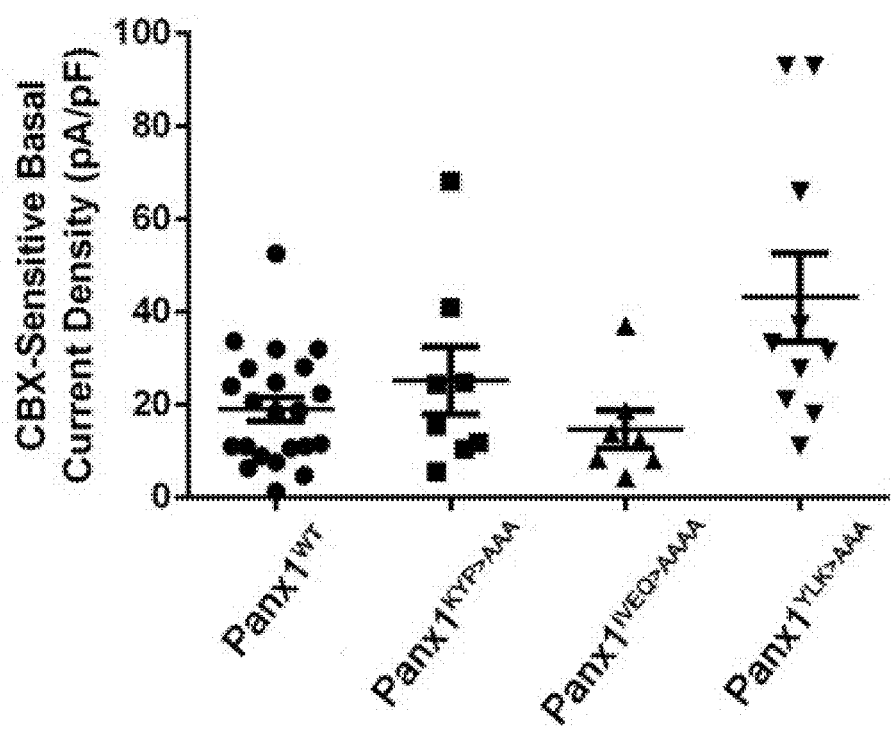
FIG. 8: Effect of mutations in the Panx1 IL2 region on channel function. Carbenoxolone-sensitive currents measured in HEK293 cells cotransfected with α1DAR and Panx1$^{WT}$, Panx1$^{KYP>AAA}$, Panx1$^{IVEQ>AAAA}$, or Panx1$^{YLK>AAA}$ showing similar Panx1 currents produced by the different Panx1 mutants in unstimulated conditions. Results are expressed in current density (pA/pF).
Figure 9A:
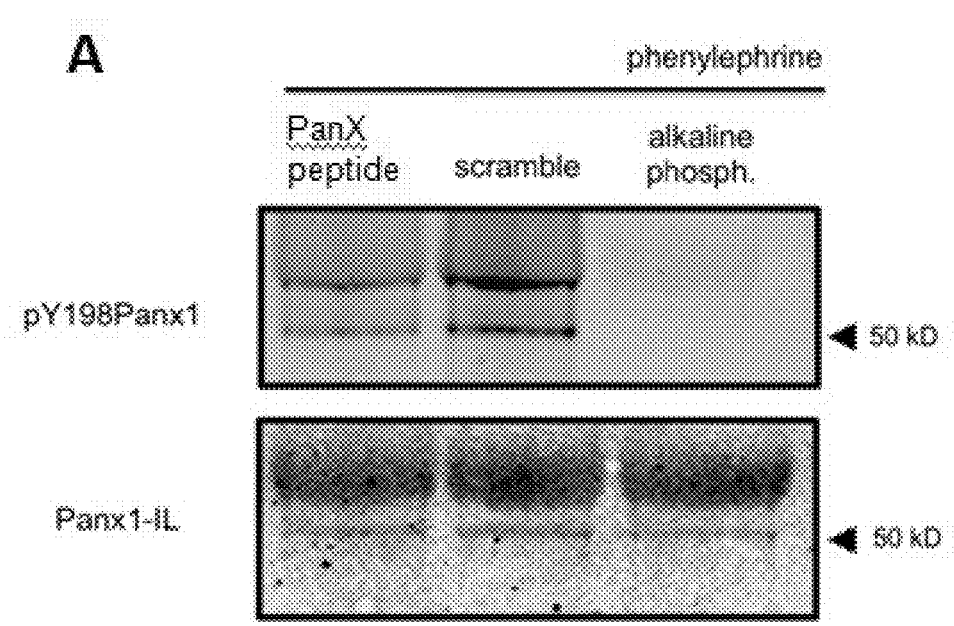
FIGS. 9 (A and B): Peptide against Pannexin1 significantly reduces hyperconstriction in treatment resistant hypertension patients by dephosphorylation of Panx1 protein: 9A comprises two blots and 9B is a graphic representation of changes in diameter of resistance arterioles isolated from hypertensive subjects with or without treatment with IL2 (PanX) peptide. The resistance arterioles were isolated from adipose tissue. Treatment resistant hypertension: >3 continue to have high blood pressure.
Figure 9B:
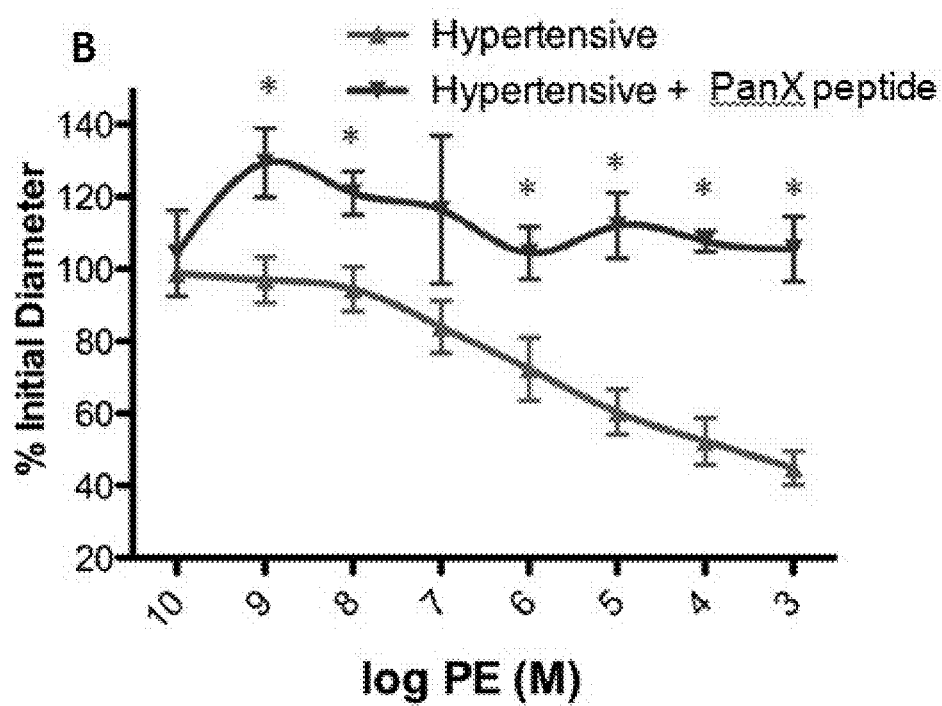
Figure 10:
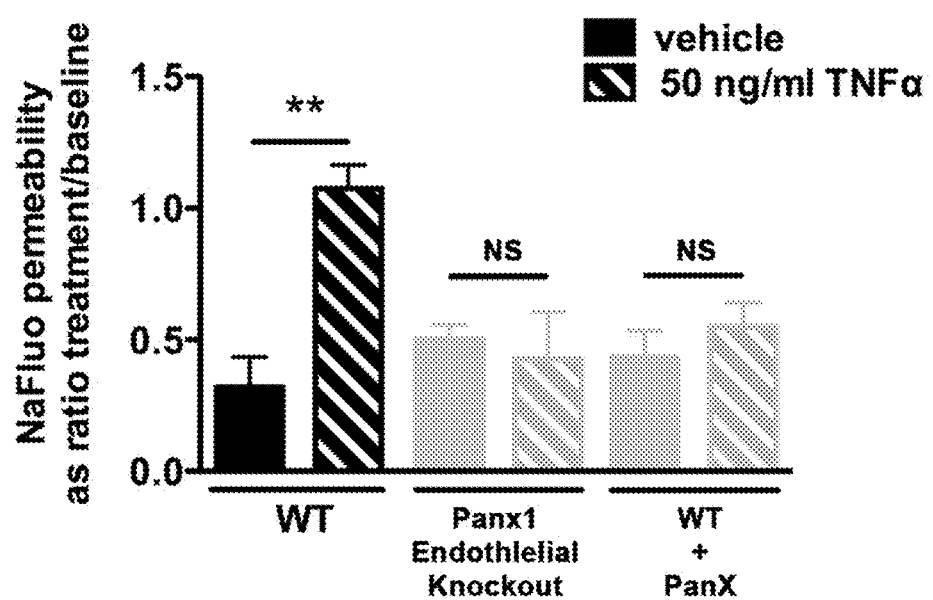
FIG. 10: IL2 (PanX) prevents TNFα-induced venous endothelial cell permeability: Permeability of endothelial cells allows leukocytes and other inflammatory cells to invade tissue and this predominantly occurs in the veins. We show here TNFα induces permeability in intact veins of wild type mice (crosshatched black bars). As predicted, knockout of Panx1 specifically from endothelium prevents TNFα induced against permeability (crosshatched gray bars, middle panel). Preincubation of WT veins with PanX peptide has an identical effect (crosshatched gray bars, right panel). The ordinate represents NaFluo permeability as ration treatment/baseline. Treatment was with 50 ng/ml TNFα or vehicle.
Figure 11A:
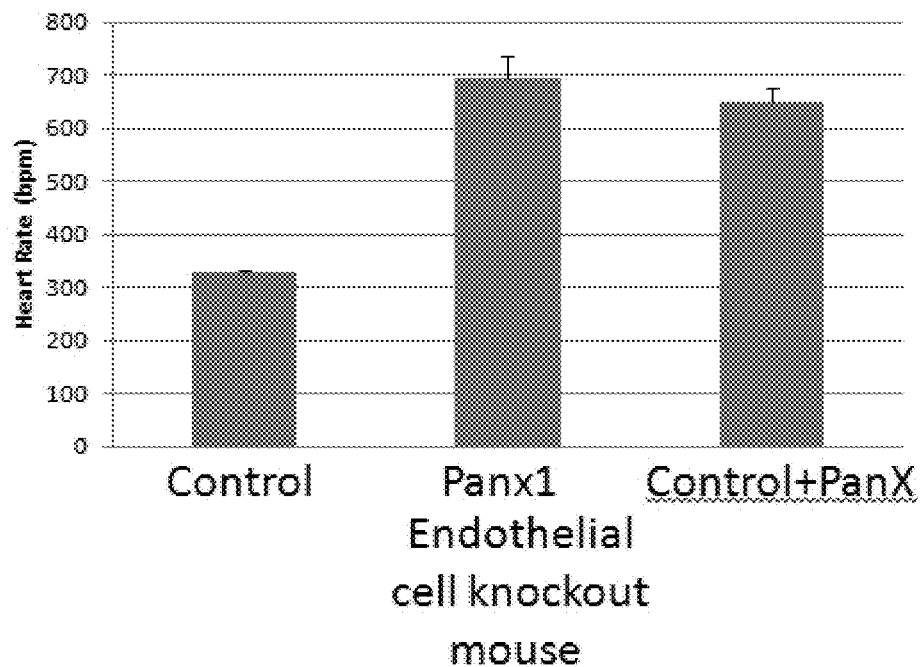
FIGS. 11 (A and B): IL2 (PanX) peptide protects against sepsis: 11A graphically demonstrates heart rate after induction of sepsis using the Cecal ligation puncture (CLP) model, a well-accepted model of sepsis in mice. Knockout of Panx1 specifically from the endothelium or treatment of mice with PanX both reversed the decreased in heat rate typically observed after induction of sepsis. 11B graphically demonstrates blood urea nitrogen after induction of sepsis using the CLP model. Knockout of Panx1 specifically from the endothelium or treatment of mice with PanX both reversed the increased level of blood urea nitrogen, which is due in large part to increased vein permeability in sepsis. The three groups in each graph are Control (left bar), Panx1 Endothelial Cell Knockout Mouse (middle bar), and Control+IL2 (PanX) Peptide treatment.
Figure 11B:
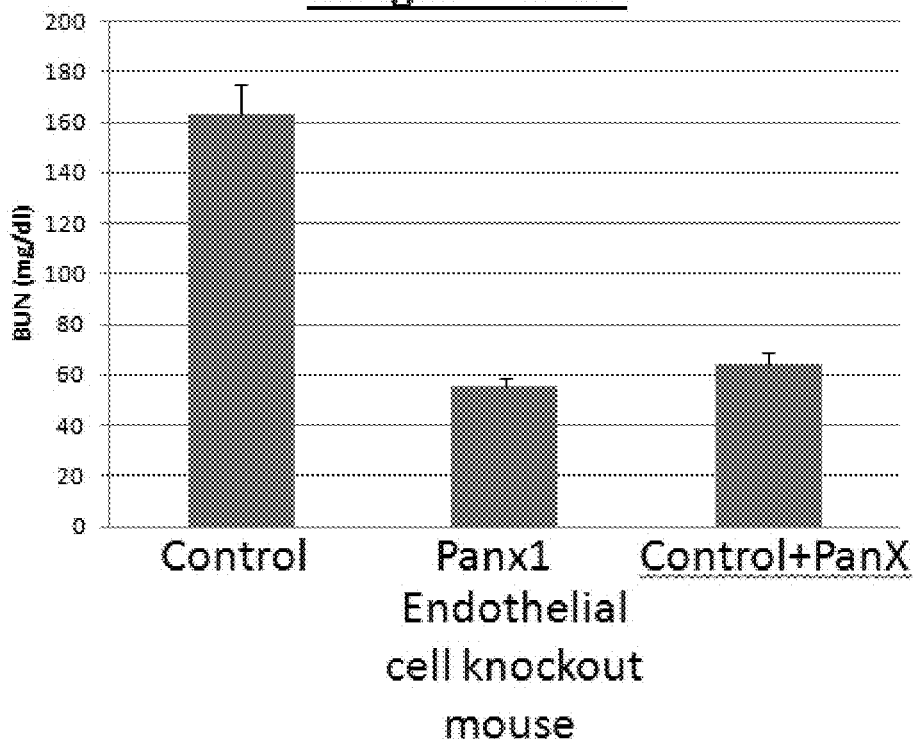

When cotransfected cells were incubated with the IL2 peptide, both phenylephrine-induced Panx1 current and ATP release were significantly decreased, whereas the scrambled version of the IL2 peptide had no effect (FIG. 5C). To better define the activating region within the Panx1 intracellular loop, we generated Panx1 mutants with alanine substitutions for selected amino acids corresponding to the IL2 sequence (aa 191 to 200): Panx1$^{KYP>AAA}$, Panx1$^{IVEQ>AAAA}$, and Panx1$^{YLK>AAA}$. We individually cotransfected each mutated construct with α1DAR into HEK293 cells and monitored phenylephrine-induced Panx1 activation. Phenylephrine stimulation of cells expressing α1DAR and either Panx1$^{KYP>AAA}$ or Panx1$^{IVEQ>AAAA}$ resulted in similar increases in Panx1 current and ATP release as were observed with the control cells expressing α1DAR and Panx1$^{WT}$ (FIG. 5D). However, HEK293 cells expressing α1DAR and Panx1$^{YLK>AAA}$ failed to increase Panx1 current and ATP release upon phenylephrine stimulation (FIG. 5D), identifying these residues as important for α1AR-dependent Panx1 activation. Importantly, the absence of phenylephrine-induced channel activation was not due to an inability of the channel to traffic to the plasma membrane or to disrupted channel function independently of phenylephrine-induced activation, because the Panx1$^{YLK>AAA}$ mutant channel produced basal CBX-sensitive currents that were not different from those detected in cells expressing the wild-type channel (FIG. 8).

Figure 5E:
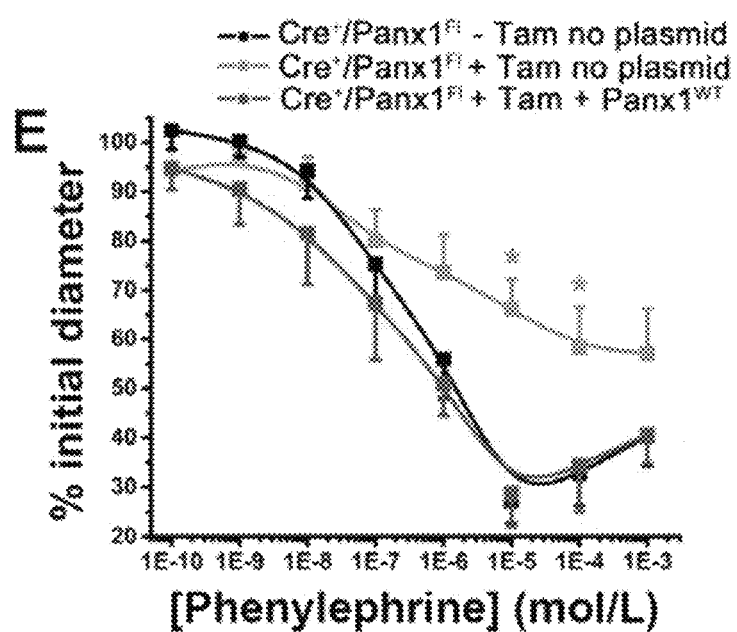
Figure 5F:
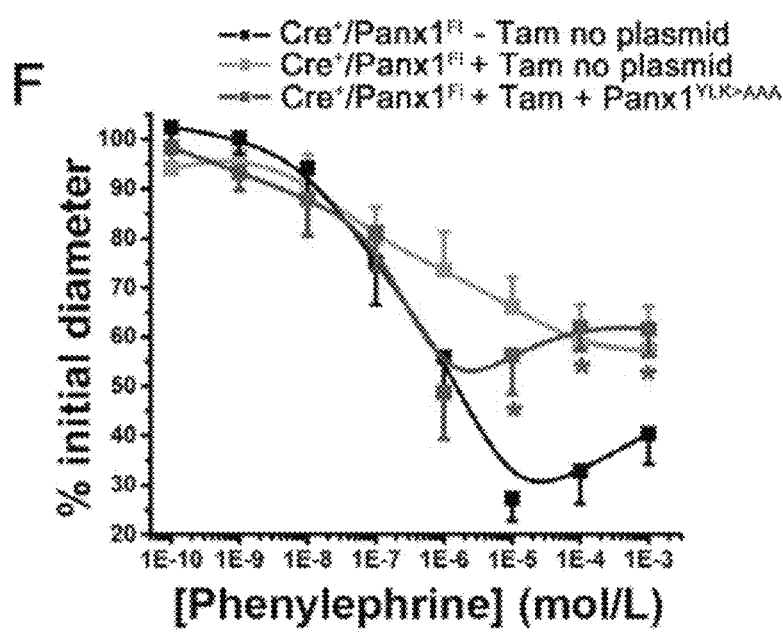

We further tested the importance of the YLK sequence within the intracellular loop of Panx1 on phenylephrine-induced vasoconstriction using rescue experiments with intact arteries from mice lacking endogenous Panx1. We reintroduced Panx1 into the SMCs of TDAs from Cre$^+$/Panx1$^{F1}$ mice that had received tamoxifen by selectively transfecting these cells with a plasmid encoding Panx1$^{WT}$. Following transfection of Panx1$^{WT}$ into these arteries, the phenylephrine-induced vasoconstriction was similar to that in control, sham-transfected arteries from Cre$^+$/Panx1$^{F1}$ mice that were not injected with tamoxifen (FIG. 5E; Table 5). Consistent with our in vitro analysis, transfection of the Panx1$^{YLK>AAA}$ mutant into SMCs of TDAs from tamoxifen-injected Cre$^+$/Panx1$^{F1}$ mice failed to rescue phenylephrine-induced constriction, and the response plateaued at a similar to amount of constriction as seen in sham-transfected TDAs from tamoxifen-injected Cre$^+$/Panx1$^{F1}$ mice (FIG. 4F; Table 5). These studies identified a molecular signature within the Panx1 intracellular loop that is essential for coordination of α1AR-dependent Panx1 channel activation in vascular SMCs and, in turn, vascular constriction.

Discussion

In the resistance vasculature, sympathetic vasoconstriction contributes to the overall control of systemic blood pressure by regulating peripheral vascular resistance. This process occurs, in part, after the release of noradrenaline from perivascular sympathetic nerves and binding to ARs located on the adjacent SMCs. This constriction occurs mainly through activation of the α1DAR isoform on SMCs. Recent work from our laboratory has implicated Panx1 channels in the control of adrenergic vasoconstriction in the peripheral vasculature; however, less is known about the molecular mechanisms controlling this event, and whether Panx1 channels are involved in response to other contractile agonists. Here, we showed using multiple in vitro, ex vivo, and in vivo models that a functional interaction exists between α1AR and Panx1, but not between Panx1 and other vasoconstricting receptors, in vascular SMCs.

The first line of evidence disclosed herein utilized a pharmacological approach with two independent, well-described Panx1 inhibitors on pressurized arteries subjected to cumulative doses of contractile agonists that are all G protein-coupled receptors (GPCRs). These results demonstrated a specific functional interaction between AR activation by phenylephrine or noradrenaline and Panx1 channels: Panx1 channel inhibition blunted agonist-induced vasoconstriction without affecting vasoconstriction elicited by serotonin and endothelin-1. In support of a purinergic role for Panx1 activity, isolated intact arteries stimulated with phenylephrine released ATP into the extracellular milieu, an effect also ablated with Panx1 inhibitors and absent in response to serotonin and endothelin-1.

In the vasculature, serotonin vasoconstriction is mostly mediated by 5HT$_{2A}$ receptors, and, in some vascular beds, by 5HT$_{1B/1D}$ receptors, and endothelin-1 induces SMC contraction upon binding to ET$_A$ receptors. The α1AR, 5HT$_{2A}$, and ET$_A$ are all G$_q$ protein-coupled receptors, leading to activation of phospholipase C and subsequent calcium release from the endoplasmic reticulum. Several studies have reported activation of Panx1 by G$_q$-coupled receptors in other cell types. For example, bradykinin is linked to Panx1-mediated ATP release from human subcutaneous fibroblasts. Histamine induces an increase in ATP release from human subcutaneous fibroblasts and from endothelial cells. Additionally, the stimulation of protease-activated receptor (PAR)-1 by thrombin is linked to ATP release from endothelial cells, and a PAR-β-dependent pathway stimulates ATP release from lung epithelial cells. These reports indicate that Panx1 may provide additional secondary signaling activation (e.g., increase in intracellular Ca$^{2+}$ concentration) through ATP release and subsequent purinergic receptor activation so as to enhance metabotropic receptor signaling. However, our results here suggested that there is specificity to this GPCR-mediated activation of Panx1, because only agonists of α1AR and not those of serotonin or endothelin receptors stimulated Panx1 channel activity, ATP release, and vasoconstriction in SMCs.

Although α1AR, 5HT$_{2A}$, and ET$_A$ are all G$_q$-coupled receptors, other downstream signaling molecules can contribute to the cellular response to their activation. For example, calcium sensitization of the contractile apparatus through Rho kinases has been described upon stimulation of various vascular beds with phenylephrine, serotonin, or endothelin-1 and Panx1-mediated ATP release has been associated to Rho kinase activity in lung epithelial cells. The Rho kinase pathway is therefore a possible target in this pathway; however, the specificity for α1AR would need elucidation. Furthermore, PE-mediated constriction has also been linked to activation of a G$_i$-cAMP-dependent signaling pathway in rat mesenteric arteries, swine renal arteries, and pharmacological evidence has demonstrated a possible interaction between α1AR and the G$_i$ pathway in cardiomyocyte contraction. Although our work shows that purinergic signaling is a key component to the α1AR vasoconstriction pathway, the mechanism linking α1AR stimulation and Panx1 channel opening requires more detailed analysis of the signaling pathways downstream of α1AR, 5HT$_{2A}$, 5HT$_{1B/1D}$, and ET$_A$.

Although our pharmacological assessment of Panx1 involvement in adrenergic vasoconstriction suggested a prominent role for the channel in this process, there are inherent limitations to the current pharmacological tools available for inhibition of pannexin channels with several blockers showing cross-inhibition with connexin hemichannels. Because of this potential confounding issue, we utilized a genetic approach by creating an inducible, SMC-specific Panx1-knockout mouse model (Cre$^+$/Panx1$^{F1}$). Because global deletion of Panx1 from birth can induce a compensatory increase in the Panx3 isoform in SMCs in the arterial circulation in the adult mouse, we used an inducible knockout model that enabled spatial and temporal control of Panx1 expression in the adult mouse. Analysis of Panx2 and Panx3 abundance in the vasculature of these mice revealed no compensatory increases in either isoform with complete deletion of Panx1 specifically from the SMC layer in adult mice. Conditional deletion of Panx1 in SMC significantly reduced the constriction to α1AR agonists, providing further support for a central role of Panx1 channels in adrenergic vasoconstriction. We noted that Panx1 deletion was more effective at reducing vasoconstriction to phenylephrine than to noradrenaline. Several studies have reported the involvement of other AR isoforms in noradrenaline-mediated responses in arteries. In particular, the α2AR and the β2AR, respectively coupled to G$_i$ and G$_s$, are found in both SMC and EC depending on the vascular bed and the species.

On the basis of these observations, we predict that noradrenaline signaling through one of the other AR isoforms, likely α2AR, is responsible for the reduced effect of Panx1 knockout on the vasoconstriction to noradrenaline compared to that produced by the more selective α1AR agonist phenylephrine. Although the postjunctional receptors involved in the noradrenergic response in TDA are unknown, the effect of SMC Panx1 knockout not only reduced phenylephrine- and noradrenaline-mediated vasoconstriction, but also resulted in a decrease of mean arterial pressure in freely moving mice. Our radiotelemetry data on Cre+/Panx1$^{F1}$ mice demonstrated a significant hypotension, which was exaggerated at night during the period of greatest sympathetic activity. These data indicate a potentially key role of SMC Panx1 channels in noradrenergic vasoconstriction and regulation of systemic blood pressure in the live animal.

Similar to pharmacological studies, genetic deletion of Panx1 from SMC prevented ATP release in response to α1AR stimulation, which is consistent with our previous work reporting a functional role for ATP release in arterial constriction to phenylephrine. Previously, we reported that degradation of extracellular ATP with apyrase and inhibition of SMC P2Y purinergic receptors with Reactive Blue-2 reduced phenylephrine-induced vasoconstriction. Although other cells composing the vascular wall, including nerves and endothelial cells, as well as circulating erythrocytes, can provide releasable pools of ATP, our pharmacological, molecular, and genetic data described here provide evidence that SMCs can also release ATP from the intact arterial wall. In addition, other nonvascular SMC release ATP, including SMCs from the colon and SMCs from the bladder. Although the mechanisms of ATP liberation from those cells are still under investigation, pannexins are present in these nonvascular SMCs.

Utilizing molecular techniques, we disrupted the α1AR-Panx1 functional interaction by screening interfering peptides that were based on Panx1 intracellular amino acid sequences. One peptide mimicking a sequence in the Panx1 intracellular loop (IL2) inhibited α1AR-dependent vasoconstriction and ATP release from intact arteries. Although consistent with the pharmacological inhibition and genetic deletion of Panx1, the pharmacological inhibitors 10Panx1 and probenecid (FIG. 1) were more effective in reducing the phenylephrine-induced constriction compared to the IL2 peptide (FIG. 4) or the knock down of Panx1 in our conditional KO mouse model (FIG. 2). This difference is most likely due to inherent nonspecific effect of $^{10}$Panx1 and probenecid. Intraperitoneal injection of this IL2 peptide acutely reduced mean arterial pressure in C57Bl/6 mice, consistent with our inducible conditional KO model.

To further define the α1AR-Panx1 interaction, we turned to a heterologous cell culture system expressing α1DAR and Panx1. With this system, we observed enhanced ATP release and CBX-sensitive Panx1 currents following phenylephrine application; these effects were inhibited with the same IL2 peptide that blunted phenylephrine-induced vasoconstriction and ATP release from intact arteries. Because the IL2 peptide mimics the endogenous Panx1 sequence in position 191-200, we progressively substituted amino acids in this region of full-length Panx1 with alanine residues to more precisely define the motif required for channel activation by α1AR stimulation. Utilizing our heterologous system, we identified a three amino acid stretch ($^{198}$YLK$^{200}$) in the Panx1 intracellular loop that, when mutated, renders the channel insensitive to α1AR-dependent activation. Lastly, using in situ transfection, we rescued the α1AR-dependent vasoconstriction in vessels by heterologous expression of wild-type Panx1 in the SMC of intact arteries from Cre+/Panx1$^{F1}$ mice; by contrast, the Panx1$^{YLK>AAA}$ mutant did not rescue α1AR-dependent vasoconstriction.

Although the exact mechanism by which the α1AR functionally interacts with the Panx1 YLK motif remains unclear, sequence analysis may provide initial insight. The region of Panx1 containing the amino acids 191-200 has a high propensity to form α-helix structure, which are known to constitute a fundamental recognition element in many protein-protein interactions. Interestingly, α-helix-mediated protein-protein interactions are practical targets for chemical design of small molecular inhibitors. Additionally, there is a region containing several proline residues proximal to the IL2 sequence in the Panx1 intracellular loop. This may prove to be important because proline-rich regions can introduce hinge points in the tertiary structure of proteins, creating flexibility and providing hallmark locations where protein-protein interactions occur. In agreement, connexins, which have a similar topology to Panx1, contain a proline-rich region in their C-terminal tail, which is the main site of interaction with protein partners. Another intriguing aspect of the YLK motif is the presence of a tyrosine, which could be a potential regulatory phosphorylation site. Recent evidence in support of Panx1 regulation by kinases has been reported in several cell types, including kinases of the Src in hippocampal neurons and in macrophages. However, direct evidence of Panx1 phosphorylation has only been provided in skeletal myocytes, in which increased amounts of Panx1 phosphoserine and phosphothreonine are associated with Panx1 activity in electrically stimulated rat skeletal muscles. Several kinases are activated in the α1AR signaling pathway, including kinases from the Rho kinase family, PKA (cyclic AMP-dependent protein kinase), PKC (protein kinase C), and Src family of protein tyrosine kinases. It is thus tempting to speculate that Panx1 may be phosphorylated at Tyr$^{198}$ by a kinase activated upon α1AR stimulation.

Our data demonstrated that α1AR and Panx1 participate in vasoconstriction through a unique functional interaction in vascular SMCs that could be important for adrenergic control of blood pressure. Targeting this signaling mechanism may therefore provide an approach to intervene in blood pressure disorders. To this end, several Panx1 inhibitors have been successfully used in vivo in model animals to target Panx1-mediated signaling processes, including the FDA-approved gout remedy probenecid. In addition, another Panx1 channel inhibitor, mefloquine, induces hypotension when injected into anaesthetized guinea pigs. Similar to probenecid, mefloquine is another FDA-approved drug to prevent and treat malaria, and it is interesting to note that this drug has a listed side-effect of hypotension. Trovafloxacin, an FDA-approved antibiotic that was later removed from the market due to its side-effects, can also inhibit Panx1 channels. Our work suggested that it may be possible to target the YLK sequence of Panx1, either with peptides (such as our IL2 peptide) or through a small molecule approach and targeting this sequence which may provide a highly specific mechanism for therapeutically regulating vasoconstriction and blood pressure. Collectively, this work provides new insight into the basis of α1AR-mediated vasoconstriction by indicating that noradrenergic signaling activates Panx1 to promote purinergic signaling and that this signaling mechanism may have a potentially key role in blood pressure homeostasis.

The development of small peptide inhibitors as biomedical research tools and as therapeutic molecules has many advantages. First, the synthesis of small peptide inhibitors is economical. Due to their small size, ease of synthesis and modification, and ease for optimization and evaluation, small peptides can be efficiently scaled in production. Second, small peptide inhibitors have greater target specificity and less overall toxicity when compared with small molecule inhibitors. Third, the use of peptides as therapeutic agents allows for greater pharmacodynamic control and customization in biological systems since peptides can be metabolically cleaved and rapidly cleared from the body. Based on the pharmacodynamics characteristics, small peptides do not accumulate in body organs, which minimize their toxicity and unwanted side effects. They additionally do not intrinsically cause serious immune responses and do not cross the blood brain barrier unless modified to do so. IL2 is therefore a valuable and effective small peptide inhibitor of pannexin1 channels that has many beneficial pharmacological properties. Additionally, IL2 harbors a novel TAT (transactivator of transcription) consensus sequence on the peptide C-terminus, a non-pathological subunit of the human immunodeficiency virus (HIV), which strongly potentiates peptide delivery across cellular membranes to enhance efficacy.

To date, only one other pannexin1 inhibitory peptide exists ($^{10}$Panx1). However, this peptide has limited efficacy in many biological systems and does not target a well-validated regulatory region of pannexin1. Other pharmacological methods for inhibiting the release of bioactive molecules from pannexin1 channels consist of small molecule inhibitors. In a majority of cases, these small molecules have poorly defined pharmacological mechanisms and exhibit non-specific interactions with connexin gap junction forming proteins, an important protein that regulates cardiac muscle contraction, neural communication, and embryonic/organ development. Small molecule inhibitors of pannexin 1 include carbenoxolone, mefloquine, 5-nitro-2-(3-phenylpropylamino)benzoic acid, and probenecid. There is an active debate within the pannexin field to define which small molecule inhibitors are specific pannexin1 inhibitors. Current field standards for specifically demonstrating pannexin1 inhibition consist of the combinatorial use of multiple small molecule inhibitors in tandem with genetic deletion methods including small interfering RNAs and genetically engineered mouse strains. Therefore, use of UVAPx-1 as a novel research tool has an extraordinary potential to eliminate many inefficiencies and unnecessary costs currently afflicting the biomedical research community.

There are important clinical and commercial implications of the invention disclosed herein. Pannexin1 channels have been implicated in a number of diseases and disorders. IL2 (UVAPx-1) is an effective and targeted peptide inhibitor that could have a significant impact as a biomedical research tool for studying the role of pannexins in diseases associated with hypertension, autoimmunity, inflammation, ischemia, stroke, and cancer. Due to the beneficial pharmacological properties of small peptide inhibitors IL2 (UVAPx-1) has high clinical potential as an innovative pharmacotherapy for pathologies pertaining to essential hypertension, treatment resistant hypertension, vascular sympathetic nerve hyperactivity, vascular dysfunction, stroke, aberrant immune cell recruitment from the blood into body tissues, and pathological TNF-alpha dependent inflammatory responses. (See also FIGS. 7-11 and Tables 1-7)).

TABLE 1

Effect of probenecid and $^{10}$Panx1 on TDA constriction in response to phenylephrine, noradrenaline, serotonin, or endothelin-1. $EC_{50}$ and $E_{MAX}$ were calculated using the cumulative concentration response curves showed in FIG. 1A through D. $EC_{50}$ represents the concentration needed to produce 50% of the maximum effect ($E_{MAX}$). $E_{MAX}$ is expressed as the percentage of maximal diameter. Data are presented as mean ± sem, *indicates $p < 0.05$ compared to control using a Kruskal-Wallis test (n = 5-7).

|  | Phenylephrine | | | Noradrenaline | | |
| --- | --- | --- | --- | --- | --- | --- |
|  | Control | Probenecid | $^{10}$Panx1 | Control | Probenecid | $^{10}$Panx1 |
| $EC_{50}$ (μmol/L) | 1.21 ± 0.27 | 2.71 ± 1.36 | 2.38 ± 0.53 | 0.56 ± 0.25 | 1.30 ± 0.65 | 1.61 ± 0.49 |
| $E_{MAX}$ | 41.1 ± 2.21 | 72.6 ± 3.51* | 60.6 ± 5.80* | 33.3 ± 1.04 | 74.9 ± 3.04* | 73.4 ± 10.6* |

|  | Serotonin | | | Endothelin-1 | | |
| --- | --- | --- | --- | --- | --- | --- |
|  | Control | Probenecid | $^{10}$Panx1 | Control | Probenecid | $^{10}$Panx1 |
| $EC_{50}$ (nmol/L) | 50.8 ± 18.9 | 83.3 ± 8.42 | 47.9 ± 23.1 | 4.57 ± 0.88 | 12.8 ± 4.05 | 6.53 ± 1.36 |
| $E_{MAX}$ | 34.8 ± 2.66 | 39.5 ± 3.29 | 30.9 ± 4.92 | 41.9 ± 4.82 | 34.6 ± 4.50 | 41.5 ± 3.91 |

TABLE 2

Contractile properties of TDAs isolated from Cre$^-$/Panx1$^{WT}$ mice, Cre$^-$/Panx1$^{Fl}$ mice, Cre$^+$/Panx1$^{WT}$ mice, or Cre$^+$/Panx1$^{Fl}$ mice.

|  | Cre$^-$/Panx1$^{WT}$ | Cre$^-$/Panx1$^{FL}$ | Cre$^+$/Panx1$^{WT}$ | Cre$^+$/Panx1$^{FL}$ |
| --- | --- | --- | --- | --- |
|  | Phenylephrine | | | |
| $EC_{50}$ (μmol/L) | 0.66 ± 0.13 | 0.64 ± 0.37 | 1.79 ± 1.13 | 7.84 ± 5.60 |
| $E_{MAX}$ | 51.8 ± 2.66 | 46.3 ± 5.94 | 53.5 ± 4.91 | 69.1 ± 3.06* |
|  | Noradrenaline | | | |
| $EC_{50}$ (μmol/L) | 6.28 ± 1.45 | 10.3 ± 1.3 | 6.78 ± 3.20 | 50.5 ± 24.8 |
| $E_{MAX}$ | 41.4 ± 5.10 | 45.6 ± 5.40 | 48.2 ± 1.82 | 56.4 ± 5.61$^\#$ |
|  | Serotonin | | | |
| $EC_{50}$ (nmol/L) | 23.8 ± 5.07 | 65.2 ± 40.9 | 40.7 ± 12.2 | 14.2 ± 5.53 |
| $E_{MAX}$ | 36.1 ± 2.68 | 30.4 ± 1.78 | 40.1 ± 4.59 | 38.2 ± 5.60 |
|  | Endothelin-1 | | | |
| $EC_{50}$ (nmol/L) | 18.4 ± 10.9 | 3.77 ± 0.56 | 5.64 ± 2.94 | 30.1 ± 14.6 |
| $E_{MAX}$ | 41.8 ± 4.95 | 42.2 ± 6.50 | 42.5 ± 4.82 | 38.9 ± 6.90 |

The $EC_{50}$ and $E_{MAX}$ are calculated from the data presented in FIG. 2C through F.
$EC_{50}$ represents the concentration needed to produce 50% of the maximum effect ($E_{MAX}$).
$E_{MAX}$ is expressed as the percentage of maximal diameter.
Data are presented as mean ± sem.
*indicates $p < 0.05$, and
$^\#$indicates $p < 0.07$ compared to Cre$^-$/Panx1$^{WT}$ using a Kruskal Wallis test (n = 4-16).

TABLE 3

Amino acid sequences of intracellular loop and C-terminal region peptides. All listed peptides were linked with a TAT sequence (YGRKKQRRR). The numbers indicate the peptide location in the mPanx1 amino acid sequence. The CT1 peptide has previously been published to inhibit NMDA-mediated Panx1 opening.

| | amino acid sequence (mPanx1) |
|---|---|
| IL1 | 178-VGQSLWEISE-187 (SEQ ID NO: 4) |
| IL2 | 191-KYPIVEQYLK-200 (SEQ ID NO: 1) |
| CT1 | 305-RRLKVYEILPTFDVLH-318 (SEQ ID NO: 5) |
| CT2 | 381-IPTSLQTKGE-390 (SEQ ID NO: 6) |
| Scrambled IL2 | IYLYVEQKPY (SEQ ID NO: 7) |

TABLE 4

Effect of four Panx1 mimetic peptides on constriction of TDAs in response to phenylephrine, noradrenaline, serotonin, or endothelin-1. The $EC_{50}$ and $E_{MAX}$ are calculated from the data presented in FIG. 4B through H. $EC_{50}$ represents the concentration needed to produce 50% of the maximum effect ($E_{Max}$). $E_{MAX}$ is expressed as the percentage of maximal diameter. Data are presented as mean ± sem, * indicates $p < 0.05$ compared to no peptide using a Mann-Whitney test (n = 4-7).

| | Phenylephrine | | | |
|---|---|---|---|---|
| | No peptide | CT1 | No peptide | CT2 |
| $EC_{50}$ (µmol/L) | 1.67 ± 1.13 | 1.43 ± 0.59 | 1.06 ± 0.32 | 4.78 ± 3.93 |
| $E_{MAX}$ | 52.5 ± 3.30 | 50.7 ± 9.08 | 49.0 ± 2.49 | 52.3 ± 4.86 |

| | Phenylephrine | | | |
|---|---|---|---|---|
| | No peptide | IL1 | No peptide | IL2 |
| $EC_{50}$ (µmol/L) | 3.26 ± 1.53 | 1.14 ± 0.43 | 1.15 ± 0.35 | 0.57 ± 0.22 |
| $E_{MAX}$ | 40.1 ± 5.10 | 32.3 ± 3.81 | 47.70 ± 1.6 | 68.6 ± 5.11* |

| | Noradrenaline | | Serotonin | | Endothelin-1 | |
|---|---|---|---|---|---|---|
| | No peptide | IL2 | No peptide | IL2 | No peptide | IL2 |
| $EC_{50}$ (nmol/L) | 0.49 ± 0.42 | 2.00 ± 1.90 | 11.7 ± 1.65 | 5.03 ± 0.82* | 6.01 ± 3.74 | 0.88 ± 0.39 |
| $E_{MAX}$ | 27.1 ± 4.69 | 53.4 ± 7.00* | 38.6 ± 5.70 | 36.7 ± 3.52 | 38.2 ± 6.67 | 41.9 ± 3.73 |

TABLE 5

Effect of transfection of thoracodorsal arteries with $Panx1^{WT}$ or $Panx1^{YLK>AAA}$ on phenylephrine-induced constriction.

| | Phenylephrine | | | |
|---|---|---|---|---|
| | $Cre^+/Panx1^{FL}$ No tamoxifen | $Cre^+/Panx1^{FL}$ With tamoxifen | $Cre^+/Panx1^{FL}$ + $Panx1^{WT}$ | $Cre^+/Panx1^{FL}$ + $Panx1^{YLK>AAA}$ |
| $EC_{50}$ (µmol/L) | 0.64 ± 0.23 | 1.13 ± 0.77 | 0.45 ± 0.33 | 0.63 ± 0.53 |
| $E_{MAX}$ | 32.9 ± 4.85 | 57.5 ± 9.20*# | 34.2 ± 6.15 | 56.9 ± 5.84*# |

The $EC_{50}$ and $E_{MAX}$ are calculated from the data presented in FIG. 4E and F.
$EC_{50}$ represents the concentration needed to produce 50% of the maximum effect ($E_{MAX}$).
$E_{MAX}$ is expressed as the percentage of maximal diameter.
Data are presented as mean ± sem.
*indicates $p < 0.05$ in comparison to no tamoxifen, and
indicates $p < 0.05$ in comparison to $Cre^+/Panx1^{FL}$ + $Panx1^{WT}$ using a Kruskal Wallis test.

TABLE 6

Contractile properties of aortic rings isolated from control Cre+/Panx1$^{Fl}$ mice and Cre+/Panx1$^{Fl}$ injected with tamoxifen for ten days.

| | Phenylephrine | |
| --- | --- | --- |
| | Cre+/Panx1$^{FL}$ Peanut oil | Cre+/Panx1$^{FL}$ With tamoxifen |
| EC$_{50}$ (µmol/L) | 3.39 ± 0.38 | 3.20 ± 0.32 |
| E$_{MAX}$ | 368.8 ± 78.7 | 343.4 ± 69.4 |

The EC$_{50}$ and E$_{MAX}$ are calculated from the data presented in FIG. 6D.
EC$_{50}$ represents the concentration needed to produce 50% of the maximum effect (E$_{MAX}$).
E$_{MAX}$ is expressed as the percentage of constriction to KCl.
Data are presented as mean ± sem.

TABLE 7

Effect of scrambled IL2 peptide and TAT peptide on constriction of TDAs in response to phenylephrine.

| | Phenylephrine | | |
| --- | --- | --- | --- |
| | No peptide | Scrambled IL2 | TAT |
| EC$_{50}$ (µmol/L) | 2.98 ± 0.68 | 2.87 ± 1.97 | 1.63 ± 0.35 |
| E$_{MAX}$ | 39.7 ± 6.75 | 47.5 ± 2.17 | 32.0 ± 6.21 |

The EC$_{50}$ and E$_{MAX}$ are calculated from the data presented in FIG. 7B.
EC$_{50}$ represents the concentration needed to produce 50% of the maximum effect (E$_{MAX}$).
E$_{MAX}$ is expressed as the percentage of maximal diameter.
Data are presented as mean ± sem.

Headings are included herein for reference and to aid in locating certain sections. These headings are not intended to limit the scope of the concepts described therein under, and these concepts may have applicability in other sections throughout the entire specification.

The disclosures of each and every patent, patent application, and publication cited herein are hereby incorporated by reference herein in their entirety.

While this invention has been disclosed with reference to specific embodiments, it is apparent that other embodiments and variations of this invention may be devised by others skilled in the art without departing from the true spirit and scope of the invention.

BIBLIOGRAPHY

1. G. Burnstock, V. Ralevic, Purinergic signaling and blood vessels in health and disease. Pharmacol Rev 66, 102-192 (2014).
2. G. Burnstock, Dual control of vascular tone and remodelling by ATP released from nerves and endothelial cells. Pharmacol Rep 60, 12-20 (2008).
3. A. W. Lohman, M. Billaud, B. E. Isakson, Mechanisms of ATP release and signalling in the blood vessel wall. Cardiovasc Res 95, 269-280 (2012).
4. M. Billaud, A. W. Lohman, A. C. Straub, R. Looft-Wilson, S. R. Johnstone, C. A. Araj, A. K. Best, F. B. Chekeni, K. S. Ravichandran, S. Penuela, D. W. Laird, B. E. Isakson, Pannexin1 regulates alpha1-adrenergic receptor-mediated vasoconstriction. Circulation research 109, 80-85 (2011).
5. Y. Panchin, I. Kelmanson, M. Matz, K. Lukyanov, N. Usman, S. Lukyanov, A ubiquitous family of putative gap junction molecules. Curr Biol 10, R473-474 (2000).
6. G. E. Sosinsky, D. Boassa, R. Dermietzel, H. S. Duffy, D. W. Laird, B. MacVicar, C. C. Naus, S. Penuela, E. Scemes, D. C. Spray, R. J. Thompson, H. B. Zhao, G. Dahl, Pannexin channels are not gap junction hemichannels. Channels (Austin) 5, 193-197 (2011).
7. G. Spagnol, P. L. Sorgen, D. C. Spray, Structural order in Pannexin 1 cytoplasmic domains. Channels 8, (2014).
8. M. R. Yen, M. H. Saier, Jr., Gap junctional proteins of animals: the innexin/pannexin superfamily. Prog Biophys Mol Biol 94, 5-14 (2007).
9. S. R. Bond, C. C. Naus, The pannexins: past and present. Front Physiol 5, 58 (2014).
10. S. Penuela, R. Bhalla, X. Q. Gong, K. N. Cowan, S. J. Celetti, B. J. Cowan, D. Bai, Q. Shao, D. W. Laird, Pannexin 1 and pannexin 3 are glycoproteins that exhibit many distinct characteristics from the connexin family of gap junction proteins. Journal of cell science 120, 3772-3783 (2007).
11. A. W. Lohman, M. Billaud, A. C. Straub, S. R. Johnstone, A. K. Best, M. Lee, K. Barr, S. Penuela, D. W. Laird, B. E. Isakson, Expression of pannexin isoforms in the systemic murine arterial network. Journal of vascular research 49, 405-416 (2012).
12. F. B. Chekeni, M. R. Elliott, J. K. Sandilos, S. F. Walk, J. M. Kinchen, E. R. Lazarowski, A. J. Armstrong, S. Penuela, D. W. Laird, G. S. Salvesen, B. E. Isakson, D. A. Bayliss, K. S. Ravichandran, Pannexin 1 channels mediate 'find-me' signal release and membrane permeability during apoptosis. Nature 467, 863-867 (2010).
13. I. K. Poon, Y. H. Chiu, A. J. Armstrong, J. M. Kinchen, I. J. Juncadella, D. A. Bayliss, K. S. Ravichandran, Unexpected link between an antibiotic, pannexin channels and apoptosis. Nature 507, 329-334 (2014).
14. S. E. Adamson, N. Leitinger, The role of pannexin1 in the induction and resolution of inflammation. FEBS Lett 588, 1416-1422 (2014).
15. N. L. Weilinger, V. Maslieieva, J. Bialecki, S. S. Sridharan, P. L. Tang, R. J. Thompson, Ionotropic receptors and ion channels in ischemic neuronal death and dysfunction. Acta Pharmacol Sin 34, 39-48 (2013).
16. M. Sridharan, S. P. Adderley, E. A. Bowles, T. M. Egan, A. H. Stephenson, M. L. Ellsworth, R. S. Sprague, Pannexin 1 is the conduit for low oxygen tension-induced ATP release from human erythrocytes. Am J Physiol Heart Circ Physiol 299, H1146-1152 (2010).
17. B. E. Isakson, R. J. Thompson, Pannexin-1 as a potentiator of ligand-gated receptor signaling. Channels (Austin) 8, (2014).
18. A. W. Lohman, B. E. Isakson, Differentiating connexin hemichannels and pannexin channels in cellular ATP release. FEBS Lett 588, 1379-1388 (2014).
19. J. K. Sandilos, D. A. Bayliss, Physiological mechanisms for the modulation of pannexin 1 channel activity. The Journal of physiology 590, 6257-6266 (2012).
20. S. Godecke, C. Roderigo, C. R. Rose, B. H. Rauch, A. Godecke, J. Schrader, Thrombin-induced ATP release from human umbilical vein endothelial cells. American journal of physiology. Cell physiology 302, C915-923 (2012).
21. N. L. Weilinger, P. L. Tang, R. J. Thompson, Anoxia-induced NMDA receptor activation opens pannexin channels via Src family kinases. The Journal of neuroscience: the official journal of the Society for Neuroscience 32, 12579-12588 (2012).
22. A. R. Pinheiro, D. Paramos-de-Carvalho, M. Certal, M. A. Costa, C. Costa, M. T. Magalhaes-Cardoso, F. Ferreirinha, J. Sevigny, P. Correia-de-Sa, Histamine induces ATP release from human subcutaneous fibroblasts, via pannexin-1 hemichannels, leading to Ca2+ mobilization and cell proliferation. The Journal of biological chemistry 288, 27571-27583 (2013).

23. R. Iglesias, S. Locovei, A. Roque, A. P. Alberto, G. Dahl, D. C. Spray, E. Scemes, P2×7 receptor-Pannexin1 complex: pharmacology and signaling. American journal of physiology. Cell physiology 295, C752-760 (2008).

24. M. Zhang, N. A. Piskuric, C. Vollmer, C. A. Nurse, P2Y2 receptor activation opens pannexin-1 channels in rat carotid body type II cells: potential role in amplifying the neurotransmitter ATP. The Journal of physiology 590, 4335-4350 (2012).

25. W. Silverman, S. Locovei, G. Dahl, Probenecid, a gout remedy, inhibits pannexin 1 channels. American journal of physiology. Cell physiology 295, C761-767 (2008).

26. P. Pelegrin, A. Surprenant, Pannexin-1 mediates large pore formation and interleukin-1beta release by the ATP-gated P2×7 receptor. The EMBO journal 25, 5071-5082 (2006).

27. A. Tanoue, Y. Nasa, T. Koshimizu, H. Shinoura, S. Oshikawa, T. Kawai, S. Sunada, S. Takeo, G. Tsujimoto, The alpha(1D)-adrenergic receptor directly regulates arterial blood pressure via vasoconstriction. J Clin Invest 109, 765-775 (2002).

28. E. Vives, P. Brodin, B. Lebleu, A truncated HIV-1 Tat protein basic domain rapidly translocates through the plasma membrane and accumulates in the cell nucleus. J Biol Chem 272, 16010-16017 (1997).

29. J. Howl, I. D. Nicholl, S. Jones, The many futures for cell-penetrating peptides: how soon is now? Biochem Soc Trans 35, 767-769 (2007).

30. J. K. Sandilos, Y. H. Chiu, F. B. Chekeni, A. J. Armstrong, S. F. Walk, K. S. Ravichandran, D. A. Bayliss, Pannexin 1, an ATP release channel, is activated by caspase cleavage of its pore-associated C terminal autoinhibitory region. The Journal of biological chemistry, (2012).

31. A. W. Lohman, J. L. Weaver, M. Billaud, J. K. Sandilos, R. Griffiths, A. C. Straub, S. Penuela, N. Leitinger, D. W. Laird, D. A. Bayliss, B. E. Isakson, S-nitrosylation inhibits pannexin 1 channel function. The Journal of biological chemistry 287, 39602-39612 (2012).

32. W. Ma, H. Hui, P. Pelegrin, A. Surprenant, Pharmacological characterization of pannexin-1 currents expressed in mammalian cells. J Pharmacol Exp Ther 328, 409-418 (2009).

33. W. F. Jackson, E. M. Boerman, E. J. Lange, S. S. Lundback, K. D. Cohen, Smooth muscle alpha1D-adrenoceptors mediate phenylephrine-induced vasoconstriction and increases in endothelial cell Ca2+ in hamster cremaster arterioles. Br J Pharmacol 155, 514-524 (2008).

34. E. B. Westcott, S. S. Segal, Ageing alters perivascular nerve function of mouse mesenteric arteries in vivo. The Journal of physiology 591, 1251-1263 (2013).

35. S. W. Watts, Serotonin-induced contraction in mesenteric resistance arteries: signaling and changes in deoxycorticosterone acetate-salt hypertension. Hypertension 39, 825-829 (2002).

36. S. W. Watts, R. P. Davis, 5-hydroxtryptamine receptors in systemic hypertension: an arterial focus. Cardiovasc Ther 29, 54-67 (2011).

37. P. B. Hill, K. A. Dora, A. D. Hughes, C. J. Garland, The involvement of intracellular Ca(2+) in 5-HT(1B/1D) receptor-mediated contraction of the rabbit isolated renal artery. Br J Pharmacol 130, 835-842 (2000).

38. L. N. Pierre, A. P. Davenport, Endothelin receptor subtypes and their functional relevance in human small coronary arteries. Br J Pharmacol 124, 499-506 (1998).

39. D. Rizzoni, E. Porteri, A. Piccoli, M. Castellano, G. Bettoni, G. Pasini, E. Agabiti-Rosei, The vasoconstriction induced by endothelin-1 is mediated only by ET(A) receptors in mesenteric small resistance arteries of spontaneously hypertensive rats and Wistar Kyoto rats. J Hypertens 15, 1653-1657 (1997).

40. A. R. Pinheiro, D. Paramos-de-Carvalho, M. Certal, C. Costa, M. T. Magalhaes-Cardoso, F. Ferreirinha, M. A. Costa, P. Correia-de-Sa, Bradykinin-induced Ca2+ signaling in human subcutaneous fibroblasts involves ATP release via hemichannels leading to P2Y12 receptors activation. Cell Commun Signal 11, 70 (2013).

41. L. Seminario-Vidal, S. Kreda, L. Jones, W. O'Neal, J. Trejo, R. C. Boucher, E. R. Lazarowski, Thrombin promotes release of ATP from lung epithelial cells through coordinated activation of rho- and Ca2+-dependent signaling pathways. The Journal of biological chemistry 284, 20638-20648 (2009).

42. L. Seminario-Vidal, S. F. Okada, J. I. Sesma, S. M. Kreda, C. A. van Heusden, Y. Zhu, L. C. Jones, W. K. O'Neal, S. Penuela, D. W. Laird, R. C. Boucher, E. R. Lazarowski, Rho signaling regulates pannexin 1-mediated ATP release from airway epithelia. The Journal of biological chemistry 286, 26277-26286 (2011).

43. T. Kitazawa, K. Kitazawa, Size-dependent heterogeneity of contractile Ca2+ sensitization in rat arterial smooth muscle. The Journal of physiology 590, 5401-5423 (2012).

44. K. Momotani, M. V. Artamonov, D. Utepbergenov, U. Derewenda, Z. S. Derewenda, A. V. Somlyo, p63RhoGEF couples Galpha(q/11)-mediated signaling to Ca2+ sensitization of vascular smooth muscle contractility. Circulation research 109, 993-1002 (2011).

45. M. H. Tsai, M. J. Jiang, Rho-kinase-mediated regulation of receptor-agonist-stimulated smooth muscle contraction. Pflugers Arch 453, 223-232 (2006).

46. K. Budzyn, M. Paull, P. D. Marley, C. G. Sobey, Segmental differences in the roles of rho-kinase and protein kinase C in mediating vasoconstriction. J Pharmacol Exp Ther 317, 791-796 (2006).

47. G. Loirand, V. Sauzeau, P. Pacaud, Small G proteins in the cardiovascular system: physiological and pathological aspects. Physiol Rev 93, 1659-1720 (2013).

48. M. V. Artamonov, K. Momotani, A. Stevenson, D. R. Trentham, U. Derewenda, Z. S. Derewenda, P. W. Read, J. S. Gutkind, A. V. Somlyo, Agonist-induced Ca2+ sensitization in smooth muscle: redundancy of Rho guanine nucleotide exchange factors (RhoGEFs) and response kinetics, a caged compound study. The Journal of biological chemistry 288, 34030-34040 (2013).

49. H. C. Boonen, J. G. De Mey, G-proteins are involved in contractile responses of isolated mesenteric resistance arteries to agonists. Naunyn Schmiedebergs Arch Pharmacol 342, 462-468 (1990).

50. B. J. Heesen, J. G. De Mey, Effects of cyclic AMP-affecting agents on contractile reactivity of isolated mesenteric and renal resistance arteries of the rat. Br J Pharmacol 101, 859-864 (1990).

51. A. J. Karsten, H. Derouet, M. Ziegler, R. E. Eckert, Involvement of cyclic nucleotides in renal artery smooth muscle relaxation. Urol Res 30, 367-373 (2003).

52. C. Vettel, K. Wittig, A. Vogt, C. M. Wuertz, A. El-Armouche, S. Lutz, T. Wieland, A novel player in cellular hypertrophy: Gibetagamma/PI3K-dependent activation of the RacGEF TIAM-1 is required for alpha(1)-adrenoceptor induced hypertrophy in neonatal rat cardiomyocytes. J Mol Cell Cardiol 53, 165-175 (2012).

53. M. Billaud, A. W. Lohman, S. R. Johnstone, L. A. Biwer, S. Mutchler, B. E. Isakson, Regulation of cellular communication by signaling microdomains in the blood vessel wall. Pharmacological reviews 66, 513-569 (2014).

54. A. W. Moore, W. F. Jackson, S. S. Segal, Regional heterogeneity of alpha-adrenoreceptor subtypes in arteriolar networks of mouse skeletal muscle. The Journal of physiology 588, 4261-4274 (2010).

55. F. A. Dinenno, J. H. Eisenach, N. M. Dietz, M. J. Joyner, Post-junctional alpha-adrenoceptors and basal limb vascular tone in healthy men. The Journal of physiology 540, 1103-1110 (2002).

56. M. Ohyanagi, J. E. Faber, K. Nishigaki, Differential activation of alpha 1- and alpha 2-adrenoceptors on microvascular smooth muscle during sympathetic nerve stimulation. Circulation research 68, 232-244 (1991).

57. S. Guimaraes, D. Moura, Vascular adrenoceptors: an update. Pharmacological reviews 53, 319-356 (2001).

58. T. Katsuragi, S. Tamesue, C. Sato, Y. Sato, T. Furukawa, ATP release by angiotensin II from segments and cultured smooth muscle cells of guinea-pig *taenia coli*. Naunyn Schmiedebergs Arch Pharmacol 354, 796-799 (1996).

59. Y. Cheng, K. J. Mansfield, S. L. Sandow, P. Sadananda, E. Burcher, K. H. Moore, Porcine bladder urothelial, myofibroblast, and detrusor muscle cells: characterization and ATP release. Front Pharmacol 2, 27 (2011).

60. E. F. Diezmos, S. L. Sandow, I. Markus, D. Shevy Perera, D. Z. Lubowski, D. W. King, P. P. Bertrand, L. Liu, Expression and localization of pannexin-1 hemichannels in human colon in health and disease. Neurogastroenterology and motility: the official journal of the European Gastrointestinal Motility Society 25, e395-405 (2013).

61. M. A. Timoteo, I. Carneiro, I. Silva, J. B. Noronha-Matos, F. Ferreirinha, M. Silva-Ramos, P. Correia-de-Sa, ATP released via pannexin-1 hemichannels mediates bladder overactivity triggered by urothelial P2Y6 receptors. Biochem Pharmacol 87, 371-379 (2014).

62. T. A. Edwards, A. J. Wilson, Helix-mediated protein-protein interactions as targets for intervention using foldamers. Amino Acids 41, 743-754 (2011).

63. V. Azzarito, K. Long, N. S. Murphy, A. J. Wilson, Inhibition of alpha-helix-mediated protein-protein interactions using designed molecules. Nat Chem 5, 161-173 (2013).

64. J. Wang, G. Dahl, SCAM analysis of Panx1 suggests a peculiar pore structure. The Journal of general physiology 136, 515-527 (2010).

65. B. K. Kay, M. P. Williamson, M. Sudol, The importance of being proline: the interaction of proline-rich motifs in signaling proteins with their cognate domains. The FASEB journal: official publication of the Federation of American Societies for Experimental Biology 14, 231-241 (2000).

66. B. N. Giepmans, Gap junctions and connexin-interacting proteins. Cardiovasc Res 62, 233-245 (2004).

67. M. A. Riquelme, L. A. Cea, J. L. Vega, M. P. Boric, H. Monyer, M. V. Bennett, M. Frank, K. Willecke, J. C. Saez, The ATP required for potentiation of skeletal muscle contraction is released via pannexin hemichannels. Neuropharmacology 75, 594-603 (2013).

68. T. P. Robertson, J. N. Moore, E. Noschka, T. H. Lewis, S. J. Lewis, J. F. Peroni, Effects of Rho-kinase and Src protein tyrosine kinase inhibition on agonist-induced vasoconstriction of arteries and veins of the equine laminar dermis. Am J Vet Res 68, 886-894 (2007).

69. X. X. Xiong, L. J. Gu, J. Shen, X. H. Kang, Y. Y. Zheng, S. B. Yue, S. M. Zhu, Probenecid protects against transient focal cerebral ischemic injury by inhibiting HMGB1 release and attenuating AQP4 expression in mice. Neurochem Res 39, 216-224 (2014).

70. S. J. Coker, A. J. Batey, I. D. Lightbown, M. E. Diaz, D. A. Eisner, Effects of mefloquine on cardiac contractility and electrical activity in vivo, in isolated cardiac preparations, and in single ventricular myocytes. British journal of pharmacology 129, 323-330 (2000).

71. R. Iglesias, D. C. Spray, E. Scemes, Mefloquine blockade of Pannexin1 currents: resolution of a conflict. Cell communication & adhesion 16, 131-137 (2009).

72. A. Wirth, Z. Benyo, M. Lukasova, B. Leutgeb, N. Wettschureck, S. Gorbey, P. Orsy, B. Horvath, C. Maser-Gluth, E. Greiner, B. Lemmer, G. Schutz, J. S. Gutkind, S. Offermanns, G12-G13-LARG-mediated signaling in vascular smooth muscle is required for salt-induced hypertension. Nat Med 14, 64-68 (2008).

73. M. Billaud, A. W. Lohman, A. C. Straub, T. Parpaite, S. R. Johnstone, B. E. Isakson, Characterization of the thoracodorsal artery: morphology and reactivity. Microcirculation 19, 360-372 (2012).

74. M. V. Artamonov, K. Momotani, A. Stevenson, D. R. Trentham, U. Derewenda, Z. S. Derewenda, P. W. Read, J. S. Gutkind, A. V. Somlyo, Agonist-induced Ca2+ sensitization in smooth muscle: redundancy of Rho guanine nucleotide exchange factors (RhoGEFs) and response kinetics, a caged compound study. The Journal of biological chemistry 288, 34030-34040 (2013).

75. S. Cechova, Q. Zeng, M. Billaud, S. Mutchler, C. K. Rudy, A. C. Straub, L. Chi, F. R. Chan, J. Hu, R. Griffiths, N. L. Howell, K. Madsen, B. L. Jensen, L. A. Palmer, R. M. Carey, S. S. Sung, S. M. Malakauskas, B. E. Isakson, T. H. Le, Loss of collectrin, an angiotensin-converting enzyme 2 homolog, uncouples endothelial nitric oxide synthase and causes hypertension and vascular dysfunction. Circulation 128, 1770-1780 (2013).

What is claimed is:

1. A method to inhibit or reduce vasoconstriction comprising administering to a subject in need thereof a pharmaceutical composition comprising an effective amount of a peptide comprising amino acid sequence KYPIVEQYLK (SEQ ID NO:1) and conservative amino acid substitutions thereof, said peptide further comprising a plasma membrane permeability sequence.

2. The method of claim 1, wherein the plasma membrane permeability sequence comprises Human Immunodeficiency Virus (HIV)-tat tag amino acid sequence YGRKKQRRR (SEQ ID NO:2).

3. The method of claim 1, wherein said peptide consists of KYPIVEQYLKYGRKKQRRR (SEQ ID NO:3).

4. The method of claim 1, wherein said vasoconstriction is alpha1 adrenoreceptor ($\alpha$1AR)-mediated vasoconstriction.

5. The method of claim 4, wherein said vasoconstriction requires $\alpha$1AR stimulated activation of pannexin 1 (Panx1).

6. The method of claim 5, wherein said method reduces or inhibits Panx1 activity.

7. The method of claim 6, wherein one or two additional inhibitors of Panx1 activity are administered.

8. The method of claim 6, wherein said vasoconstriction is in a blood vessel susceptible to constriction by an $\alpha$1AR agonist.

9. The method of claim 8, wherein said Panx1 activity is smooth muscle cell (SMC) Panx1 activity.

10. The method of claim 1, wherein said method decreases blood pressure.

11. The method of claim 1, wherein said method reduces vasoconstriction of resistance vasculature.

12. The method of claim 1, wherein said method relaxes resistance arterioles.

13. The method of claim 1, wherein said administration is selected from the group consisting of intravenous, intraperitoneal, oral, topical, direct, intramuscular, intra-arterial, intramedullary, intrathecal, intraventricular, transdermal, subcutaneous, intranasal, enteral, sublingual, and rectal.

14. The method of claim 1, wherein said method inhibits an increase in blood pressure.

15. The method of claim 1, wherein said method inhibits $\alpha$1AR simulated ATP release.

16. The method of claim 1, wherein said vasoconstriction is associated with a disease, disorder, or condition.

17. The method of claim 16, wherein said disease, disorder, or condition is selected from the group consisting of hypertension, primary hypertension, treatment resistant hypertension, obesity-related hypertension, stroke, myocardial infarction, coronary artery disease, pulmonary arterial hypertension, sickle cell disease, rheumatoid arthritis, bladder disorders, and intestinal peristalsis disorders.

18. The method of claim 12, wherein said effective amount of a peptide is administered at a dosage ranging from about 1.0 milligram (mg)/kilogram (kg) body weight to about 20.0 mg/kg body weight.

19. The method of claim 18, wherein said dose is 5.0 mg/kg body weight.

* * * * *

SEQUENCE LISTING

```
<160> NUMBER OF SEQ ID NOS: 7

<210> SEQ ID NO 1
<211> LENGTH: 10
<212> TYPE: PRT
<213> ORGANISM: Homo sapiens

<400> SEQUENCE: 1

Lys Tyr Pro Ile Val Glu Gln Tyr Leu Lys
1               5                   10
```

```
<210> SEQ ID NO 2
<211> LENGTH: 9
<212> TYPE: PRT
<213> ORGANISM: Human immunodeficiency virus

<400> SEQUENCE: 2

Tyr Gly Arg Lys Lys Gln Arg Arg Arg
1               5

<210> SEQ ID NO 3
<211> LENGTH: 19
<212> TYPE: PRT
<213> ORGANISM: Unknown
<220> FEATURE:
<223> OTHER INFORMATION: hybrid of human and HIV tat seq.

<400> SEQUENCE: 3

Lys Tyr Pro Ile Val Glu Gln Tyr Leu Lys Tyr Gly Arg Lys Lys Gln
1               5                   10                  15

Arg Arg Arg

<210> SEQ ID NO 4
<211> LENGTH: 10
<212> TYPE: PRT
<213> ORGANISM: Homo sapiens

<400> SEQUENCE: 4

Val Gly Gln Ser Leu Trp Glu Ile Ser Glu
1               5                   10

<210> SEQ ID NO 5
<211> LENGTH: 16
<212> TYPE: PRT
<213> ORGANISM: Homo sapiens

<400> SEQUENCE: 5

Arg Arg Leu Lys Val Tyr Glu Ile Leu Pro Thr Phe Asp Val Leu His
1               5                   10                  15

<210> SEQ ID NO 6
<211> LENGTH: 10
<212> TYPE: PRT
<213> ORGANISM: Homo sapiens

<400> SEQUENCE: 6

Ile Pro Thr Ser Leu Gln Thr Lys Gly Glu
1               5                   10

<210> SEQ ID NO 7
<211> LENGTH: 10
<212> TYPE: PRT
<213> ORGANISM: Unknown
<220> FEATURE:
<223> OTHER INFORMATION: scrambled human sequence

<400> SEQUENCE: 7

Ile Tyr Leu Tyr Val Glu Gln Lys Pro Tyr
1               5                   10
```